US012685578B2

(12) United States Patent
Castellvi et al.

(10) Patent No.: US 12,685,578 B2
(45) Date of Patent: Jul. 21, 2026

(54) PULSED ELECTRIC FIELD WAVEFORM MANIPULATION AND USE

(71) Applicant: Galvanize Therapeutics, Inc., Redwood City, CA (US)

(72) Inventors: Quim Castellvi, Barcelona (ES); Robert E. Neal, II, Redwood City, CA (US); Timothy J. O'Brien, Santa Clara, CA (US); Jonathan R. Waldstreicher, West Orange, NJ (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 682 days.

(21) Appl. No.: 17/962,142

(22) Filed: Oct. 7, 2022

(65) Prior Publication Data

US 2023/0172650 A1 Jun. 8, 2023

Related U.S. Application Data

(63) Continuation of application No. PCT/US2021/026221, filed on Apr. 7, 2021.
(Continued)

(51) Int. Cl.
*A61B 18/12* (2006.01)
*A61B 18/00* (2006.01)
*A61B 18/14* (2006.01)

(52) U.S. Cl.
CPC ...... *A61B 18/1206* (2013.01); *A61B 18/1492* (2013.01); *A61B 2018/00577* (2013.01); *A61B 2018/00791* (2013.01)

(58) Field of Classification Search
CPC ............ A61B 18/1206; A61B 18/1492; A61B 2018/00577; A61B 2018/00791
See application file for complete search history.

(56) References Cited

U.S. PATENT DOCUMENTS

| | | | |
|---|---|---|---|
| 874,178 A | 12/1907 | Forest | |
| 4,249,541 A | 2/1981 | Pratt | |

(Continued)

FOREIGN PATENT DOCUMENTS

| | | | |
|---|---|---|---|
| AT | 306859 B | 4/1973 | |
| AU | 200048007 | 11/2000 | |

(Continued)

OTHER PUBLICATIONS

EP21785398.5 Extended European Search Report dated Apr. 4, 2024.

(Continued)

*Primary Examiner* — Linda C Dvorak
*Assistant Examiner* — Abigail Bock
(74) *Attorney, Agent, or Firm* — Greenberg Traurig, LLP; Christopher C. Bolten

(57) ABSTRACT

Devices, systems and methods are provided for delivering pulsed electric field (PEF) energy to tissue through one or more energy delivery bodies, each having one or more electrodes. The PEF energy is generated from a waveform having a variety of features. Waveform delays, such as inter-pulse delays, inter-cycle delays, inter-phase delays, inter-packet delays, inter-bundle delays, may be utilized within a treatment to obtain a desired outcome. In particular, these delays may be specifically manipulated to obtain particular desired outcomes. For example, one, some or all of these delays may be manipulated to control various aspects of PEF therapy so as to mitigate any associated risks, such as gas formation, electrical discharge, cavity formation, muscle contraction, and temperature rise, to name a few. In some embodiments, the delays distribute the period over which PEF energy is delivered, resulting in marked changes and optimization to the treatment delivery outcomes.

25 Claims, 18 Drawing Sheets

Related U.S. Application Data

(60) Provisional application No. 63/078,784, filed on Sep. 15, 2020, provisional application No. 63/007,233, filed on Apr. 8, 2020.

(56)                    References Cited

U.S. PATENT DOCUMENTS

| | | | |
|---|---|---|---|
| 5,232,856 A | 8/1993 | Firth |
| 5,304,120 A | 4/1994 | Crandell et al. |
| 5,386,837 A | 2/1995 | Sterzer |
| 5,507,724 A | 4/1996 | Hofmann et al. |
| 5,601,588 A | 2/1997 | Tonomura et al. |
| 5,683,384 A | 11/1997 | Gough et al. |
| 5,704,908 A | 1/1998 | Hofmann et al. |
| 5,833,710 A | 11/1998 | Jacobson |
| 5,906,609 A | 5/1999 | Assa et al. |
| 5,972,026 A | 10/1999 | Laufer et al. |
| 6,009,347 A | 12/1999 | Hofmann |
| 6,038,478 A | 3/2000 | Yuen et al. |
| 6,041,252 A | 3/2000 | Walker et al. |
| 6,078,490 A | 6/2000 | Walters |
| 6,083,255 A | 7/2000 | Laufer et al. |
| 6,107,699 A | 8/2000 | Swanson |
| 6,120,493 A | 9/2000 | Hofmann |
| 6,200,333 B1 | 3/2001 | Laufer |
| 6,219,577 B1 | 4/2001 | Brown, III et al. |
| 6,233,482 B1 | 5/2001 | Hofmann et al. |
| 6,248,056 B1 | 6/2001 | Persson |
| 6,261,831 B1 | 7/2001 | Agee |
| 6,273,907 B1 | 8/2001 | Laufer |
| 6,283,988 B1 | 9/2001 | Laufer et al. |
| 6,283,989 B1 | 9/2001 | Laufer et al. |
| 6,299,633 B1 | 10/2001 | Laufer |
| 6,326,177 B1 | 12/2001 | Schoenbach et al. |
| 6,366,808 B1 | 4/2002 | Schroeppel et al. |
| 6,411,852 B1 | 6/2002 | Danek et al. |
| 6,488,673 B1 | 12/2002 | Laufer et al. |
| 6,520,950 B1 | 2/2003 | Hofmann et al. |
| 6,569,149 B2 | 5/2003 | Dev et al. |
| 6,634,363 B1 | 10/2003 | Danek et al. |
| 6,678,558 B1 | 1/2004 | Dimmer et al. |
| 6,697,670 B2 | 2/2004 | Chomenky et al. |
| 6,733,485 B1 | 5/2004 | Whitehurst et al. |
| 6,738,663 B2 | 5/2004 | Schroeppel et al. |
| 6,770,070 B1 | 8/2004 | Balbierz |
| 6,795,728 B2 | 9/2004 | Chornenky et al. |
| 6,892,099 B2 | 5/2005 | Jaafar et al. |
| 6,994,706 B2 | 2/2006 | Chornenky et al. |
| 7,027,869 B2 | 4/2006 | Danek et al. |
| 7,054,685 B2 | 5/2006 | Dimmer et al. |
| 7,104,987 B2 | 9/2006 | Biggs et al. |
| 7,130,697 B2 | 10/2006 | Chornenky et al. |
| 7,171,263 B2 | 1/2007 | Darvish |
| 7,198,635 B2 | 4/2007 | Danek et al. |
| 7,200,445 B1 | 4/2007 | Dalbec et al. |
| 7,211,083 B2 | 5/2007 | Chornenky et al. |
| 7,255,693 B1 | 8/2007 | Johnston et al. |
| 7,264,002 B2 | 9/2007 | Danek et al. |
| 7,273,055 B2 | 9/2007 | Danek et al. |
| 7,344,533 B2 | 3/2008 | Pearson et al. |
| 7,395,112 B2 | 7/2008 | Keisari et al. |
| 7,412,284 B2 | 8/2008 | Hofmann |
| 7,412,285 B2 | 8/2008 | Schroeppel et al. |
| 7,425,212 B1 | 9/2008 | Danek et al. |
| 7,542,802 B2 | 6/2009 | Danek et al. |
| 7,556,624 B2 | 7/2009 | Laufer et al. |
| 7,565,205 B2 | 7/2009 | Palti |
| 7,565,206 B2 | 7/2009 | Palti |
| 7,594,925 B2 | 9/2009 | Danek et al. |
| 7,599,745 B2 | 10/2009 | Palti |
| 7,599,746 B2 | 10/2009 | Palti |
| 7,620,451 B2 | 11/2009 | Demarais et al. |
| 7,655,004 B2 | 2/2010 | Long |
| 7,680,543 B2 | 3/2010 | Azure |
| 7,708,768 B2 | 5/2010 | Danek et al. |
| 7,713,740 B2 | 5/2010 | Jaroszeski et al. |
| 7,722,606 B2 | 5/2010 | Azure |
| 7,740,017 B2 | 6/2010 | Danek et al. |
| 7,742,811 B2 | 6/2010 | Schroeppel et al. |
| 7,756,583 B2 | 7/2010 | Demarais et al. |
| 7,765,010 B2 | 7/2010 | Chornenky et al. |
| 7,770,584 B2 | 8/2010 | Danek et al. |
| 7,805,201 B2 | 9/2010 | Palti |
| 7,819,908 B2 | 10/2010 | Ingenito |
| 7,824,870 B2 | 11/2010 | Kovalcheck et al. |
| 7,837,679 B2 | 11/2010 | Biggs et al. |
| RE42,016 E | 12/2010 | Chornenky et al. |
| 7,853,331 B2 | 12/2010 | Kaplan et al. |
| 7,853,333 B2 | 12/2010 | Demarais |
| 7,854,734 B2 | 12/2010 | Biggs et al. |
| 7,879,610 B1 | 2/2011 | Heller et al. |
| 7,906,124 B2 | 3/2011 | Laufer et al. |
| 7,917,227 B2 | 3/2011 | Palti |
| RE42,277 E | 4/2011 | Jaafar et al. |
| 7,921,855 B2 | 4/2011 | Danek et al. |
| 7,931,647 B2 | 4/2011 | Wizeman et al. |
| 7,937,143 B2 | 5/2011 | Demarais et al. |
| 7,938,123 B2 | 5/2011 | Danek et al. |
| 7,938,824 B2 | 5/2011 | Chornenky et al. |
| 7,949,407 B2 | 5/2011 | Kaplan et al. |
| 7,959,628 B2 | 6/2011 | Schaer et al. |
| 7,992,572 B2 | 8/2011 | Danek et al. |
| 8,007,496 B2 | 8/2011 | Rioux et al. |
| 8,014,854 B2 | 9/2011 | Schroeppel et al. |
| 8,019,414 B2 | 9/2011 | Palti |
| 8,024,048 B2 | 9/2011 | Schroeppel et al. |
| 8,026,223 B1 | 9/2011 | Heller et al. |
| RE42,835 E | 10/2011 | Chornenky et al. |
| 8,048,067 B2 | 11/2011 | Davalos et al. |
| RE43,009 E | 12/2011 | Chornenky et al. |
| 8,105,324 B2 | 1/2012 | Palanker et al. |
| 8,109,926 B2 | 2/2012 | Azure |
| 8,114,070 B2 | 2/2012 | Rubinsky et al. |
| 8,120,207 B2 | 2/2012 | Sanders et al. |
| 8,131,371 B2 | 3/2012 | Demarals et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,161,978 B2 | 4/2012 | Danek et al. |
| 8,181,656 B2 | 5/2012 | Danek et al. |
| 8,221,411 B2 | 7/2012 | Francischelli et al. |
| 8,231,603 B2 | 7/2012 | Hobbs et al. |
| 8,235,983 B2 | 8/2012 | Webster et al. |
| 8,244,345 B2 | 8/2012 | Palti |
| 8,251,070 B2 | 8/2012 | Danek et al. |
| 8,251,986 B2 | 8/2012 | Chornenky et al. |
| 8,257,413 B2 | 9/2012 | Danek et al. |
| 8,267,094 B2 | 9/2012 | Danek et al. |
| 8,282,631 B2 | 10/2012 | Davalos et al. |
| 8,292,882 B2 | 10/2012 | Danek et al. |
| 8,298,222 B2 | 10/2012 | Rubinsky et al. |
| 8,298,224 B2 | 10/2012 | Danek et al. |
| 8,406,870 B2 | 3/2013 | Palti |
| 8,425,505 B2 | 4/2013 | Long |
| 8,428,710 B2 | 4/2013 | Kuriyama et al. |
| 8,443,810 B2 | 5/2013 | Danek et al. |
| 8,449,538 B2 | 5/2013 | Long |
| 8,459,268 B2 | 6/2013 | Danek et al. |
| 8,464,723 B2 | 6/2013 | Danek et al. |
| 8,465,484 B2 | 6/2013 | Davalos et al. |
| 8,465,486 B2 | 6/2013 | Danek et al. |
| 8,480,667 B2 | 7/2013 | Kaplan et al. |
| 8,500,713 B2 | 8/2013 | Ferek-Petric |
| 8,504,147 B2 | 8/2013 | Deem et al. |
| 8,512,334 B2 | 8/2013 | Nuccitelli et al. |
| 8,521,274 B2 | 8/2013 | Gutsol et al. |
| 8,534,291 B2 | 9/2013 | Danek et al. |
| 8,540,710 B2 | 9/2013 | Johnson et al. |
| 8,562,588 B2 | 10/2013 | Hobbs et al. |
| 8,568,403 B2 | 10/2013 | Soltesz et al. |
| 8,579,888 B2 | 11/2013 | Hoey et al. |
| 8,584,681 B2 | 11/2013 | Danek et al. |
| 8,600,494 B2 | 12/2013 | Schroeppel et al. |

(56)                    References Cited

U.S. PATENT DOCUMENTS

| | | | |
|---|---|---|---|
| 8,603,087 | B2 | 12/2013 | Rubinsky et al. |
| 8,620,423 | B2 | 12/2013 | Demarais et al. |
| 8,632,534 | B2 | 1/2014 | Pearson et al. |
| 8,634,929 | B2 | 1/2014 | Chornenky et al. |
| 8,636,726 | B1 | 1/2014 | Wells et al. |
| 8,640,711 | B2 | 2/2014 | Danek et al. |
| 8,647,338 | B2 | 2/2014 | Chornenky et al. |
| 8,652,130 | B2 | 2/2014 | Kreindel |
| 8,676,309 | B2 | 3/2014 | Deem et al. |
| 8,721,632 | B2 | 5/2014 | Hoey et al. |
| 8,733,367 | B2 | 5/2014 | Danek et al. |
| 8,740,895 | B2 | 6/2014 | Mayse et al. |
| 8,753,335 | B2 | 6/2014 | Moshe et al. |
| 8,774,922 | B2 | 7/2014 | Zarins et al. |
| 8,777,943 | B2 | 7/2014 | Mayse et al. |
| 8,802,643 | B1 | 8/2014 | Heller et al. |
| 8,814,860 | B2 | 8/2014 | Davalos et al. |
| 8,828,945 | B2 | 9/2014 | Laufer et al. |
| 8,888,769 | B2 | 11/2014 | Biggs et al. |
| 8,903,488 | B2 | 12/2014 | Callas et al. |
| 8,906,006 | B2 | 12/2014 | Chornenky et al. |
| 8,911,430 | B2 | 12/2014 | Hoey et al. |
| 8,911,439 | B2 | 12/2014 | Mayse et al. |
| 8,920,413 | B2 | 12/2014 | Danek et al. |
| 8,926,606 | B2 | 1/2015 | Davalos et al. |
| 8,927,518 | B1 | 1/2015 | Heller et al. |
| 8,944,071 | B2 | 2/2015 | Loomas et al. |
| 8,968,210 | B2 | 3/2015 | Mugan et al. |
| 8,974,417 | B2 | 3/2015 | Kimura et al. |
| 8,992,513 | B2 | 3/2015 | Delaney |
| 8,992,517 | B2 | 3/2015 | Davalos et al. |
| 9,005,189 | B2 | 4/2015 | Davalos et al. |
| 9,017,324 | B2 | 4/2015 | Mayse et al. |
| 9,027,564 | B2 | 5/2015 | Danek et al. |
| 9,033,976 | B2 | 5/2015 | Danek et al. |
| 9,037,230 | B2 | 5/2015 | Goldfarb et al. |
| 9,078,665 | B2 | 7/2015 | Moss et al. |
| 9,095,323 | B2 | 8/2015 | Chu et al. |
| 9,101,764 | B2 | 8/2015 | Nuccitelli et al. |
| 9,108,052 | B2 | 8/2015 | Jarrard |
| 9,125,666 | B2 | 9/2015 | Steinke et al. |
| 9,144,449 | B2 | 9/2015 | Burr et al. |
| 9,168,373 | B2 | 10/2015 | Nuccitelli et al. |
| 9,173,704 | B2 | 11/2015 | Hobbs et al. |
| 9,186,128 | B2 | 11/2015 | Mugan et al. |
| 9,198,733 | B2 | 12/2015 | Neal, II et al. |
| 9,199,091 | B2 | 12/2015 | Danek et al. |
| 9,211,155 | B2 | 12/2015 | Fruland et al. |
| 9,242,041 | B2 | 1/2016 | Kosik et al. |
| 9,259,235 | B2 | 2/2016 | Chierchia et al. |
| 9,265,563 | B2 | 2/2016 | Racz et al. |
| 9,272,132 | B2 | 3/2016 | Laufer et al. |
| 9,277,957 | B2 | 3/2016 | Long et al. |
| 9,283,374 | B2 | 3/2016 | Hollett et al. |
| 9,289,606 | B2 | 3/2016 | Paul et al. |
| 9,295,516 | B2 | 3/2016 | Pearson et al. |
| 9,301,796 | B2 | 4/2016 | Burr et al. |
| 9,308,043 | B2 | 4/2016 | Zarins et al. |
| 9,308,044 | B2 | 4/2016 | Zarins et al. |
| 9,314,620 | B2 | 4/2016 | Long et al. |
| 9,327,122 | B2 | 5/2016 | Zarins et al. |
| 9,332,973 | B2 | 5/2016 | McWeeney et al. |
| 9,339,328 | B2 | 5/2016 | Ortiz et al. |
| 9,339,618 | B2 | 5/2016 | Deem et al. |
| 9,358,024 | B2 | 6/2016 | Danek et al. |
| 9,375,268 | B2 | 6/2016 | Long |
| 9,414,881 | B2 | 8/2016 | Callas et al. |
| 9,439,726 | B2 | 9/2016 | Zarins et al. |
| 9,486,266 | B2 | 11/2016 | Soltesz et al. |
| 9,510,888 | B2 | 12/2016 | Lalonde |
| 9,526,568 | B2 | 12/2016 | Ohri et al. |
| 9,572,619 | B2 | 2/2017 | Laufer et al. |
| 9,598,691 | B2 | 3/2017 | Davalos |
| 9,610,067 | B2 | 4/2017 | Sekikawa |
| 9,610,364 | B1 | 4/2017 | Heller et al. |
| 9,629,912 | B2 | 4/2017 | Soikum et al. |
| 9,649,153 | B2 | 5/2017 | Mayse et al. |
| 9,649,154 | B2 | 5/2017 | Mayse et al. |
| 9,655,669 | B2 | 5/2017 | Palti et al. |
| 9,656,055 | B2 | 5/2017 | Weissberg et al. |
| 9,656,066 | B2 | 5/2017 | Nuccitelli et al. |
| 9,668,809 | B2 | 6/2017 | Mayse et al. |
| 9,675,406 | B2 | 6/2017 | Moss et al. |
| 9,675,412 | B2 | 6/2017 | Mayse et al. |
| 9,681,909 | B2 | 6/2017 | Bhargav et al. |
| 9,700,368 | B2 | 7/2017 | Callas et al. |
| 9,717,552 | B2 | 8/2017 | Cosman |
| 9,724,155 | B2 | 8/2017 | Nuccitelli et al. |
| 9,788,707 | B2 | 10/2017 | Tinkham et al. |
| 9,789,331 | B2 | 10/2017 | Danek et al. |
| 9,820,724 | B2 | 11/2017 | Mamiya |
| 9,820,797 | B2 | 11/2017 | Burr et al. |
| 9,833,617 | B2 | 12/2017 | Travers et al. |
| 9,867,648 | B2 | 1/2018 | Mulcahey et al. |
| 9,867,652 | B2 | 1/2018 | Sano et al. |
| 9,877,708 | B2 | 1/2018 | McWeeney et al. |
| 9,888,956 | B2 | 2/2018 | Model et al. |
| 9,895,189 | B2 | 2/2018 | Pearson |
| 9,931,161 | B2 | 4/2018 | Willis |
| 9,931,163 | B2 | 4/2018 | Danek et al. |
| 9,943,684 | B2 | 4/2018 | Nuccitelli et al. |
| 9,956,391 | B2 | 5/2018 | Weissberg et al. |
| 9,974,609 | B2 | 5/2018 | Hollett et al. |
| 9,987,081 | B1 | 6/2018 | Bowers et al. |
| 9,993,296 | B2 | 6/2018 | Ladtkow et al. |
| 9,999,465 | B2 | 6/2018 | Long et al. |
| 10,010,666 | B2 | 7/2018 | Rubinsky et al. |
| 10,016,232 | B1 | 7/2018 | Bowers et al. |
| D831,199 | S | 10/2018 | Holton et al. |
| D832,426 | S | 10/2018 | Holton et al. |
| 10,130,423 | B1 | 11/2018 | Viswanathan et al. |
| 10,136,943 | B1 | 11/2018 | Cosman, Jr. et al. |
| 10,143,512 | B2 | 12/2018 | Rubinsky et al. |
| 10,143,759 | B1 | 12/2018 | Heller et al. |
| 10,149,714 | B2 | 12/2018 | Mayse et al. |
| 10,154,869 | B2 | 12/2018 | Onik et al. |
| 10,154,874 | B2 | 12/2018 | Davalos et al. |
| 10,166,071 | B2 | 1/2019 | Sherman et al. |
| 10,172,673 | B2 | 1/2019 | Viswanathan et al. |
| 10,238,447 | B2 | 3/2019 | Neal et al. |
| 10,245,105 | B2 | 4/2019 | Davalos et al. |
| 10,271,893 | B2 | 4/2019 | Stewart et al. |
| 10,292,755 | B2 | 5/2019 | Arena et al. |
| 10,322,286 | B2 | 6/2019 | Viswanathan et al. |
| 10,391,125 | B2 | 8/2019 | Nuccitelli et al. |
| 10,426,847 | B2 | 10/2019 | Pierce et al. |
| 10,448,989 | B2 | 10/2019 | Arena et al. |
| 10,471,254 | B2 | 11/2019 | Sano et al. |
| 10,499,980 | B2 | 12/2019 | Shuman et al. |
| 10,639,098 | B2 | 5/2020 | Cosman |
| 10,694,972 | B2 | 6/2020 | Davalos et al. |
| 10,702,337 | B2 | 7/2020 | Waldstreicher et al. |
| 10,779,887 | B2 | 9/2020 | Deem et al. |
| 10,849,678 | B2 | 12/2020 | Onik et al. |
| 10,874,451 | B2 | 12/2020 | Athos et al. |
| 10,939,958 | B2 | 3/2021 | Waldstreicher et al. |
| 10,945,714 | B2 | 3/2021 | Ralph |
| 11,039,819 | B2 | 6/2021 | Gonzalez |
| 11,051,871 | B2 | 7/2021 | Nuccitelli et al. |
| 11,052,246 | B2 | 7/2021 | Stewart et al. |
| 11,065,372 | B2 | 7/2021 | Stender et al. |
| 11,071,530 | B2 | 7/2021 | Wang et al. |
| 11,167,095 | B2 | 11/2021 | Ralph et al. |
| 11,324,543 | B2 | 5/2022 | Waldstreicher et al. |
| 11,369,433 | B2 | 6/2022 | Waldstreicher et al. |
| 11,382,681 | B2 | 7/2022 | Arena et al. |
| 11,471,208 | B2 | 10/2022 | Waldstreicher et al. |
| 11,547,851 | B2 | 1/2023 | Krimsky et al. |
| 11,638,603 | B2 | 5/2023 | Sano et al. |
| 11,696,797 | B2 | 7/2023 | Onik |
| 11,723,712 | B2 | 8/2023 | Athos et al. |
| 11,737,810 | B2 | 8/2023 | Davalos et al. |
| 11,903,690 | B2 | 2/2024 | Davalos et al. |
| 11,938,317 | B2 | 3/2024 | Krimsky et al. |

(56)     References Cited

U.S. PATENT DOCUMENTS

| 11,952,568 B2 | 4/2024 | Neal, II et al. |
| 12,059,197 B2 | 8/2024 | Davalos et al. |
| 12,173,280 B2 | 12/2024 | Neal, II et al. |
| 12,178,496 B2 | 12/2024 | Jauregui Johnston et al. |
| 12,201,349 B2 | 1/2025 | Pearson et al. |
| 12,349,967 B2 | 7/2025 | Waldstreicher et al. |
| 12,403,305 B2 | 9/2025 | Waldstreicher et al. |
| 2001/0008016 A1 | 7/2001 | Kotani et al. |
| 2001/0020166 A1 | 9/2001 | Daly et al. |
| 2002/0010491 A1 | 1/2002 | Schoenbach et al. |
| 2002/0022839 A1 | 2/2002 | Stewart et al. |
| 2002/0103483 A1 | 8/2002 | Edwards |
| 2002/0104318 A1 | 8/2002 | Jaafar et al. |
| 2002/0115991 A1 | 8/2002 | Edwards |
| 2002/0188242 A1 | 12/2002 | Wu |
| 2002/0198567 A1 | 12/2002 | Keisari et al. |
| 2003/0170898 A1 | 9/2003 | Gundersen et al. |
| 2003/0199050 A1 | 10/2003 | Mangano et al. |
| 2004/0029240 A1 | 2/2004 | Acker |
| 2004/0044338 A1 | 3/2004 | Lennox et al. |
| 2004/0047855 A1 | 3/2004 | Ingenito |
| 2004/0102818 A1 | 5/2004 | Hakky et al. |
| 2005/0010270 A1 | 1/2005 | Laufer |
| 2005/0049542 A1 | 3/2005 | Sigg et al. |
| 2005/0096584 A1 | 5/2005 | Ferek-Petric |
| 2005/0096644 A1* | 5/2005 | Hall ................... A61B 18/14 |
| | | 606/41 |
| 2005/0096647 A1 | 5/2005 | Steinke et al. |
| 2005/0170510 A1 | 8/2005 | Huang et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0177150 A1 | 8/2005 | Amoah et al. |
| 2005/0222646 A1 | 10/2005 | Kroll et al. |
| 2005/0288730 A1 | 12/2005 | Deem et al. |
| 2006/0264752 A1 | 11/2006 | Rubinsky et al. |
| 2006/0269531 A1 | 11/2006 | Beebe et al. |
| 2006/0293725 A1 | 12/2006 | Rubinsky et al. |
| 2006/0293731 A1 | 12/2006 | Rubinsky et al. |
| 2007/0021803 A1 | 1/2007 | Deem et al. |
| 2007/0025919 A1 | 2/2007 | Deem et al. |
| 2007/0083239 A1 | 4/2007 | Demarais et al. |
| 2007/0093802 A1 | 4/2007 | Danek et al. |
| 2007/0106296 A1 | 5/2007 | Laufer et al. |
| 2007/0106348 A1 | 5/2007 | Laufer |
| 2007/0112349 A1 | 5/2007 | Danek et al. |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0129720 A1 | 6/2007 | Demarais et al. |
| 2007/0156135 A1 | 7/2007 | Rubinsky et al. |
| 2007/0191904 A1 | 8/2007 | Libbus et al. |
| 2007/0239213 A1 | 10/2007 | Palti |
| 2008/0015571 A1 | 1/2008 | Rubinsky et al. |
| 2008/0071264 A1 | 3/2008 | Azure |
| 2008/0132884 A1 | 6/2008 | Rubinsky et al. |
| 2008/0132885 A1 | 6/2008 | Rubinsky et al. |
| 2008/0161801 A1 | 7/2008 | Steinke et al. |
| 2008/0195174 A1 | 8/2008 | Walker et al. |
| 2008/0200912 A1 | 8/2008 | Long |
| 2008/0231337 A1 | 9/2008 | Krishnaswamy et al. |
| 2008/0269586 A1 | 10/2008 | Rubinsky et al. |
| 2008/0306570 A1 | 12/2008 | Rezai et al. |
| 2008/0319372 A1 | 12/2008 | Palti et al. |
| 2009/0043301 A1 | 2/2009 | Jarrard et al. |
| 2009/0069797 A1 | 3/2009 | Danek et al. |
| 2009/0118726 A1 | 5/2009 | Auth et al. |
| 2009/0157002 A1 | 6/2009 | Dumot et al. |
| 2009/0192504 A1 | 7/2009 | Askew |
| 2009/0192505 A1 | 7/2009 | Askew et al. |
| 2009/0192508 A1 | 7/2009 | Laufer et al. |
| 2009/0247933 A1 | 10/2009 | Maor et al. |
| 2009/0281477 A1 | 11/2009 | Mikus et al. |
| 2009/0292342 A1 | 11/2009 | Rubinsky et al. |
| 2009/0306644 A1 | 12/2009 | Mayse et al. |
| 2009/0318914 A1 | 12/2009 | Utley et al. |
| 2010/0004623 A1 | 1/2010 | Hamilton, Jr. et al. |
| 2010/0023004 A1 | 1/2010 | Francischelli et al. |
| 2010/0130975 A1 | 5/2010 | Long |
| 2010/0152725 A1 | 6/2010 | Pearson et al. |
| 2010/0160906 A1 | 6/2010 | Jarrard |
| 2010/0179530 A1 | 7/2010 | Long et al. |
| 2010/0204688 A1 | 8/2010 | Hoey et al. |
| 2010/0228248 A1 | 9/2010 | Griffin |
| 2010/0240995 A1 | 9/2010 | Nuccitelli et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0274236 A1 | 10/2010 | Krimsky |
| 2010/0324616 A1 | 12/2010 | Livnat et al. |
| 2011/0112527 A1 | 5/2011 | Hamilton, Jr. et al. |
| 2011/0118732 A1 | 5/2011 | Rubinsky et al. |
| 2011/0152855 A1 | 6/2011 | Mayse et al. |
| 2011/0166565 A1 | 7/2011 | Wizeman et al. |
| 2011/0190662 A1 | 8/2011 | McWeeney |
| 2011/0196288 A1 | 8/2011 | Kaplan et al. |
| 2011/0202052 A1 | 8/2011 | Gelbart et al. |
| 2011/0208166 A1 | 8/2011 | Dumot et al. |
| 2011/0288545 A1 | 11/2011 | Beebe et al. |
| 2012/0098351 A1 | 4/2012 | Ross |
| 2012/0109122 A1 | 5/2012 | Arena et al. |
| 2012/0143120 A1 | 6/2012 | Goldfarb et al. |
| 2012/0150172 A1 | 6/2012 | Ortiz et al. |
| 2012/0197243 A1 | 8/2012 | Sherman et al. |
| 2012/0220998 A1 | 8/2012 | Long et al. |
| 2012/0220999 A1 | 8/2012 | Long |
| 2012/0226101 A1 | 9/2012 | Tinkham et al. |
| 2012/0226271 A1 | 9/2012 | Callas et al. |
| 2012/0277741 A1 | 11/2012 | Davalos et al. |
| 2012/0310237 A1 | 12/2012 | Swanson |
| 2012/0315704 A1 | 12/2012 | Beebe et al. |
| 2012/0330299 A1 | 12/2012 | Webster et al. |
| 2012/0330306 A1 | 12/2012 | Long et al. |
| 2013/0006144 A1 | 1/2013 | Clancy et al. |
| 2013/0023873 A1 | 1/2013 | Danek et al. |
| 2013/0030425 A1 | 1/2013 | Stewart et al. |
| 2013/0030430 A1 | 1/2013 | Stewart et al. |
| 2013/0035747 A1 | 2/2013 | Danek et al. |
| 2013/0184702 A1 | 7/2013 | Neal, II et al. |
| 2013/0196441 A1 | 8/2013 | Rubinsky et al. |
| 2013/0211402 A1 | 8/2013 | Danek et al. |
| 2013/0218158 A1 | 8/2013 | Danek et al. |
| 2013/0225996 A1 | 8/2013 | Dillard et al. |
| 2013/0226167 A1 | 8/2013 | Kaplan et al. |
| 2013/0253415 A1 | 9/2013 | Sano et al. |
| 2013/0261389 A1 | 10/2013 | Long |
| 2013/0261683 A1 | 10/2013 | Soikum et al. |
| 2014/0018789 A1 | 1/2014 | Kaplan et al. |
| 2014/0018790 A1 | 1/2014 | Kaplan et al. |
| 2014/0025063 A1 | 1/2014 | Kaplan et al. |
| 2014/0039489 A1 | 2/2014 | Davalos et al. |
| 2014/0039491 A1 | 2/2014 | Bakos et al. |
| 2014/0046322 A1 | 2/2014 | Callas et al. |
| 2014/0052126 A1 | 2/2014 | Long et al. |
| 2014/0058294 A1 | 2/2014 | Gross et al. |
| 2014/0074078 A1 | 3/2014 | Kumar et al. |
| 2014/0081263 A1 | 3/2014 | Mesallum |
| 2014/0107478 A1 | 4/2014 | Seward et al. |
| 2014/0114378 A1 | 4/2014 | Danek et al. |
| 2014/0121663 A1 | 5/2014 | Pearson et al. |
| 2014/0128949 A1 | 5/2014 | Hollett et al. |
| 2014/0148635 A1 | 5/2014 | Danek et al. |
| 2014/0296844 A1 | 10/2014 | Kevin et al. |
| 2014/0324036 A1 | 10/2014 | Sachs et al. |
| 2014/0324037 A1 | 10/2014 | Hoey et al. |
| 2014/0330332 A1 | 11/2014 | Danek et al. |
| 2014/0341801 A1 | 11/2014 | Laufer et al. |
| 2014/0378964 A1 | 12/2014 | Pearson |
| 2015/0005766 A1 | 1/2015 | Rioux et al. |
| 2015/0025605 A1 | 1/2015 | Kaplan et al. |
| 2015/0038959 A1 | 2/2015 | Biggs et al. |
| 2015/0039059 A1 | 2/2015 | Mokelke et al. |
| 2015/0045788 A1 | 2/2015 | Litscher et al. |
| 2015/0066005 A1 | 3/2015 | Fan et al. |

(56) References Cited

U.S. PATENT DOCUMENTS

| | | |
|---|---|---|
| 2015/0066108 A1 | 3/2015 | Shi et al. |
| 2015/0080884 A1 | 3/2015 | Zarins et al. |
| 2015/0088120 A1 | 3/2015 | Garcia et al. |
| 2015/0105775 A1 | 4/2015 | Wizeman et al. |
| 2015/0112321 A1 | 4/2015 | Cadouri |
| 2015/0119879 A1 | 4/2015 | Jameson et al. |
| 2015/0141984 A1 | 5/2015 | Loomas et al. |
| 2015/0150618 A1 | 6/2015 | Onik et al. |
| 2015/0164584 A1 | 6/2015 | Davalos et al. |
| 2015/0173943 A1 | 6/2015 | Loomas et al. |
| 2015/0182282 A1 | 7/2015 | Zemel et al. |
| 2015/0182560 A1 | 7/2015 | Calle et al. |
| 2015/0201996 A1 | 7/2015 | Rubinsky et al. |
| 2015/0223879 A1 | 8/2015 | Danek et al. |
| 2015/0230855 A1 | 8/2015 | Chornenky et al. |
| 2015/0258352 A1 | 9/2015 | Lin et al. |
| 2015/0289923 A1 | 10/2015 | Davalos et al. |
| 2015/0305794 A9 | 10/2015 | Danek et al. |
| 2015/0313664 A1 | 11/2015 | Jarrard |
| 2015/0320478 A1 | 11/2015 | Cosman, Jr. et al. |
| 2015/0320479 A1 | 11/2015 | Cosman, Jr. et al. |
| 2015/0320999 A1 | 11/2015 | Nuccitelli et al. |
| 2015/0327944 A1 | 11/2015 | Neal, II et al. |
| 2015/0342669 A1 | 12/2015 | Flanagan et al. |
| 2016/0000499 A1 | 1/2016 | Lennox et al. |
| 2016/0008016 A1 | 1/2016 | Cioanta et al. |
| 2016/0008066 A1 | 1/2016 | Kaplan et al. |
| 2016/0022349 A1 | 1/2016 | Woloszko et al. |
| 2016/0030014 A1 | 2/2016 | McWeeney et al. |
| 2016/0030016 A1 | 2/2016 | McWeeney et al. |
| 2016/0038230 A1 | 2/2016 | Danek et al. |
| 2016/0058493 A1 | 3/2016 | Neal, II et al. |
| 2016/0066977 A1 | 3/2016 | Neal, II et al. |
| 2016/0066990 A1 | 3/2016 | Kaplan et al. |
| 2016/0074091 A1 | 3/2016 | Amoah et al. |
| 2016/0081745 A1 | 3/2016 | Rajagopalan et al. |
| 2016/0113703 A1 | 4/2016 | Danek et al. |
| 2016/0128767 A1 | 5/2016 | Azamian et al. |
| 2016/0166310 A1 | 6/2016 | Stewart et al. |
| 2016/0199131 A1 | 7/2016 | Allison et al. |
| 2016/0206370 A1 | 7/2016 | Fruland et al. |
| 2016/0235974 A1 | 8/2016 | Holochwost et al. |
| 2016/0262601 A1 | 9/2016 | Viebach et al. |
| 2016/0262795 A1 | 9/2016 | Urbanski et al. |
| 2016/0287314 A1 | 10/2016 | Arena et al. |
| 2016/0303293 A1 | 10/2016 | Doyle et al. |
| 2016/0310211 A1 | 10/2016 | Long |
| 2016/0324573 A1 | 11/2016 | Mickelson et al. |
| 2016/0331441 A1 | 11/2016 | Konings |
| 2016/0338758 A9 | 11/2016 | Davalos et al. |
| 2016/0354142 A1 | 12/2016 | Pearson et al. |
| 2016/0354145 A1 | 12/2016 | Stern et al. |
| 2016/0361109 A1 | 12/2016 | Weaver et al. |
| 2016/0367310 A1 | 12/2016 | Onik et al. |
| 2017/0000584 A1 | 1/2017 | Blanco et al. |
| 2017/0035499 A1 | 2/2017 | Stewart et al. |
| 2017/0049513 A1 | 2/2017 | Cosman, Jr. et al. |
| 2017/0065330 A1 | 3/2017 | Mickelson et al. |
| 2017/0065339 A1 | 3/2017 | Mickelson |
| 2017/0065340 A1 | 3/2017 | Long |
| 2017/0065343 A1 | 3/2017 | Mickelson |
| 2017/0087224 A1 | 3/2017 | Quake |
| 2017/0105763 A1 | 4/2017 | Karve et al. |
| 2017/0105793 A1 | 4/2017 | Cao et al. |
| 2017/0117603 A1 | 4/2017 | Kreis et al. |
| 2017/0119465 A1 | 5/2017 | Long et al. |
| 2017/0135723 A1 | 5/2017 | Zarembinski |
| 2017/0156783 A1 | 6/2017 | McKernon et al. |
| 2017/0189097 A1 | 7/2017 | Viswanathan et al. |
| 2017/0189579 A1 | 7/2017 | Davalos |
| 2017/0215939 A1 | 8/2017 | Palti et al. |
| 2017/0215953 A1 | 8/2017 | Long et al. |
| 2017/0216353 A1 | 8/2017 | Nuccitelli et al. |
| 2017/0216585 A1 | 8/2017 | Goldfarb et al. |
| 2017/0239480 A1 | 8/2017 | Zarins et al. |
| 2017/0246455 A1 | 8/2017 | Athos et al. |
| 2017/0252090 A1 | 9/2017 | Smith et al. |
| 2017/0266283 A1 | 9/2017 | Soikum et al. |
| 2017/0266438 A1 | 9/2017 | Sano et al. |
| 2017/0281934 A1 | 10/2017 | Giladi et al. |
| 2017/0304002 A1 | 10/2017 | Beebe et al. |
| 2017/0311789 A1 | 11/2017 | Mulcahey et al. |
| 2017/0312021 A1 | 11/2017 | Pilcher et al. |
| 2017/0319843 A1 | 11/2017 | Beebe et al. |
| 2017/0319851 A1 | 11/2017 | Athos et al. |
| 2017/0325894 A1 | 11/2017 | Krimsky |
| 2017/0326361 A1 | 11/2017 | Kreis et al. |
| 2017/0333104 A1 | 11/2017 | Forde et al. |
| 2017/0333109 A1 | 11/2017 | Gilbert |
| 2017/0333112 A1 | 11/2017 | Nuccitelli et al. |
| 2017/0360326 A1 | 12/2017 | Davalos et al. |
| 2018/0000895 A1 | 1/2018 | Pierce et al. |
| 2018/0001056 A1 | 1/2018 | Leeflang et al. |
| 2018/0008127 A1 | 1/2018 | Tinkham et al. |
| 2018/0014868 A1 | 1/2018 | O'Connor et al. |
| 2018/0028250 A1 | 2/2018 | O'Connor |
| 2018/0028267 A1 | 2/2018 | Onik et al. |
| 2018/0036058 A1 | 2/2018 | Fan et al. |
| 2018/0042655 A1 | 2/2018 | Burr et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0071014 A1 | 3/2018 | Neal et al. |
| 2018/0078755 A1 | 3/2018 | Kreis et al. |
| 2018/0085160 A1 | 3/2018 | Viswanathan et al. |
| 2018/0085575 A1 | 3/2018 | Travers et al. |
| 2018/0104486 A1 | 4/2018 | Yoon et al. |
| 2018/0110557 A1 | 4/2018 | Muratori et al. |
| 2018/0110978 A1 | 4/2018 | Beebe et al. |
| 2018/0125565 A1 | 5/2018 | Sano et al. |
| 2018/0132922 A1 | 5/2018 | Neal, II |
| 2018/0153937 A1 | 6/2018 | Nuccitelli et al. |
| 2018/0154142 A1 | 6/2018 | Guo et al. |
| 2018/0193082 A1 | 7/2018 | Rubinsky et al. |
| 2018/0193088 A1 | 7/2018 | Sutton et al. |
| 2018/0200510 A1 | 7/2018 | Nuccitelli et al. |
| 2018/0221078 A1 | 8/2018 | Howard et al. |
| 2018/0263685 A1 | 9/2018 | Onik et al. |
| 2018/0289954 A1 | 10/2018 | Hebb et al. |
| 2018/0303543 A1 | 10/2018 | Stewart et al. |
| 2018/0311497 A1 | 11/2018 | Viswanathan et al. |
| 2018/0344378 A1 | 12/2018 | Wolf et al. |
| 2018/0360531 A1 | 12/2018 | Holmes, Jr. et al. |
| 2019/0022333 A1 | 1/2019 | Baillargeon et al. |
| 2019/0030328 A1 | 1/2019 | Stewart et al. |
| 2019/0038895 A1 | 2/2019 | Pianca et al. |
| 2019/0046791 A1 | 2/2019 | Ebbers et al. |
| 2019/0059864 A1 | 2/2019 | Gonzalez |
| 2019/0069950 A1 | 3/2019 | Viswanathan et al. |
| 2019/0083169 A1 | 3/2019 | Single et al. |
| 2019/0099214 A1 | 4/2019 | Rubinsky et al. |
| 2019/0105408 A1 | 4/2019 | Heller et al. |
| 2019/0117963 A1 | 4/2019 | Travers et al. |
| 2019/0117969 A1 | 4/2019 | Schmidt et al. |
| 2019/0126037 A1 | 5/2019 | Ivorra Cano |
| 2019/0151015 A1 | 5/2019 | Viswanathan et al. |
| 2019/0160283 A1 | 5/2019 | Nuccitelli et al. |
| 2019/0201089 A1 | 7/2019 | Waldstreicher et al. |
| 2019/0216899 A1 | 7/2019 | Bright |
| 2019/0223938 A1 | 7/2019 | Arena et al. |
| 2019/0223943 A1 | 7/2019 | Forsyth et al. |
| 2019/0232048 A1 | 8/2019 | Latouche et al. |
| 2019/0239949 A1 | 8/2019 | Nuccitelli et al. |
| 2019/0254735 A1 | 8/2019 | Stewart et al. |
| 2019/0269826 A1 | 9/2019 | Peyman |
| 2019/0269912 A1 | 9/2019 | Viswanathan et al. |
| 2019/0275260 A1 | 9/2019 | Ralph et al. |
| 2019/0282294 A1 | 9/2019 | Davalos et al. |
| 2019/0299019 A1 | 10/2019 | Chornenky et al. |
| 2019/0307781 A1 | 10/2019 | Krex et al. |
| 2019/0328445 A1 | 10/2019 | Sano et al. |
| 2019/0350971 A1 | 11/2019 | Nuccitelli et al. |
| 2019/0351224 A1 | 11/2019 | Sano et al. |

(56) References Cited

U.S. PATENT DOCUMENTS

| | | | |
|---|---|---|---|
| 2019/0365362 A1 | 12/2019 | Ralph | |
| 2020/0000938 A1 | 1/2020 | Pierce et al. | |
| 2020/0009377 A1 | 1/2020 | Chang et al. | |
| 2020/0016067 A1 | 1/2020 | Gotlib et al. | |
| 2020/0038093 A1 | 2/2020 | Onik | |
| 2020/0046423 A1 | 2/2020 | Viswanathan et al. | |
| 2020/0046967 A1 | 2/2020 | Ivey et al. | |
| 2020/0060754 A1 | 2/2020 | Shuman et al. | |
| 2020/0060755 A1 | 2/2020 | Shuman et al. | |
| 2020/0078047 A1 | 3/2020 | Lambe et al. | |
| 2020/0129228 A1 | 4/2020 | Henkes et al. | |
| 2020/0260987 A1 | 8/2020 | Davalos et al. | |
| 2020/0275973 A1 | 9/2020 | O'Brien et al. | |
| 2020/0298008 A1 | 9/2020 | Asirvatham | |
| 2020/0398048 A1 | 12/2020 | Krimsky et al. | |
| 2021/0022794 A1 | 1/2021 | Viswanathan | |
| 2021/0023362 A1 | 1/2021 | Lorenzo et al. | |
| 2021/0038280 A1 | 2/2021 | Pikramenos | |
| 2021/0137410 A1 | 5/2021 | O'Brien et al. | |
| 2021/0146126 A1 | 5/2021 | Waldstreicher et al. | |
| 2021/0161582 A1 | 6/2021 | Byrd et al. | |
| 2021/0236815 A1 | 8/2021 | Waldstreicher et al. | |
| 2021/0236816 A1 | 8/2021 | Waldstreicher et al. | |
| 2021/0393327 A1* | 12/2021 | Eyster | A61B 18/1815 |
| 2022/0104875 A1 | 4/2022 | Gleiman et al. | |
| 2022/0161027 A1 | 5/2022 | Aycock et al. | |
| 2022/0233237 A1 | 7/2022 | Adams et al. | |
| 2022/0249157 A1 | 8/2022 | Viswanathan et al. | |
| 2022/0330886 A1 | 10/2022 | Varadan et al. | |
| 2022/0387095 A1* | 12/2022 | Neal, II | A61B 18/1492 |
| 2022/0395323 A1 | 12/2022 | Waldstreicher et al. | |
| 2023/0082389 A1 | 3/2023 | Waldstreicher et al. | |
| 2023/0149706 A1 | 5/2023 | Krimsky et al. | |
| 2023/0165629 A1 | 6/2023 | Tehrani et al. | |
| 2023/0172650 A1 | 6/2023 | Castellvi et al. | |
| 2023/0240746 A1 | 8/2023 | Gundert et al. | |
| 2023/0248414 A1 | 8/2023 | Sano et al. | |
| 2023/0405313 A1 | 12/2023 | Pastori et al. | |
| 2024/0032984 A1 | 2/2024 | Castellvi et al. | |
| 2024/0173557 A1 | 5/2024 | Neal, II et al. | |
| 2024/0180878 A1 | 6/2024 | Spera | |
| 2024/0277245 A1 | 8/2024 | Davalos et al. | |
| 2024/0350185 A1 | 10/2024 | O'Brien et al. | |
| 2024/0350187 A1 | 10/2024 | Waldstreicher et al. | |
| 2024/0390672 A1 | 11/2024 | Neal et al. | |
| 2025/0032787 A1 | 1/2025 | Krimsky et al. | |
| 2025/0064510 A1 | 2/2025 | Waldstreicher et al. | |
| 2025/0213299 A1 | 7/2025 | Nafie et al. | |

FOREIGN PATENT DOCUMENTS

| | | |
|---|---|---|
| AU | 2004235684 A1 | 1/2005 |
| AU | 2015355241 A1 | 6/2017 |
| AU | 2016246146 A1 | 10/2017 |
| AU | 2020200688 B2 | 7/2021 |
| CA | 2370223 A1 | 10/2000 |
| CA | 2981867 A1 | 10/2016 |
| CN | 1867299 A | 11/2006 |
| CN | 101198287 A | 6/2008 |
| CN | 101426551 A | 5/2009 |
| CN | 101553180 A | 10/2009 |
| CN | 101909649 A | 12/2010 |
| CN | 102014779 A | 4/2011 |
| CN | 102105115 A | 6/2011 |
| CN | 102421386 A | 4/2012 |
| CN | 102725021 A | 10/2012 |
| CN | 103027745 A | 4/2013 |
| CN | 103252016 A | 8/2013 |
| CN | 103281978 A | 9/2013 |
| CN | 103313671 A | 9/2013 |
| CN | 103582463 A | 2/2014 |
| CN | 103750899 A | 4/2014 |
| CN | 103781433 A | 5/2014 |
| CN | 103796603 A | 5/2014 |
| CN | 104080418 A | 10/2014 |
| CN | 104363849 A | 2/2015 |
| CN | 104470454 A | 3/2015 |
| CN | 104602634 A | 5/2015 |
| CN | 104602754 A | 5/2015 |
| CN | 104703557 A | 6/2015 |
| CN | 105073051 A | 11/2015 |
| CN | 105939686 A | 9/2016 |
| CN | 107194119 A | 9/2017 |
| CN | 107205772 A | 9/2017 |
| CN | 107921258 A | 4/2018 |
| CN | 108024803 A | 5/2018 |
| CN | 108778172 A | 11/2018 |
| CN | 108778173 A | 11/2018 |
| CN | 109788979 A | 5/2019 |
| CN | 110573104 A | 12/2019 |
| CN | 113558744 A | 10/2021 |
| CO | 2017010662 A2 | 3/2018 |
| DE | 60023283 T2 | 7/2006 |
| DK | 0987989 T3 | 10/2006 |
| EP | 1173103 A2 | 1/2002 |
| EP | 0935482 B1 | 5/2005 |
| EP | 1173103 B1 | 10/2005 |
| EP | 1804905 A1 | 7/2007 |
| EP | 1991303 A2 | 11/2008 |
| EP | 2170198 A1 | 4/2010 |
| EP | 2317951 A1 | 5/2011 |
| EP | 2413833 A1 | 2/2012 |
| EP | 2488251 A2 | 8/2012 |
| EP | 2642937 A2 | 10/2013 |
| EP | 2661236 A1 | 11/2013 |
| EP | 2736432 A1 | 6/2014 |
| EP | 2762195 A2 | 8/2014 |
| EP | 2777579 A1 | 9/2014 |
| EP | 2170198 B1 | 4/2015 |
| EP | 1648555 B1 | 9/2015 |
| EP | 2957248 A1 | 12/2015 |
| EP | 1804905 B1 | 2/2016 |
| EP | 2736432 B1 | 3/2016 |
| EP | 3003461 A2 | 4/2016 |
| EP | 2661236 B1 | 8/2016 |
| EP | 3091925 A1 | 11/2016 |
| EP | 3113605 A1 | 1/2017 |
| EP | 3142584 A1 | 3/2017 |
| EP | 3143124 A1 | 3/2017 |
| EP | 3154464 A1 | 4/2017 |
| EP | 3003470 B1 | 8/2017 |
| EP | 3226794 A1 | 10/2017 |
| EP | 3282953 A1 | 2/2018 |
| EP | 3290082 A2 | 3/2018 |
| EP | 3139997 B1 | 9/2018 |
| EP | 3113605 B1 | 10/2018 |
| EP | 3399931 A1 | 11/2018 |
| EP | 3399933 A1 | 11/2018 |
| EP | 3154463 B1 | 3/2019 |
| EP | 3471631 A1 | 4/2019 |
| EP | 2994045 B1 | 5/2019 |
| EP | 3003461 B1 | 5/2019 |
| EP | 3091921 B1 | 6/2019 |
| EP | 3456278 A3 | 6/2019 |
| EP | 3495018 A1 | 6/2019 |
| EP | 3206613 B1 | 7/2019 |
| EP | 3569144 A1 | 11/2019 |
| ES | 2246853 T3 | 3/2006 |
| ES | 2361460 T3 | 6/2011 |
| IN | 200601622 | 5/2007 |
| JP | H09285182 A | 10/1997 |
| JP | 2001103741 A | 4/2001 |
| JP | 2001506157 A | 5/2001 |
| JP | 2002065626 A | 3/2002 |
| JP | 2002541905 A | 12/2002 |
| JP | 2003529401 A | 10/2003 |
| JP | 2004516867 A | 6/2004 |
| JP | 2006320176 A | 11/2006 |
| JP | 2007504910 A | 3/2007 |
| JP | 4242436 B2 | 3/2009 |
| JP | 4243436 B2 | 3/2009 |
| JP | 2010509032 A | 3/2010 |
| JP | 2011519699 A | 7/2011 |
| JP | 2011524785 A | 9/2011 |

(56) References Cited

FOREIGN PATENT DOCUMENTS

| | | | |
|---|---|---|---|
| JP | 2012515018 A | 7/2012 |
| JP | 2013543745 A | 12/2013 |
| JP | 2015128596 A | 7/2015 |
| JP | 2015524732 A | 8/2015 |
| JP | 2016195826 A | 11/2016 |
| JP | 2017518805 A | 7/2017 |
| JP | 2017529169 A | 10/2017 |
| JP | 2019500170 A | 1/2019 |
| JP | 2019524396 A | 9/2019 |
| JP | 2020518335 A | 6/2020 |
| JP | 2021500153 A | 1/2021 |
| JP | 2023536906 A | 8/2023 |
| PT | 987989 E | 11/2006 |
| WO | WO-9814238 A1 | 4/1998 |
| WO | WO-9906101 A1 | 2/1999 |
| WO | WO-2000062699 A2 | 10/2000 |
| WO | WO-0110319 A1 | 2/2001 |
| WO | WO-2001055294 A1 | 8/2001 |
| WO | WO-2002032333 A1 | 4/2002 |
| WO | WO-02098501 A2 | 12/2002 |
| WO | WO-03047684 A2 | 6/2003 |
| WO | WO-2004037341 A2 | 5/2004 |
| WO | WO-2004110371 A2 | 12/2004 |
| WO | WO-2005044371 A1 | 5/2005 |
| WO | WO-2005065284 A2 | 7/2005 |
| WO | WO-2005115535 A2 | 12/2005 |
| WO | WO-2005032646 A3 | 4/2006 |
| WO | WO-2006036706 A1 | 4/2006 |
| WO | WO-2006052940 A2 | 5/2006 |
| WO | WO-2006085150 A2 | 8/2006 |
| WO | WO-2006116198 A2 | 11/2006 |
| WO | WO-2006116608 A2 | 11/2006 |
| WO | WO-2006131816 A2 | 12/2006 |
| WO | WO-2007001747 A2 | 1/2007 |
| WO | WO-2007001751 A1 | 1/2007 |
| WO | WO-2007039799 A3 | 7/2007 |
| WO | WO-2007100727 A2 | 9/2007 |
| WO | WO-2007103070 A2 | 9/2007 |
| WO | WO-2008034100 A2 | 3/2008 |
| WO | WO-2008063195 A1 | 5/2008 |
| WO | WO-2008087489 A2 | 7/2008 |
| WO | WO-2009009398 A1 | 1/2009 |
| WO | WO-2009137800 A2 | 11/2009 |
| WO | WO-2009137819 A1 | 11/2009 |
| WO | WO-2009154654 A1 | 12/2009 |
| WO | WO-2010014480 A1 | 2/2010 |
| WO | WO-2010022275 A1 | 2/2010 |
| WO | WO-2010080974 A1 | 7/2010 |
| WO | WO-2010093692 A2 | 8/2010 |
| WO | WO-2010107947 A1 | 9/2010 |
| WO | WO-2010117806 A1 | 10/2010 |
| WO | WO-2010118387 A1 | 10/2010 |
| WO | WO-2010141417 A2 | 12/2010 |
| WO | WO-2010151277 A1 | 12/2010 |
| WO | WO-2011047387 A2 | 4/2011 |
| WO | WO-2011135294 A1 | 11/2011 |
| WO | WO-2012071526 A2 | 5/2012 |
| WO | WO-2012088149 A2 | 6/2012 |
| WO | WO-2012118659 A1 | 9/2012 |
| WO | WO-2013052501 A1 | 4/2013 |
| WO | WO-2014025394 A1 | 2/2014 |
| WO | WO-2014105964 A1 | 7/2014 |
| WO | WO-2014181167 A1 | 11/2014 |
| WO | WO-2014197240 A2 | 12/2014 |
| WO | WO-2014197632 A2 | 12/2014 |
| WO | WO-2014204978 A1 | 12/2014 |
| WO | WO-2015085162 A1 | 6/2015 |
| WO | WO-2015103530 A1 | 7/2015 |
| WO | WO-2015103574 A1 | 7/2015 |
| WO | WO-2015171921 A2 | 11/2015 |
| WO | WO-2015175570 A1 | 11/2015 |
| WO | WO-2015192018 A1 | 12/2015 |
| WO | WO-2015192027 A1 | 12/2015 |
| WO | WO-2016014264 A1 | 1/2016 |
| WO | WO-2016036891 A1 | 3/2016 |

| | | | | |
|---|---|---|---|---|
| WO | WO-2016060983 A1 | 4/2016 |
| WO | WO-2016061002 A1 | 4/2016 |
| WO | WO-2016089781 A1 | 6/2016 |
| WO | WO-2016100325 A1 | 6/2016 |
| WO | WO-2016112359 A1 | 7/2016 |
| WO | WO-2016123608 A2 | 8/2016 |
| WO | WO-2016126778 A1 | 8/2016 |
| WO | WO-2016149575 A1 | 9/2016 |
| WO | WO-2016154473 A1 | 9/2016 |
| WO | WO-2016164930 A1 | 10/2016 |
| WO | WO-2016178697 A1 | 11/2016 |
| WO | WO-2016179712 A1 | 11/2016 |
| WO | WO-2016180934 A1 | 11/2016 |
| WO | WO-2016201264 A1 | 12/2016 |
| WO | WO-2017024123 A1 | 2/2017 |
| WO | WO-2017109261 A1 | 6/2017 |
| WO | WO-2017114001 A1 | 7/2017 |
| WO | WO-2017119934 A1 | 7/2017 |
| WO | WO-2017120169 A1 | 7/2017 |
| WO | WO-2017151260 A1 | 9/2017 |
| WO | WO-2017173089 A1 | 10/2017 |
| WO | WO-2017175116 A1 | 10/2017 |
| WO | WO-2017200954 A1 | 11/2017 |
| WO | WO-2017201394 A1 | 11/2017 |
| WO | WO-2017218734 A1 | 12/2017 |
| WO | WO-2018005511 A1 | 1/2018 |
| WO | WO-2018010659 A1 | 1/2018 |
| WO | WO-2018026985 A1 | 2/2018 |
| WO | WO-2018065806 A1 | 4/2018 |
| WO | WO-2018067999 A1 | 4/2018 |
| WO | WO-2018075946 A1 | 4/2018 |
| WO | WO-2018106672 A1 | 6/2018 |
| WO | WO-2018187244 A2 | 10/2018 |
| WO | WO-2018200800 A1 | 11/2018 |
| WO | WO-2018201037 A1 | 11/2018 |
| WO | WO-2019032474 A1 | 2/2019 |
| WO | WO-2019055512 A1 | 3/2019 |
| WO | WO-2019084011 A1 | 5/2019 |
| WO | WO-2019095604 A1 | 5/2019 |
| WO | WO-2019100016 A1 | 5/2019 |
| WO | WO-2019108540 A1 | 6/2019 |
| WO | WO-2019133606 A1 | 7/2019 |
| WO | WO-2019133608 A1 * | 7/2019 | ............ A61B 18/00 |
| WO | WO-2019157359 A1 | 8/2019 |
| WO | WO-2019178500 A1 | 9/2019 |
| WO | WO-2019197973 A1 | 10/2019 |
| WO | WO-2020010188 A1 | 1/2020 |
| WO | WO-2020018662 A1 | 1/2020 |
| WO | WO-2020061192 A1 | 3/2020 |
| WO | WO-2020118383 A1 | 6/2020 |
| WO | WO-2020150709 A1 | 7/2020 |
| WO | WO-2020215007 A1 | 10/2020 |
| WO | WO-2021011733 | 1/2021 |
| WO | WO-2021108292 A1 | 6/2021 |
| WO | WO-2021127558 A1 | 6/2021 |
| WO | WO-2021207385 A1 | 10/2021 |
| WO | WO-2022031797 A1 | 2/2022 |
| WO | WO-2022204479 A1 | 9/2022 |
| WO | WO-2022260723 A1 | 12/2022 |
| WO | WO-2022261418 A1 | 12/2022 |
| WO | WO-2023044124 A1 | 3/2023 |
| WO | WO-2023172773 A1 | 9/2023 |
| WO | WO-2023212250 A1 | 11/2023 |
| WO | WO-2023220419 A1 | 11/2023 |

OTHER PUBLICATIONS

A. Valipour et Al. Bronchial Rheoplasty Treatment for Chronic Bronchitis Using the Rheox System, 2020 American Thoracic Society, Abstract, Aug. 5, 2020.
A. Valipour, et Al. *First-in-Human Results of Bronchial Rheoplasty: An Endobronchial Treatment for Chronic Bronchitis (CB)*, Epidemiology and Therapy, Mini Symposium, May 22, 2019, Abstract.
Appelbaum et al., US Findings after Irreversible Electroporation Ablation: Radiologic-Pathologic Correlation, Radiology: vol. 262: No. 1—Jan. 2012.

(56) References Cited

OTHER PUBLICATIONS

Arschang Valipour et al. *Bronchial Rheoplasty for Treatment of Chronic Bronchitis*, American Journal of Respiratory and Critical Care Medicine, vol. 202, No. 5, Sep. 1, 2020, pp. 681-689.

Arschang Valipour et al. Bronchial Rheoplasty for Treatment of Chronic Bronchitis. Twelve-Month Results from a Multicenter Clinical Trial, American Journal of Respiratory and Critical Care Medicine, vol. 202, Issue 5, 2019.

Arschang Valipour, et al. Late Breaking Abstract—Bronchial Rheoplasty for Treatment of Chronic Bronchitis: 6 Month Results from a Prospective Multi-Center Study, Abstract, European Respiratory Journal 2019, pp. 1-5.

Charalambous et al., The Efficacy and Safety of the Open Approach Irreversible Electroporation in the Treatment of Pancreatic Cancer: A Systematic Review, European Journal of Surgical Oncology; vol. 46, No. 9, Sep. 2020.

Co-pending U.S. Appl. No. 18/416,505, inventor Neal; Robert E., filed Jan. 18, 2024.

Co-pending U.S. Appl. No. 18/423,043, inventor Krimsky; William Sanford, filed Jan. 25, 2024.

Davalos et al., Implications and Considerations of Thermal Effects When Applying Irreversible Electroporation Tissue Ablation Therapy, Prostate; vol. 75, No. 10; pp. 1114-1118, Jul. 1, 2015.

Edd et al., In Vivo Results of a New Focal Tissue Ablation Technique: Irreversible Electroporation, IEEE Transactions On Biomedical Engineering, vol. 53, No. 5; pp. 1409-1415; Jun. 2006.

EP18836576.1 Search Report dated Jun. 8, 2021.

EP20792123.0 Extended and Supplementary European Search Report dated Dec. 21, 2022.

EP23178276.4 Extended European Search Report dated Jun. 26, 2023.

Frandsen et al., Calcium electroporation Q4 in three cell lines; a comparison of bleomycin 2 and calcium, calcium compounds, and pulsing conditions, Biochimica et Biophysica Acta, vol. 1840, No. 3; pp. 1204-1208, Mar. 2014.

International Preliminary Report on Patentability for PCT/US2018/067501 dated Jun. 30, 2020.

International Search Report and Written Opinion for PCT/US2018/067504 on Jun. 30, 2020.

International Search Report and Written Opinion for PCT/US2020/028844 on Sep. 4, 2020.

Kundalia et al., Margin Accentuation for resectable Pancreatic cancer using Irreversible Electroporation e Results from the MACPIE-I study, European Journal of Surgical Oncology, vol. 47, No. 10: pp. 2571-2578; Oct. 2021.

"Lu, et al., "Sequence-Modified Antibiotic Resistance Genes Provide Sustained Plasmid-Mediated Transgene Expression in Mammals" (2017) Molecular Therapy, vol. 25, No. 5, pp. 1187-1198".

Maor et al., Irreversible Electroporation Attenuates Neointimal Formation After Angioplasty, IEEE Transactions on Biomedical Engineering, vol. 55, No. 9, Sep. 2008.

Maor et al., The Effect of Irreversible Electroporation on Blood Vessels, Technology in Cancer Research and Treatment, vol. 6, No. 4, Aug. 2007.

Pallav L Shah, et al. *Epithelial Resurfacing: The Bronchial Skin Peel, American Thoracic Society*, May 22, 2020, pp. 1-8.

PCT/US2018/067501 International Search Report and Written Opinion dated Mar. 13, 2019.

PCT/US2022/015217 International Search Report and Written Opinion dated May 6, 2022.

PCT/US2022/021888 International Search Report and Written Opinion dated Jun. 16, 2022.

Reddy et al., Pulsed Field Ablation of Paroxysmal Atrial Fibrillation, JACC Clin Electrophysiology vol. 7 No. 5, pp. 614-627, May 2021.

Rubinsky et al., "Irreversible Electroporation: a New Ablation Modality—Clinical Implications," Tech. Cancer Res. Treatment 6:1-12 (2007).

S. Fernandez-Bussy, et Al. *Histopathologic Results Post Bronchial Rheoplasty*, Epidemiology and Therapy, Mini Symposium, May 22, 2019, Abstract.

Timmer et al., Irreversible Electroporation for Locally Advanced Pancreatic Cancer, Techniques in Vascular and Interventional Radiology vol. 23, Issue 2, Jun. 2020.

U.S. Appl. No. 16/914,072 Notice of Allowance dated Jun. 20, 2022.

U.S. Appl. No. 17/214,688 Notice of Allowance dated Feb. 4, 2022.

U.S. Appl. No. 17/214,688 Notice of Allowance dated Mar. 2, 2022.

U.S. Appl. No. 16/914,200 Notice of Allowance dated Sep. 8, 2022.

U.S. Appl. No. 16/914,200 Office Action dated May 4, 2022.

U.S. Appl. No. 16/914,200 Office Action dated Oct. 22, 2021.

U.S. Appl. No. 17/214,688 Office Action dated Sep. 7, 2021.

U.S. Appl. No. 17/502,640 Office Action dated Apr. 28, 2023.

U.S. Appl. No. 17/502,640 Office Action dated Jul. 13, 2022.

U.S. Appl. No. 17/502,640 Office Action dated Mar. 14, 2022.

U.S. Appl. No. 17/502,640 Office Action dated Nov. 27, 2023.

U.S. Appl. No. 18/077,097 Corrected Notice of Allowability dated Dec. 26, 2023.

U.S. Appl. No. 18/077,097 Notice of Allowance dated Oct. 27, 2023.

U.S. Appl. No. 18/077,097 Office Action dated Aug. 3, 2023.

U.S. Appl. No. 17/214,688 Office Action dated May 25, 2021.

U.S. Appl. No. 16/914,072 Office Action dated Nov. 26, 2021.

V. Kim et al. *Bronchial Rheoplasty Increases Distal Airway vol. in Chronic Bronchitis*, European Respiratory Journal 2019, vol. 54, Suppl. 63, PA2040 Abstract.

Valipour, A., Ing, A., Williamson, J., et al. *Late Breaking Abstract—First-in-Human Results of Bronchial Rheoplasty: An Endobronchial Treatment for Chronic Bronchitis (CB)*. European Respiratory Journal 2018 52: Suppl. 62, OA2162.

Verma et al., Primer on Pulsed Electrical Field Ablation: Understanding the Benefits and Limitations, Circulation: Arrhythmia and Electrophysiology, vol. 14, No. 9, Sep. 20, 2021.

Xie et al., Ablation of Myocardial Tissue With Nanosecond Pulsed Electric Fields, Plos One, vol. 10, No. 12, Dec. 14, 2015.

Yavin et al., Pulsed Field Ablation Using a Lattice Electrode for Focal Energy Delivery, Circulation: Arrhythmia and Electrophysiology, vol. 13, No. 6, May 6, 2020.

PCT/US2021/026221 International Search Report and Written Opinion dated Jul. 21, 2021.

Al-Sakere, et al., Tumor Ablation with Irreversible Electroporation, *PLoS One*, 2(11):e1135. doi:10.1371/journal.pone.0001135 (Nov. 2007).

Arena C.B., et al., "Chapter 10.13: Electroporation Therapy," Comprehensive Biomedical Physics, Springer, Editor: A. Brahme, 2014, vol. 10, pp. 269-287 (20 Pages), Retrieved from URL: http://dx.doi.org/10.1016/8978-0-444-53632-7.01016-9.

Arena C.B., et al., "High-frequency Irreversible Electroporation (H-FIRE) for Non-thermal Ablation without Muscle Contraction," Biomedical Engineering Online, Nov. 21, 2011, vol. 10, Article No. 102, pp. 1-20 (21 Pages).

Arena, et al., High-frequency irreversible electroporation (H-FIRE) for non-thermal ablation without muscle contraction, *BioMedical Engineering OnLine*, 10:102, http://www.biomedical-engineering-online.com/content/10/1/102 (Nov. 2011).

Bertacchini, et al., Design of an Irreversible Electroporation System for Clinical Use, *Technology in Cancer Research and Treatment*, 6(4):313-320 (Aug. 2007).

Bhonsle S., et al., "Characterization of Irreversible Electroporation Ablation with a Validated Perfused Organ Model," Journal of Vascular and Interventional Radiology, 2016, vol. 27, pp. 1913-1922 (12 Pages), Appendix A—Supplemental Materials and Methods.

Campelo S., et al., "An Evaluation of Irreversible Electroporation Thresholds in Human Prostate Cancer and Potential Correlations to Physiological Measurements," APL Bioengineering, 2017, vol. 1 (016101), pp. 016101-1-016101-10, Retrieved from URL: https://doi.org/10.1063/1.5005828.

Cerveri I., et al., "Variations in the Prevalence Across Countries of Chronic Bronchitis and Smoking Habits in Young Adults," The European Respiratory Journal, 2001, vol. 18, No. 1, pp. 85-92.

(56) References Cited

OTHER PUBLICATIONS

Cheetham J., et al., "Effects of Functional Electrical Stimulation on Denervated Laryngeal Muscle in a Large Animal Model," Artificial Organs, 2015, vol. 39, No. 10, pp. 876-885.

Criner G.G., "Chronic Bronchitis: The Case for an Unmet Medical Need," European Respiratory Society (ERS), 2017, 13 Pages.

Davalos, et al., Tissue Ablation with Irreversible Electroporation, Annals of Biomedical Engineering, 33(2):223-231 (Feb. 2005).

Dean D.A., "Gene Electrotransfer to Lung," Clinical Aspects of Electroporation, Springer Science Business Media, LLC, Chapter 15, 2011, pp. 165-175.

Dev, et al., Medical Applications of Electroporation, IEEE Transactions on Plasma Science, 28(1):206-223 (Feb. 2000).

Dupuy D.E., et al., "Irreversible Electroporation in a Swine Lung Model," Cardiovascular and Interventional Radiology, 2011, vol. 34, No. 2, pp. 391-395.

Edd, et al., In Vivo Results of a New Focal Tissue Ablation Technique: Irreversible Electroporation, *IEEE Transactions On Biomedical Engineering*, 53(5):1409-1415 (Jun. 2006).

Eurostat Statistics Database: "Health at a Glance: Europe (2012 and 2014 Reports)," Dec. 3, 2014, 41 Pages, Retrieved from URL: http://www.oecd-ilibrary.org/social-issues-migration-health/health-at-a-glance-europe-2012_978926418.

Extended European Search Report for European Application No. 20840607.4, dated Jun. 27, 2023, 08 Pages.

Extended European Search Report for European Application No. 21853941.9, dated Jul. 23, 2024, 07 Pages.

Extended European Search Report for European Application No. 22210537.1, dated Apr. 26, 2023, 11 Pages.

Extended European Search Report for European Application No. 22820712.2, dated Apr. 7, 2025, 08 Pages.

Extended European Search Report for European Application No. 22821096.9, dated Aug. 6, 2025, 13 Pages.

Extended European Search Report for European Application No. 23174654.6, dated Jun. 23, 2023, 07 Pages.

Extended European Search Report for European Application No. 25166670.7, dated May 15, 2025, 8 Pages.

Extended European Search Report for European Application No. 25184327.2, dated Jul. 15, 2025, 08 Pages.

Extended European Search Report for European Application No. EP22776703.5, dated Dec. 23, 2024, 8 Pages.

Extended European Search Report for European Application No. EP22870831.9, dated Jun. 16, 2025, 10 Pages.

Faststats-Chronic Lower Respiratory Disease: "Chronic Obstructive Pulmonary Disease (COPD) Includes: Chronic Bronchitis and Emphysema," Centers for Disease Control and Prevention (CDC)/National Center for Health Statistics (NCHS), Jan. 16, 2021, pp. 1-2, [Retrieved on Feb. 4, 2021] Retrieved from URL: https://www.cdc.gov/nchs/fastats/copd.htm.

Fernandez-Bussy S., et al., "Histopathologic Results Post Bronchial Rheoplasty," American Thoracic Society, 2019, 17 Pages.

Garcia P.A., et al., "A Parametric Study Delineating Irreversible Electroporation from Thermal Damage Based on a Minimally Invasive Intracranial Procedure," BioMedical Engineering OnLine, Apr. 30, 2011, vol. 10, Article No. 34, 22 Pages, Retrieved from URL: http://www.biomedical-engineering-online.com/content/10/1/34.

Garcia P.A., et al., "An Experimental Investigation of Temperature Changes During Electroporation," URSI General Assembly and Scientific Symposium, Istanbul, Turkey, Aug. 13-20, 2011, 4 Pages.

Garcia P.A., et al., "Intracranial Nonthermal Irreversible Electroporation: In Vivo Analysis," The Journal of Membrane Biology, 2010, vol. 236, pp. 127-136.

Garcia P.A., et al., "Non-Thermal Irreversible Electroporation for Tissue Ablation," Chapter 3, Electroporation in Laboratory and Clinical Investigations, Editors: E. P. Spugnini and al Baldi, 2010, 22 Pages.

Global Strategy for the Diagnosis, Management, and Prevention of COPD: "Global Initiative for Chronic Obstructive Lung Disease," 2017, pp. 1-42.

International Search Report and Written Opinion for International Application No. PCT/US2017/039527, dated Dec. 7, 2017, 22 Pages.

International Search Report and Written Opinion for International Application No. PCT/US2018/067504, dated Mar. 13, 2019, 13 Pages.

International Search Report and Written Opinion for International Application No. PCT/US2020/042260, dated Oct. 14, 2020, 12 Pages.

International Search Report and Written Opinion for International Application No. PCT/US2021/030911, dated Aug. 16, 2021, 10 Pages.

International Search Report and Written Opinion for International Application No. PCT/US2021/044469, dated Nov. 8, 2021, 17 Pages.

International Search Report and Written Opinion for International Application No. PCT/US2022/032981, dated Aug. 29, 2022, 15 Pages.

International Search Report and Written Opinion for International Application No. PCT/US2022/044021, dated Jan. 11, 2023, 11 Pages.

International Search Report and Written Opinion for International Application No. PCT/US2023/020282, dated Jul. 21, 2023, 14 Pages.

International Search Report and Written Opinion for International Application No. PCT/US2023/022109, dated Aug. 15, 2023, 10 Pages.

International Search Report and Written Opinion for International Application No. PCT/US2023/060897, dated Jul. 7, 2023, 15 Pages.

International Search Report and Written Opinion for International Application No. PCT/US2024/020309, dated Jul. 29, 2024, 10 Pages.

International Search Report and Written Opinion for International Application No. PCT/US2024/043295, dated Oct. 30, 2024, 9 Pages.

Jourabchi, et al., Irreversible Electroporation (NanoKnife) in Cancer Treatment, *Gastrointestinal Intervention*, 3:8-18 (Feb. 2014).

Kim H.B., et al., "Physicochemical Factors That Affect Electroporation of Lung Cancer and Normal Cell Lines," Biochemical and Biophysical Research Communications, 2019, vol. 517, No. 4, pp. 703-708.

Kim V., et al., "The Chronic Bronchitic Phenotype of COPD: An Analysis of the COPD Gene Study," Chest, Sep. 2011, vol. 140, No. 3, pp. 626-633.

Krassowska, et al., Viability of Cancer Cells Exposed to Pulsed Electric Fields: The Role of Pulse Charge, *Annals of Biomedical Engineering*, 31:80-90 (2003).

Mercadal, et al., Avoiding nerve stimulation in irreversible electroporation: a numerical modeling study, *Phys. Med. Biol.*, 62(20):8060-8079 (Oct. 2004).

Miklavcic, et al., A validated model of in vitro electric field distribution in tissues for electrochemotherapy and for DNA electrotransfer for gene therapy, *Biochimica et Biophysica Acta*, 1523:73-83 (2000).

Miklavcic, et al., The effect of high frequency electric pulses on muscle contractions and antitumor efficiency in vivo for a potential use in clinical electrochemotherapy, *Bioelectrochemistry*, 65:121-128 (2005).

Miklovic T., et al., "A Comprehensive Characterization of Parameters Affecting High-frequency Irreversible Electroporation Lesions," Annals of Biomedical Engineering, 2017, vol. 45, pp. 2524-2534 (11 Pages).

Miller, et al., Cancer Cells Ablation with Irreversible Electroporation, *Technology in Cancer Research & Treatment*, 4(6):699-705 (Dec. 2005).

Mir, et al., Mechanisms of electrochemotherapy, *Advanced Drug Delivery Reviews*, 35:107-118 (1999).

Napotnik, et al., Cell death due to electroporation—A Review, *Bioelectrochemistry*, 141:107871, pp. 1-18 (2021).

Neal II, R. E. et al., "The Feasibility of Irreversible Electroporation for the Treatment of Breast Cancer and Other Heterogeneous Systems," Annals of Biomedical Engineering, Dec. 2009, vol. 37, No. 12, pp. 2615-2625.

(56) References Cited

OTHER PUBLICATIONS

Neal II R.E., et al., "An "Off-the-Shelf" System for Intraprocedural Electrical Current Evaluation and Monitoring of Irreversible Electroporation Therapy," Cardio Vascular and Interventional Radiology, 2014, vol. 38, No. 3, pp. 736-741 (6 Pages).

Neal II R.E., et al., "Chapter 5.4: Clinical Implications of Irreversible Electroporation: Clinical and Preclinical Findings," Springer, Editors: H Akiyama and R Heller (In Press), 10 Pages.

Neal II R.E., et al., "Experimental Characterization and Numerical Modeling of Tissue Electrical Conductivity during Pulsed Electric Fields for Irreversible Electroporation Treatment Planning," IEEE Transactions on Biomedical Engineering, Apr. 2012, vol. 59, No. 4, pp. 1076-1085.

Neal II R.E., et al., "Hepatic Epithelioid Hemangioendothelioma Treated With Irreversible Electroporation and Antibiotics," Journal of Clinical Oncology, 2013, vol. 31, 5 Pages, Retrieved from URL: http://jco.ascopubs.org/cgl/dol/10.1200/JCO.2012.44.9736.

Neal II R.E., et al., "Improved Local and Systemic Anti-Tumor Efficacy for Irreversible Electroporation in Immunocompetent versus Immunodeficient Mice," PLOS One, May 24, 2013, vol. 8, No. 5 (e64559), 10 Pages, DOI:10.1371/journal.pone.0064559.

Neal II R.E., et al., "In Vitro and Numerical Support for Combinatorial Irreversible Electroporation and Electrochemotherapy Glioma Treatment," Annals of Biomedical Engineering, 2013, vol. 42, 13 Pages, DOI: 10.1007/s10439-013-0923-2.

Neal II R.E., et al., "In vivo Characterization and Numerical Simulation of Prostate Properties for Non-Thermal Irreversible Electroporation Ablation," The Prostate, 2014, vol. 17, No. 10 (22760), 11 Pages.

Neal II R.E., et al., "In Vivo Irreversible Electroporation Kidney Ablation: Experimentally Correlated Numerical Models," IEEE Transactions on Biomedical Engineering, 2013, 10 Pages, DOI: 10.1109/TBME.2014.2360374.

Neal II R.E., et al., "Spectrum of Imaging and Characteristics for Liver Tumors Treated With Irreversible Electroporation," Journal of Biomedical Science and Engineering, 2012, vol. 5, pp. 813-818.

Neal II R.E., et al., "The Effects of Metallic Implants on Electroporation Therapies: Feasibility of Irreversible Electroporation for Brachytherapy Salvage," CardioVascular and Interventional Radiology, 2013, vol. 36, No. 6, pp. 1638-1645 (08 Pages).

Neal II R.E., et al., "Treatment of Breast Cancer through the Application of Irreversible Electroporation Using a Novel Minimally Invasive Single Needle Electrode," Breast Cancer Research and Treatment, Aug. 2010, vol. 123, No. 1, pp. 295-301 (13 Pages).

Neal II R.E., et al., "Successful Treatment of a Large Soft Tissue Sarcoma with Irreversible Electroporation," Journal of Clinical Oncology, May 1, 2011, vol. 29, No. 13, pp. e372-e377, DOI: 10.1200/JCO.2010.33.0902.

Novickij V., et al., "High Frequency Electroporation Efficiency is Under Control of Membrane Capacitive Charging and Voltage Potential Relaxation," Bioelectrochemistry, 2018, vol. 119, pp. 92-97.

O'Brien T.J., et al., "Effects of Internal Electrode Cooling on Irreversible Electroporation Using a Perfused Organ Model," International Journal of Hyperthermia, 2019, vol. 35, No. 1, pp. 44-55 (12 Pages).

Ricke J., et al., "Irreversible Electroporation (IRE) Fails to Demonstrate Efficacy in a Prospective Multicenter Phase II Trial on Lung Malignancies: The ALICE Trial," Cardiovascular and Interventional Radiology, 2015, vol. 38, No. 2, pp. 401-408.

Rogers, et al., Strength-Duration Curve for an Electrically Excitable Tissue Extended Down to Near 1 Nanosecond, *IEEE Transactions on Plasma Science*, 32(4):1587-1599 (Aug. 2004).

Rossmeisl J.H., Jr., et al., "Safety and Feasibility of the Nanoknife System for Irreversible Electroporation Ablative Treatment of Canine Spontaneous Intracranial Gliomas," Journal of Neurosurgery, Jul. 3, 2015, vol. 123, No. 4, pp. 1008-1025 (18 Pages).

Sano M.B., et al., "Burst and Continuous High Frequency Irreversible Electroporation Protocols Evaluated in a 3D Tumor Model," Physics in Medicine and Biology, Jul. 6, 2018, vol. 63, No. 13 (135022), pp. 1-18.

Sano M.B., et al., "Towards the Creation of Decellularized Organ Constructs Using Irreversible Electroporation and Active Mechanical Perfusion," BioMedical Engineering OnLine, 2010, vol. 9, No. 83, 16 Pages, Retrieved from URL: http://www.biomedical-engineering-online.com/content/9/1/83.

Scheffer H.J., et al., "The Influence of a Metal Stent on the Distribution of Thermal Energy during Irreversible Electroporation," PLOS One, Feb. 4, 2016, vol. 11, No. 2 (e0148457), 13 Pages, DOI:10.1371/journal.pone.0148457.

Schoenbach K.H., et al., "Bioelectrics," Springer, Editors: H. Akiyama, R. Heller, 2017, 491 Pages, ISBN 978-4-431-56093-7, ISBN 978-4-431-56095-1 (eBook), DOI: 10.1007/978-4-431-56095-1.

Shah P.L., et al., "Epithelial Resurfacing: The Bronchial Skin Peel," American Journal of Respiratory and Critical Care Medicine, Sep. 1, 2020, Vo,. 202, No. 5, pp. 641-642.

Tang P.S., et al., "Acute Lung Injury and Cell Death: How Many Ways Can Cells Die," American Journal of Physiology Lung Cellular and Molecular Physiology, Jan. 18, 2008, vol. 294, No. 4, pp. L632-L641.

Thomson K.R., et al., "Introduction to Irreversible Electroporation-Principles and Techniques," Techniques in Vascular and Interventional Radiology, 2015, vol. 18, No. 3, pp. 128-134.

Tri J.A., et al., "Electroporation Ablation of Bronchial Smooth Muscle Cells: A Novel Non-thermal Asthma Therapy," Pulmonary and Critical Care Medicine, 2016, vol. 1, No. 4, pp. 1-4.

Valipour A., et al., "First-in-Human Results of Bronchial Rheoplasty: An endobronchial Treatment for Chronic Bronchitis (CB)," American Thoracic Society, 2019, pp. 1-20.

Vollmer, Robin T., Tumor Length In Prostate Cancer, *American Journal of Clinical Pathology*, 130(1):77-82 (Jul. 2008).

Wandel A., et al., "Optimizing Irreversible Electroporation Ablation with a Bipolar Electrode," The Journal of Vascular and Interventional Radiology, Sep. 2016, vol. 27, No. 9, pp. 1441-1450 (12 Pages).

* cited by examiner

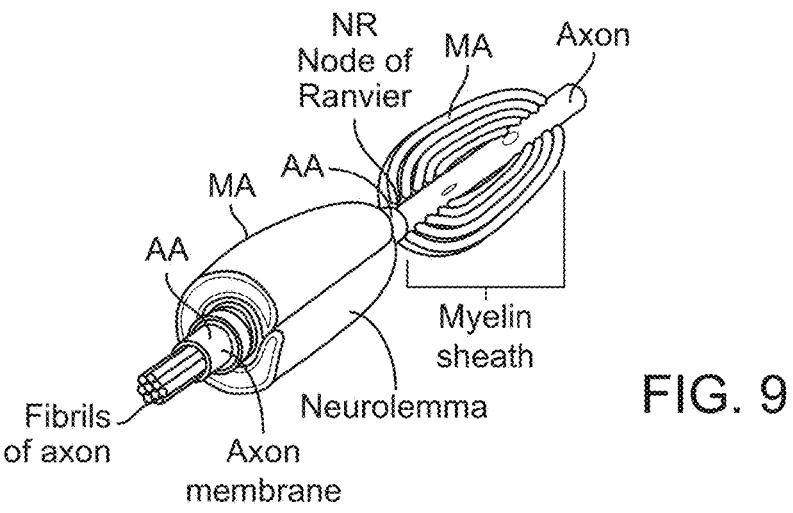
FIG. 9
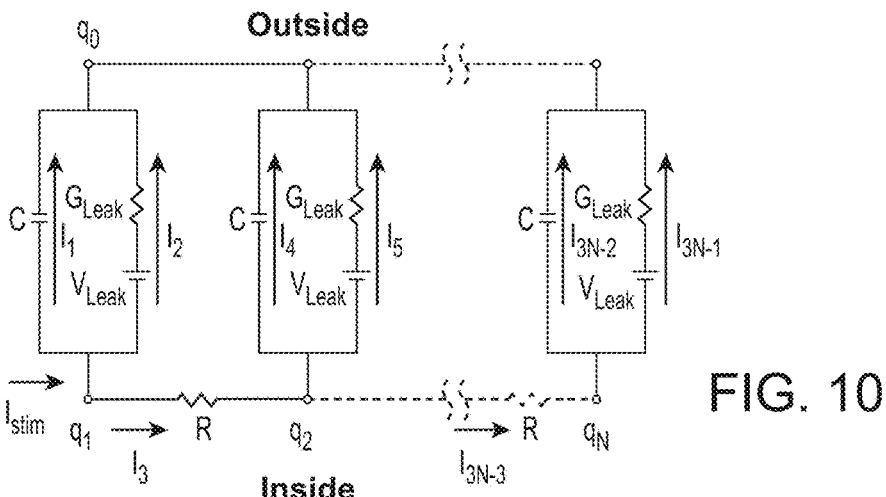
FIG. 10
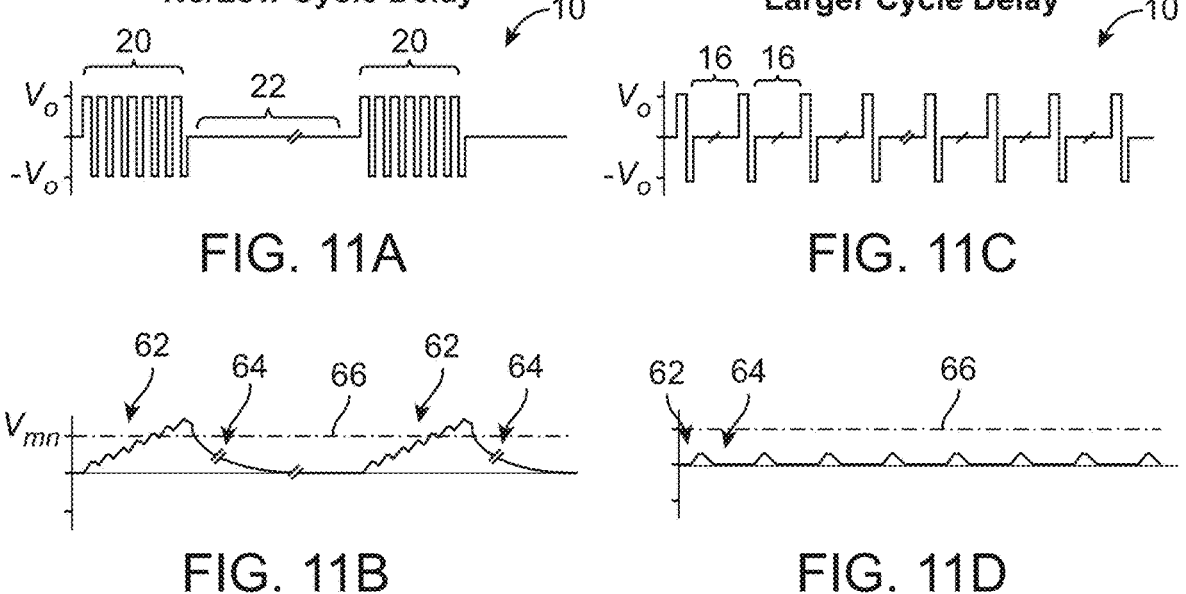
FIG. 11A
FIG. 11C
FIG. 11B
FIG. 11D Time=1.055E-4 (2) s Surface: Temperature (degC)

Time=0.0591 (8) s Surface: Temperature (degC)

Pulse Voltage Asymmetry : Ex 2500-1250-2500 V

Pulse Length Asymmetry : Ex 830-415-830ns

Pulse Asymmetry (pulse length and/or pulse voltage) :
Ex 2500V@830ns - 0 - 2500V@830ns
*Note: Because no opposing polarity, there is no appreciable difference when considering $t_s$ V. $t_d$*

Pulse Voltage and Timing Variable Asymmetry : Multiple combinations and permutations possible

PULSED ELECTRIC FIELD WAVEFORM MANIPULATION AND USE

CROSS-REFERENCE TO RELATED APPLICATIONS

This application is a continuation of PCT Application No. PCT/US2021/026221filed Apr. 7, 2021, which claims priority to and the benefit of U.S. Provisional Patent Application No. 63/007,233, filed Apr. 8, 2020, and U.S. Provisional Patent Application No. 63/078,784, filed Sep. 15, 2020, the entire content of each of which is fully incorporated herein by reference.

BACKGROUND OF THE INVENTION

Various devices and methods have been developed to deliver therapeutic energy to the body for the treatment of diseases and afflictions. In some instances, such delivery is to tissues within a body lumen, passageway or similar anatomy, so as to treat diseased tissue along or within the walls of the passageway, or so as to affect diseases which are associated with a passageway or reachable through a passageway. Such devices typically include a flexible elongate shaft, so as to traverse tortuous luminal anatomy, and an energy delivery element mounted thereon to deliver such energy to remote or enclosed locations such as body lumens. Such devices have been developed to treat, for example, passageways of the lungs or blood vessels of the vasculature.

A variety of different types of energy have been used for therapeutic treatments, including radiofrequency energy, microwave energy, high intensity focused ultrasound (HIFU) energy, and pulsed electric field (PEF) energy, to name a few. PEF energy typically delivers high-energy discharges over very short periods. Thus, low-voltage energy from a DC power supply is transformed to high-intensity pulsed fields. The high-intensity energy is stored in capacitors to be discharged to the target tissue at different electric strengths (20-80 kV cm-1) and times (<1 s).

PEF energy is delivered in a manner so as to be non-thermal (i.e. below a threshold for causing cell death by thermal injury). Consequently, when extracellular matrices are present, the extracellular matrices are preserved, and the targeted tissue maintains its structural architecture including blood vessels and lymphatics. Thus, sensitive structures, such as biological lumens, blood vessels, nerves, etc, are able to be preserved which are critical to maintaining the integrity and functionality of the tissue. This provides a number of benefits. To begin, this allows for the treatment of tissues that are often considered untreatable by conventional methods. Target tissues that are near sensitive structures are typically unresectable by surgical methods due to the inability to thoroughly and effectively surgically separate the tissue from the sensitive structures. Likewise, many conventional non-surgical therapies are contraindicated due to the potential for damage to the sensitive structures by the therapy or because the therapies are deemed ineffective due to the proximity of the sensitive structures. In addition, the ability to treat tissue near sensitive structures also provides a more comprehensive treatment in that malignant margins are not left near sensitive structures. Once tissue is treated, the survival of the structural architecture also allows for the natural influx of biological elements, such as components of the immune system, or for the introduction of various agents to further the therapeutic treatment.

However, a variety of risks are involved in using PEF energy. A few of such risks are described herein below.

Gas Bubble Formation

Typically, delivering PEFs in an ionic solution (saltwater, blood, interstitial fluid, etc.) will result in electrolytic reactions that affects the compounds within the solution, most notably separating water molecules resulting in hydrogen gas (at the active cathode) and chlorine gas (at the active anode) components. Thus, these gases are considered electrochemical generated gases. Alternating the PEF polarity during energy delivery will reduce the degree of bubble formation by alternating which item is being produced. However, this alone does not eliminate the generation of gas entirely, as the active periods during each phase of the polarity will continue to contribute to gas formation.

Gas bubble formation has a range of implications in clinical cases, which will vary with the location and application being targeted. In tissue destruction applications, whereby one or more electrodes are placed into the targeted region of tissue to deliver the PEFs either between the electrodes or in communication with a distant external dispersive pad, gas formation has been clearly visualized on ultrasound. It is routinely regarded as an inconsequential collateral effect of treatment delivery and has not been regarded as a confounding factor that alters treatment delivery. However, gas formation contributes to several effects, which may be desirable or undesirable depending on the application. In one consideration, the gas formation applies pressure to the adjacent tissue regions, and can distort tissue geometries, disrupt tissue architecture, or displace other materials within the tissue. In another consideration, gas formation could enter the bloodstream prior to dissolving. The circulating gaseous "bubble" could then travel through arterial pathways or subsequent veins to cause an embolism in the downstream tissues leading to ischemia, causing downstream cell and tissue death, pain, and other risks for the patient. The bubble may also travel back through the systemic circulation prior to dissolving, and cause a pulmonary embolism, which could cause pain, morbidity, or patient death.

In addition to the gas formed by the induced electrochemical reactions, gas can also be formed by vaporization. Electric currents will increase the temperature of the ionic solution by Joule heating. In cases where the induced temperature exceeds the phase change value, vaporization of the water content will take place. Both vaporization and electrochemical generated gases show several orders of magnitude lower electric conductivity than ionic solutions. Thus, at the region of tissue being treated by the high voltage, high energy electric pulses, the resulting electric field inside the gas could be higher than the electric breakdown exhibited as a sparking electric arc, or a larger combustion event depending on the size, quantity, type, and distribution of gaseous bubbles being generated. This is a particular risk when the PEF protocol and tissue type results in the generation of a large amount of gas that is not readily removed from the local tissue environment. Such spark production, encouragement, and potential combustion events caused by bubble formation may result in high-current events affecting generator performance (or breaking the generator) as well as distortions of energy deposition patterns that affect treatment outcomes, producing risks including burned tissue, overtreated tissue, undertreated tissue, or a combination of these effects. These effects could all seriously affect the efficacy, morbidity, and potentially the mortality of the PEF therapy.

In another consideration for gas formation, the presence of the gas:liquid:tissue mixture will result in a heterogeneously altered electrical conductivity environment (in essence, the electric current may preferentially flow around or through the gas, changing its flow through the targeted tissue). This could result in higher energy concentrations in some regions and absent or reduced energy concentrations in others. This may inherently distort energy delivery and deposition, potentially affecting treatment efficacy, morbidity, and mortality of the procedure.

In addition to gas formation implications in solid tissue regions, the risks are also present and potentially compounded when delivering PEF treatments into fluid targets, such as blood within the vasculature or cardiopulmonary system. Of particular concern, gas bubbles generated in the left atrium and ventricle of the heart will rapidly be expelled by the heart into the aorta. These bubbles may enter the coronary circulation, the carotid vessels, or other blood vessels. If the bubbles do not dissolve back into the fluid, they may get lodged into the narrowing portions of the arteries, restricting or eliminating blood flow through these vessels, causing ischemia to the downstream tissues. Bubble formation has been found as a risk in cardiac treatments for indications such as atrial fibrillation by various energy modalities, including cryoablation, radiofrequency ablation, and PEF treatments. There is a significant risk for symptomatic and asymptomatic cerebral ischemic events. In addition, the tendency for bubbles to float or move upwards makes them likely to enter the coronary artery on patients when placed in the supine position. Due to the likelihood and severity of issues that may be induced by gas formation during conventional procedures such as atrial fibrillation electrical isolation procedures, particular attention has been paid by clinicians and researchers to quantify and reduce the risk of these events in patients, including efforts to reduce or capture bubble formation. However, gas formation from PEF treatments has remained a standard collateral effect and patient risk.

Electrical Discharge

When delivering PEFs between electrodes, the generally high voltages employed can cause a breakdown in the delivery device, the tissue solid components, or the fluid in the tissue. This can cause an electrical discharge into this medium from the energized regions of the electrode. Electrical discharges can occur at the microscale, where they are not visible, or they can occur at a scale that is visible, generally manifesting as a visible "arc" or spark. The discharge is often accompanied by a pressure wave and audible sound than increases as the intensity of the discharge.

Discharges from the electrode cause a distortion in the quantity and distribution of the affecting items from the PEF therapy. They can concentrate the electric current into a focused area that causes stronger treatment effects (overtreatment) or burning from Joule heating in the region near the discharge. This may also reduce the electric current and subsequent electric field induced in the rest of the tissue (undertreatment). The electric breakdown of the current pathway may also result in a spike of electric current flowing through the system, which could increase the total electric current that must be generated by the PEF generator. Such spikes could exceed the PEF generating capacity of the generator or could cause high currents within the generator that damage the internal circuitry of the generator. In addition, electric discharge over ionic medium can generate reactive species (mainly nitrogen and oxygen) that will alter the composition of the medium having major impact on the pH of the solution and the normal biomolecule interaction.

Electrical discharges can commonly occur in PEF therapies due to the voltages used by these therapies. Bipolar electrode arrangements are particularly susceptible to major electrical arcing events due to the close proximity of the cathode and anode to each other, which may generate an electric discharge between electrodes also known as full discharge. This will induce a complete short-circuit if the voltage-to-distance ratio is not properly titrated. Permitting electrical discharges adds a degree of unpredictability and risk to the procedures. Avoiding them may reduce the efficacy of the therapy by reducing the intensity of the therapy that may be delivered.

Cavity Formation

As a result of the electrical discharge, both visible and invisible, a pressure wave is generated, that is apparent as an audible "popping" tone. This tone is commonly encountered in many PEF therapies and accepted as a collateral effect of treatment delivery. However, when the discharge and the pressure wave is of sufficient intensity and repeated a sufficient number of times, the energy transferred and deposited into the tissue from this pressure wave can severely disrupt the tissue architecture and cells. The resulting effect is the accumulated generation of a defect or cavity within the tissue at the regions near the electrode, which experience the strongest intensity of these effects.

The generation of the cavity adds considerable risk to procedure deliveries in or near solid tissues and ductal systems. The resulting "shredding" and destruction of the tissue may damage sensitive structures, such as blood vessels, nerves, or other ductal systems such as the bile duct, urethra, ureter, or lymphatics. These shredding effects could result in hemorrhage, thrombus or emboli formation, or disruption of tissue function. Generally, PEF treatments are utilized in lieu of other therapies due to their ability to spare these sensitive structures. The formation of cavities from the therapy jeopardizes this benefit of most PEF therapies for tissue regions in close proximity (0.1-5 mm) from the electrode.

In other instances, cavity formation and disruption via produced pressure waves may be desirable. For example, the disruption or dislodging of gallstones or kidney stones may be a target for this type of effect. Further, the fluid-filled cavity produced by these effects will generally be more conductive than the pre-existing tissue. Thus, continuing to deliver PEF (or other energy-based modalities) into this generated tissue cavity will serve to expand the applicable effects of the electrode, acting as a "virtual-electrode". Further, the conductive fluid will be a more homogeneous electrical conductivity and provide a more evenly distributed conduit for electrical flow, reducing the likelihood of electrical discharges into the tissue that may occur when electrical conductivities are heterogeneous. Therefore, at times it is desirable to control cavity formation resulting from PEF therapies.

Muscle Contraction

PEF therapies may induce their desirable clinical effects by altering the targeted tissue, however, this can also lead to the generation of action potentials in the nerves, especially motor neurons, as well as skeletal muscle cells. The generation of action potentials in motor neurons can result in the generation of muscle contraction during energy delivery. Muscle contraction and the generation of nerve action potentials can be uncomfortable or painful if performed in conscious or semi-conscious patients. In addition, the electrodes delivering the therapy can move or dislodge, risking an alteration of treatment effect location. Moving electrodes may also puncture or damage sensitive tissues that were in proximity to the electrode locations at the beginning of treatment. These factors compound to safety concerns for the patient and user when delivering PEF therapies. Generally, contraction is worse as waveforms in a given polarity are longer, with DC being the worst and purely symmetrical biphasic being the least contractile for a given pulse length, and a strong correlation for asymmetric waveforms across the spectrum as they move from pure-symmetric to pure-DC (weaker to stronger).

In other instances, the induction of muscle contractions could be a desirable secondary (or primary) effect from PEF therapies. For example, it could be used in re-exciting tissue that has atrophied due to temporarily disconnected nerve fibers from injury or clinical procedures. In such an example, the PEFs could be delivered in proximity to the proximal or peripheral side of the motor neuron, inducing an action potential that excites the downstream skeletal muscle, retaining tone and preventing atrophy, as well as encouraging regeneration and recovery of the muscle and neurological tissues. Therefore, at times it is desirable to control and encourage the muscle contractions resulting from PEF therapies.

Temperature Rise

Delivery of energy to tissue results in Joule heating depending on the length of time the energy is applied along with other factors. When a packet or pulse of energy is delivered continuously, the energy for that individual portion is deposited concurrently, resulting in progressive temperature rise. This results in PEF therapies as having very high to extreme and rapid rises in temperature, especially at the tissue-electrode interface and regions within the first few mm of distance from the electrode(s). If appropriate mitigations are not taken, the cumulative temperature rise can result in thermal effect extents that could destroy the extracellular matrix architectural proteins (e.g., collagen), resulting in disruption of tissue function and potential dangers to the patient.

Consequently, improved therapies are desired to control these aspects of PEF and mitigate any associated risks. Such improvements should be safe, reliable, effective, easy to implement and cost efficient. At least some of these objectives will be met by the present invention.

SUMMARY OF THE INVENTION

Described herein are embodiments of apparatuses, systems and methods for treating target tissue. Likewise, the invention relates to the following numbered clauses:

1. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising one or more packets of pulses to provide the treatment and comprising one or more delay periods which manipulates or reduces or avoids one or more secondary effects.

2. A system as in claim 1, wherein the one or more secondary effects comprises bubble formation.

3. A system as in claim 2, wherein bubble formation comprises formation of bubbles greater than or equal to 0.1 mm in diameter.

4. A system as in any of the above claims, wherein each of the pulses in the one or more packets of pulses has an on-time in a range 0.5 to 20 microseconds.

5. A system as in any of claims 1-3, wherein each of the pulses in the one or more packets of pulses has a continuous on-time of up to 5 microseconds.

6. A system as in any of the above claims, wherein each of the pulses has a duty cycle of less than or equal to 2.5 percent.

7. A system as in any of the above claims, wherein the delay period is greater than or equal to 1 microsecond.

8. A system as in claim 7, wherein the delay period is in a range of 1 to 250 microseconds.

9. A system as in claim 7, wherein the delay period is in a range of 10-100 microseconds.

10. A system as in claim 7, wherein the delay period is greater than or equal to 100 microseconds.

11. A system as in claim 7, wherein the delay period is greater than or equal to 250 microseconds.

12. A system as in claim 7, wherein the delay period is greater than or equal to 500 microseconds.

13. A system as in claim 7, wherein the delay period is greater than or equal to 1000 microseconds.

14. A system as in claim 7, wherein the at least one electrode is configured to be positioned within an ionic solution near the tissue and wherein the delay period is in a range of 100 microseconds to 10 milliseconds.

15. A system as in claim 14, wherein the delay period is in a range of 250 microseconds to 1000 microseconds.

16. A system as in claim 7, wherein the at least one electrode is configured to be positioned within the tissue and wherein the delay period is in a range of 10 microseconds to 1 millisecond.

17. A system as in claim 16, wherein the delay period is in a range of 25 microseconds to 100 microseconds.

18. As system as in any of the above claims, wherein the one or more packets of pulses comprises 100 packets and wherein each packet comprises 40 biphasic pulses.

19. A system as in claim 1, wherein the one or more secondary effects comprises an electrical discharge event.

20. A system as in claim 19, wherein the electrical discharge event comprises electrical arcing from at least one of the at least one electrode.

21. A system as in any of claims 19-20, wherein each of the pulses in the one or more packets of pulses has an on-time in a range 1 to 50 microseconds.

22. A system as in any of claims 18-20, wherein each of the pulses in the one or more packets of pulses has a continuous on-time in a range of up to 20 microseconds.

23. A system as in any of claims 18-22, wherein each of the at least one packet of pulses has a duty cycle of less than or equal to 20 percent.

24. A system as in claim 20, wherein the electrical discharge event comprises generation of a pressure wave against the tissue.

25. A system as in claim 24, wherein the pressure wave is sufficient to generate a cavity within the tissue.

26. A system as in claim 25, wherein each of the at least one packet of pulses has a duty cycle of less than or equal to 50 percent.

27. A system as in any of claims 25-26, wherein each of the pulses in the one or more packets of pulses has an on-time in a range 10 to 100 microseconds.

28. A system as in any of claims 25-26, wherein each of the pulses in the one or more packets of pulses has a continuous on time of up to 50 microseconds.

29. A system as in any of claims 18-28, wherein the delay period is greater than or equal to 1 microsecond.

30. A system as in claim 29, wherein the delay period is in a range of 1 to 500 microseconds.

31. A system as in claim 29, wherein the delay period is in a range of 10-250 microseconds.

32. A system as in claim 29, wherein the delay period is greater than or equal to 50 microseconds.

33. A system as in claim 29, wherein the delay period is greater than or equal to 250 microseconds.

34. A system as in claim 29, wherein the delay period is greater than or equal to 500 microseconds.

35. A system as in claim 29, wherein the delay period is greater than or equal to 1000 microseconds.

36. A system as in any of claims 18-29, wherein the at least one electrode is configured to be positioned within an ionic solution near the tissue and wherein the delay period is in a range of 50 microseconds to 10 milliseconds.

37. A system as in claim 36, wherein the delay period is in a range of 250 to 1000 microseconds.

38. A system as in any of claims 18-29, wherein the at least one electrode is configured to be positioned within the tissue and wherein the delay period is in a range of 100 microseconds to 10 milliseconds.

39. A system as in claim 38, wherein the delay period is in a range of 250 to 2000 microseconds.

40. A system as in any of claims 18-29, wherein the at least one electrode is configured to be positioned within a lumen wherein the tissue resides within a wall of the lumen and wherein the delay period is in a range of 10 microseconds to 10 milliseconds.

41. A system as in claim 40, wherein the delay period is in a range of 50 to 500 microseconds.

42. As system as in any of claims 18-41, wherein the one or more packets of pulses comprises 100 packets and wherein each packet comprises 40 biphasic pulses.

43. A system as in claim 1, wherein the one or more secondary effects comprises a contraction of a muscle.

44. A system as in claim 43, wherein the at least one electrode is configured to create a lesion having a width and wherein reducing or avoiding contraction of the muscle causes the at least one electrode maintain a position that does not move more than 25% of the width.

45. A system as in claim 44, wherein the tissue comprises cardiac tissue and the lesion comprises a focal lesion.

46. A system as in any of claims 43-45, wherein the delay period is greater than or equal to 5 milliseconds.

47. A system as in claim 46, wherein the delay period is greater than or equal to 10 milliseconds.

48. A system as in claim 46, wherein the delay period is in a range of 5 milliseconds to 1 second.

49. A system as in claim 46, wherein the delay period is in a range of 5 to 100 milliseconds.

50. A system as in claim 46, wherein the delay period is in a range of 5 to 10 milliseconds.

51. A system as in claim 46, wherein the delay period is in a range of 10-30 milliseconds.

52. A system as in claim 46, wherein the delay period is greater than or equal to 1000 microseconds.

53. As system as in any of claims 43-52, wherein the one or more packets of pulses comprises 100 packets and wherein each packet comprises 40 biphasic pulses.

54. A system as in any of claims 43-53, wherein the one or more packets of pulses comprise at least two packets separated by a packet delay period of at least 30 milliseconds.

55. A system as in claim 54, wherein each of the packets are separated by a packet delay period of at least 30 milliseconds.

56. A system as in any of the above claims, wherein the pulses comprise biphasic pulses and the delay period comprises an inter-phase delay between a positive phase and a negative phase of a biphasic pulse.

57. A system as in claim 56, wherein each biphasic pulse comprises the inter-phase delay.

58. A system as in any of the above claims, wherein the delay period comprises an inter-packet delay.

59. A system as in claim 58, wherein the inter-packet delay is in a range of 30-5000 milliseconds.

60. A system as in claim 59, wherein the inter-packet delay is 30-40 milliseconds.

61. A system as in claim 59, wherein the inter-packet delay is 3000-5000 milliseconds.

62. A system as in any of the above claims, wherein the delay period comprises an inter-pulse delay.

63. A system as in any of the above claims, wherein the waveform comprises one or more bundles, wherein each bundle comprises two or more packets.

64. A system as in claim 63, wherein each bundle comprises three packets and wherein each bundle is spaced apart so as to be delivered within an ST interval of a cardiac rhythm of the patient.

65. A system as in claim 63, wherein the delay period comprises an inter-bundle delay.

66. A system as in any of the above claims, wherein the waveform has a voltage amplitude of 500 to 4,000 volts.

67. A system as in any of the above claims, wherein the waveform has a frequency of 300-800 kHz.

68. A system as in any of the above claims, wherein each of the one or more packets has 10-200 biphasic pulses.

69. A system as in any of the above claims, wherein each of the one or more packets has 20-50 biphasic pulses.

70. A system as in any of the above claims, wherein the treatment comprises 5 to 100 packets.

71. A system as in any of the above claims, wherein the treatment comprises 10 to 60 packets.

72. A system as in any of the above claims, further comprising a remote dispersive electrode positionable so that the energy is delivered in a monopolar manner.

73. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising one or more packets of pulses to provide the treatment and comprising one or more delay periods which avoids a peak temperature in the tissue that would have been reached by delivery of the energy without the one or more delay periods.

74. A system as in claim 73, wherein the peak temperature causes bubble formation.

75. A system as in any of claims 73-74, wherein the peak temperature is 100 degrees Celsius.

76. A system as in any of claims 73-75, wherein the peak temperature causes an electrical discharge.

77. A system as in any of claims 73-76, wherein the delay period is greater than or equal to 5 milliseconds.

78. A system as in claim 77, wherein the delay period is greater than or equal to 10 milliseconds.

79. A system as in claim 77, wherein the delay period is in a range of 5 milliseconds to 1 second.

80. A system as in claim 77, wherein the delay period is in a range of 5 milliseconds to 100 milliseconds.

81. A system as in claim 77, wherein the delay period is in a range of 5 milliseconds to 10 milliseconds.

82. A system as in claim 77, wherein the delay period is in a range of 10-30 milliseconds.

83. A system as in any of claims 73-82, wherein the waveform comprises one or more bundles, wherein each bundle comprises two or more packets.

84. A system as in claim 83, wherein each bundle comprises three packets and wherein each bundle is spaced apart so as to be delivered within an ST interval of a cardiac rhythm of the patient.

85. As system as in any of claims 73-84, wherein the one or more packets of pulses comprises 100 packets and wherein each packet comprises 40 biphasic pulses.

86. A system as in any of claims 73-85, wherein the pulses comprise biphasic pulses and the delay period comprises an inter-phase delay between a positive phase and a negative phase of a biphasic pulse.

87. A system as in claim 86, wherein each biphasic pulse comprises the inter-phase delay.

88. A system as in any of claims 73-85, wherein the delay period comprises an inter-packet delay.

89. A system as in claim 88, wherein the inter-packet delay is in a range of 30-5000 milliseconds.

90. A system as in claim 88, wherein the inter-packet delay is in a range of 30-40 milliseconds.

91. A system as in claim 88, wherein the inter-packet delay is in a range of 3000-5000 milliseconds.

92. A system as in any of claims 73-85, wherein the delay period comprises an inter-pulse delay.

93. A system as in any of claims 73-92, wherein the waveform comprises one or more bundles, wherein each bundle comprises two or more packets.

94. A system as in claim 93, wherein each bundle comprises three packets and wherein each bundle is spaced apart so as to be delivered within an ST interval of a cardiac rhythm of the patient.

95. A system as in claim 93, wherein the delay period comprises an inter-bundle delay.

96. A system as in any of claims 73-95, wherein the waveform has a voltage amplitude of 500 to 4,000 volts.

97. A system as in any of claims 73-96, wherein the waveform has a frequency of 300-800 kHz.

98. A system as in any of claims 73-97, wherein each of the one or more packets has 10-200 biphasic pulses.

99. A system as in any of claims 73-97, wherein each of the one or more packets has 20-50 biphasic pulses.

100. A system as in any of claims 73-99, wherein the treatment comprises 5 to 100 packets.

101. A system as in any of claims 73-99, wherein the treatment comprises 10 to 60 packets.

102. A system as in any of claims 73-101, further comprising a remote dispersive electrode positionable so that the energy is delivered in a monopolar manner.

103. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising at least one packet of pulses to provide the treatment wherein each pulse has a pulse length and at least one of the at least one packet comprises a delay having a delay period that is at least twice the pulse length.

104. A system as in claim 103, wherein the delay period is at least ten times the pulse length.

105. A system as in any of claims 103-104, wherein the at least one packet has a packet length at least 50 times the delay period.

106. A system as in claim 105, wherein the at least one packet has a packet length at least 100 times the delay period.

107. A system as in any of claims 103-106, wherein the delay comprises an inter-pulse delay.

108. A system as in claim 107, wherein the pulses are biphasic pulses and the inter-pulse delay is an inter-cycle delay.

109. A system as in any of claims 103-106, wherein the pulses are biphasic pulses and the delay comprises inter-phase delay.

110. A system as in any of claims 103-109, wherein the delay period comprises 250 to 1000 microseconds.

111. A system as in any of claims 103-110, wherein the at least one packet comprises at least 25 pulses.

112. A system as in claim 111, wherein the at least one packet comprises at least 40 pulses.

113. A system as in any of claims 103-112, wherein the least one packet is separated from an adjacent packet by an inter-packet delay of at least 30 microseconds.

114. A system as in claim 113, wherein the least one packet is separated from an adjacent packet by an inter-packet delay of 100-5000 microseconds.

115. A system as in any of claims 103-114, wherein the treatment comprises 5-100 packets.

116. A system as in claim 115, wherein the treatment comprises 10-60 packets.

117. A system as in any of claims 103-116, wherein the waveform has a voltage amplitude of 500-10,000 volts.

118. A system as in any of claims 103-117, wherein each pulse has a pulse length of 1.66 microseconds.

119. A system as in any of claims 103-117, wherein each pulse has a pulse length of 2.5 microseconds.

120. A system as in any of claims 103-117, wherein each pulse has a pulse length of 20 microseconds.

121. A system as in any of claims 103-120, further comprising a remote dispersive electrode positionable so that the energy is delivered in a monopolar manner.

122. A system as in any of claims 103-121, wherein the delay period is of sufficient length to reduce or avoid bubble formation near the at least one electrode.

123. A system as in any of claims 103-122, wherein the delay period is of sufficient length to reduce or avoid an electrical discharge event near the least one electrode.

124. A system as in any of claims 103-123, wherein the delay period is of sufficient length to reduce or avoid cavity formation in the tissue.

125. A system as in any of claims 103-124, wherein the delay period is of sufficient length to reduce or avoid contraction of a muscle of the patient.

126. A system as in any of claims 103-125, wherein the delay period is of sufficient length to avoid a peak temperature in the tissue that would have been reached by delivery of the energy without the one or more delay periods.

127. A system as in claim 126, wherein the peak temperature causes bubble formation.

128. A system as in any of claims 126-127, wherein the peak temperature is 100 degrees Celsius.

129. A system as in any of claims 126-128, wherein the peak temperature causes an electrical discharge.

130. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising at least one packet of biphasic pulses to provide the treatment wherein each biphasic pulse comprises an inter-phase delay in a range of 250 to 1000 microseconds.

131. A system as in claim 130, wherein the waveform has a voltage amplitude of 500-10,000 volts.

132. A system as in any of claims 130-131, wherein each pulse has a pulse length of 1.66 microseconds.

133. A system as in any of claims 130-131, wherein each pulse has a pulse length of 2.5 microseconds.

134. A system as in any of claims 130-131, wherein each pulse has a pulse length of 20 microseconds.

135. A system as in any of claims 130-134, wherein the delay period is of sufficient length to reduce or avoid bubble formation near the at least one electrode.

136. A system as in any of claims 130-135, wherein the delay period is of sufficient length to reduce or avoid an electrical discharge event near the least one electrode.

137. A system as in any of claims 130-136, wherein the delay period is of sufficient length to reduce or avoid cavity formation in the tissue.

138. A system as in any of claims 130-137, wherein the delay period is of sufficient length to reduce or avoid contraction of a muscle of the patient.

139. A system as in any of claims 130-138, wherein the delay period is of sufficient length to avoid a peak temperature in the tissue that would have been reached by delivery of the energy without the one or more delay periods.

140. A system as in claim 139, wherein the peak temperature causes bubble formation.

141. A system as in any of claims 139-140, wherein the peak temperature is 100 degrees Celsius.

142. A system as in any of claims 139-141, wherein the peak temperature causes an electrical discharge.

143. A system as in any of claims 130-142, further comprising a remote dispersive electrode positionable so that the energy is delivered in a monopolar manner.

144. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising 2-60 packets of pulses to provide the treatment wherein each packet includes at least one delay period of in a range of 250 to 1000 microseconds.

145. A system as in claim 144, wherein the waveform has a voltage amplitude of 500-10,000 volts.

146. A system as in any of claims 144-145, wherein each pulse has a pulse length of 1.66 microseconds.

147. A system as in any of claims 144-145, wherein each pulse has a pulse length of 2.5 microseconds.

148. A system as in any of claims 144-145, wherein each pulse has a pulse length of 20 microseconds.

149. A system as in any of claims 144-148, wherein the delay period is of sufficient length to reduce or avoid bubble formation near the at least one electrode.

150. A system as in any of claims 144-149, wherein the delay period is of sufficient length to reduce or avoid an electrical discharge event near the least one electrode.

151. A system as in any of claims 144-150, wherein the delay period is of sufficient length to reduce or avoid cavity formation in the tissue.

152. A system as in any of claims 144-151, wherein the delay period is of sufficient length to reduce or avoid contraction of a muscle of the patient.

153. A system as in any of claims 144-152, wherein the delay period is of sufficient length to avoid a peak temperature in the tissue that would have been reached by delivery of the energy without the one or more delay periods.

154. A system as in claim 153, wherein the peak temperature causes bubble formation.

155. A system as in any of claims 153-154, wherein the peak temperature is 100 degrees Celsius.

156. A system as in any of claims 153-155, wherein the peak temperature causes an electrical discharge.

157. A system as in any of claims 144-156, further comprising a remote dispersive electrode positionable so that the energy is delivered in a monopolar manner.

158. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising at least one packet of pulses having a delay period wherein the at least one packet has a packet length at least 50 times the delay period.

159. A system as in claim 158, wherein the at least one packet has a packet length at least 100 times the delay period.

160. A system as in any of claims 158-159, wherein each pulse has a pulse length of 1.66 microseconds.

161. A system as in any of claims 158-159, wherein each pulse has a pulse length of 2.5 microseconds.

162. A system as in any of claims 158-159, wherein each pulse has a pulse length of 20 microseconds.

163. A system as in any of claims 158-162, wherein the delay period is of sufficient length to reduce or avoid bubble formation near the at least one electrode.

164. A system as in any of claims 158-163, wherein the delay period is of sufficient length to reduce or avoid an electrical discharge event near the least one electrode.

165. A system as in any of claims 158-164, wherein the delay period is of sufficient length to reduce or avoid cavity formation in the tissue.

166. A system as in any of claims 158-165, wherein the delay period is of sufficient length to reduce or avoid contraction of a muscle of the patient.

167. A system as in any of claims 158-166, wherein the delay period is of sufficient length to avoid a peak temperature in the tissue that would have been reached by delivery of the energy without the one or more delay periods.

168. A system as in claim 167, wherein the peak temperature causes bubble formation.

169. A system as in any of claims 167-168, wherein the peak temperature is 100 degrees Celsius.

170. A system as in any of claims 167-169, wherein the peak temperature causes an electrical discharge.

171. A system as in any of claims 167-170, further comprising a remote dispersive electrode positionable so that the energy is delivered in a monopolar manner.

172. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the energy provides a treatment to the tissue, wherein the energy is generated from a waveform comprising at least one packet of pulses wherein each pulse has a duty cycle of less than or equal to 50 percent so as to reduce or avoid one or more secondary effects.

173. A system as in claim 172, wherein the one or more secondary effects comprises cavity formation in the tissue.

174. A system as in claim 172, wherein each pulse has a duty cycle of less than or equal to 20 percent.

175. A system as in claim 174, wherein the one or more secondary effects comprises an electrical discharge event.

176. A system as in claim 172, wherein each pulse has a duty cycle of less than or equal to 2.5 percent.

177. A system as in claim 176, wherein the one or more secondary effects comprises bubble formation.

178. A system as in claim 177, wherein bubble formation comprises formation of bubbles greater than or equal to 0.1 mm in diameter.

179. A system for treating tissue comprising:
an electrode positionable near the tissue; and
a generator in electrical communication with the electrode, wherein the generator includes at least one energy delivery algorithm that provides pulsed electric field energy to the electrode so that the energy treats the tissue, wherein the energy is generated from a waveform having a particular delay period between pulses selected to affect gas formation, external electrical discharge, muscle contraction, cavity formation, and/or temperature rise.

180. A method of influencing at least one secondary effect of pulsed electric field therapy comprising:
selecting a particular delay period between portions of a pulsed electric field waveform so as to influence the at least one secondary effect.

181. A method as in claim 1, wherein the at least one secondary effect comprises gas formation.

182. A method as in claim 1, wherein the at least one secondary effect comprises electric discharge.

183. A method as in claim 1, wherein the at least one secondary effect comprises cavity formation.

184. A method as in claim 1, wherein the at least one secondary effect comprises muscle contraction.

185. A method as in claim 1, wherein the at least one secondary effect comprises temperature rise.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8A illustrates the result of using a waveform having a cycle delay of approximately 50 ns which resulted in significant tissue cavity format. FIG. 8B illustrates the result of using the same waveform but with a cycle delay of approximately 1000 µs.

FIG. 9, illustrates Nodes of Ranvier occurring along a myelinated axon where the axolemma (axon membrane) is exposed to the extracellular space.

FIG. 10 illustrates modeling of myelinated axon regions are modeled as electrical components.

FIGS. 11A-11D illustrates the charging and discharging behavior of a motor neuron in response to pulsed electric field waveforms having no or low cycle delay versus a larger cycle delay.

DETAILED DESCRIPTION OF THE INVENTION

Specific embodiments of the disclosed devices, systems, and methods will now be described with reference to the drawings. Nothing in this detailed description is intended to imply that any particular component, feature, or step is essential to the invention.

A variety of different types of energy have been used for therapeutic treatments of patients, including radiofrequency (RF) energy, microwave (MW) energy, high intensity focused ultrasound (HIFU) energy, and pulsed electric field (PEF) energy, to name a few. These energy modalities differ according to the waveform of the electric signal provided by the generator. When possible, they are categorized according to the electromagnetic spectrum. The electromagnetic spectrum covers electromagnetic waves with frequencies ranging from below one hertz to above $10^{25}$ hertz, corresponding to wavelengths from thousands of kilometers down to a fraction of the size of an atomic nucleus. This frequency range is divided into separate bands, and the electromagnetic waves within each frequency band are called by different names; beginning at the low frequency (long wavelength) end of the spectrum these are: radio waves, microwaves, terahertz waves, infrared, visible light, ultraviolet, X-rays, and gamma rays at the high-frequency (short wavelength) end. The electromagnetic waves in each of these bands have different characteristics, such as how they are produced, how they interact with matter, and their practical applications.

RF energy is the lowest portion in the electromagnetic spectrum familiar as a medium of analog and modern digital wireless communication system. It spreads in the range between 3 kHz and 300 GHz and is a continuous waveform. Waveforms having a frequency in the RF range have been manipulated to change from a continuous waveform to a pulsed waveform. Thus, energy is applied intermittently, in pulses or short bursts of pulses. Pulsed RF or pulsed electric fields (PEF) provide different effects on cellular tissue than continuously delivered RF because cells react differently over the time that the energy is applied. For example, RF ablation causes cell death due to thermal damage to the cells while PEF cause cell death by non-thermal (i.e. below a threshold for causing thermal ablation) effects. Such cell death maintains extracellular matrices so that the targeted tissue maintains its structural architecture including blood vessels and lymphatics. Thus, sensitive structures, such as biological lumens, blood vessels, nerves, etc., are able to be preserved which are critical to maintaining the integrity and functionality of the tissue.

Figure 1:
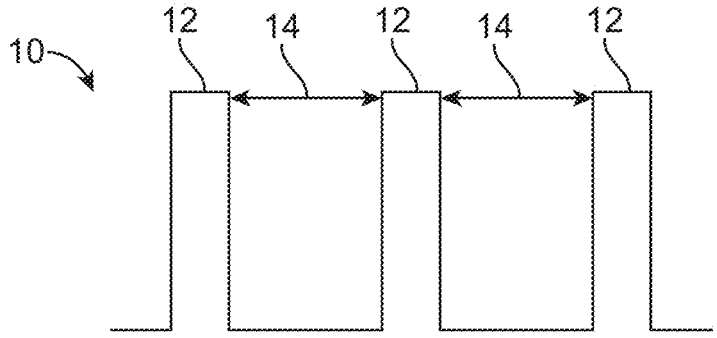
FIG. 1 illustrates an embodiment of a pulsed electric field waveform having pulses that are monophasic and are separated by an inter-pulse delay that is measured from one polarity pulse to the next pulse of the same polarity.
Figure 2:
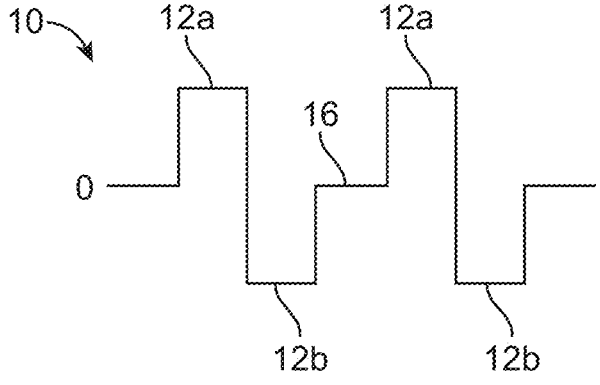
FIG. 2 illustrates an embodiment of a pulsed electric field waveform having pulses that are biphasic wherein each cycle is comprised of one polarity pulse followed by an opposite polarity pulse.
Figure 3:
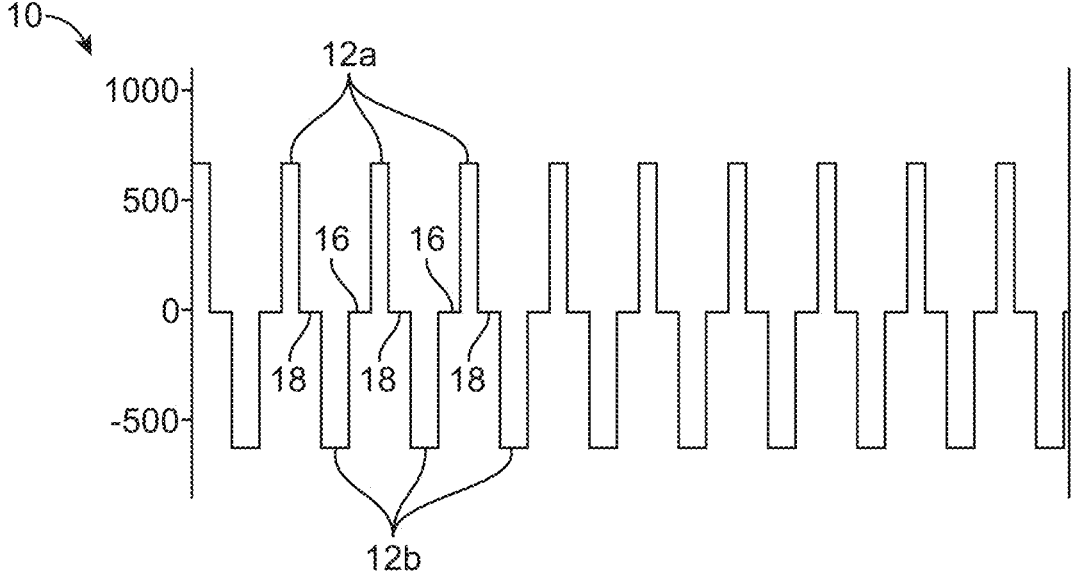
FIG. 3 illustrates an embodiment of a pulsed electric field waveform having pulses that are biphasic such as in FIG. 2, however in this embodiment the opposite polarity pulses are separated by an inter-phase delay.

FIG. 1 illustrates an embodiment of a PEF waveform 10 having pulses 12 that are monophasic and are separated by an inter-pulse delay 14 that is measured from one polarity pulse to the next pulse of the same polarity. Thus, the inter-pulse delay 14 may be considered a DC pulse delay. FIG. 2 illustrates an embodiment of a PEF waveform 10 having two pulses 12 that are each biphasic wherein each cycle is comprised of one polarity phase 12a followed by an opposite polarity phase 12b. In this embodiment, there is no delay between these two opposite polarity phases 12a, 12b, however there is an inter-cycle delay 16 between the cycles (i.e. biphasic pulses). It may be appreciated that inter-cycle delays are a form of inter-pulse delays wherein the pulses are biphasic pulses. FIG. 3 illustrates an embodiment of a PEF waveform 10 having pulses 12 that are biphasic such as in FIG. 2, however in this embodiment the opposite polarity phases 12a, 12b are separated by a switch delay or inter-phase delay 18.

Figure 4:
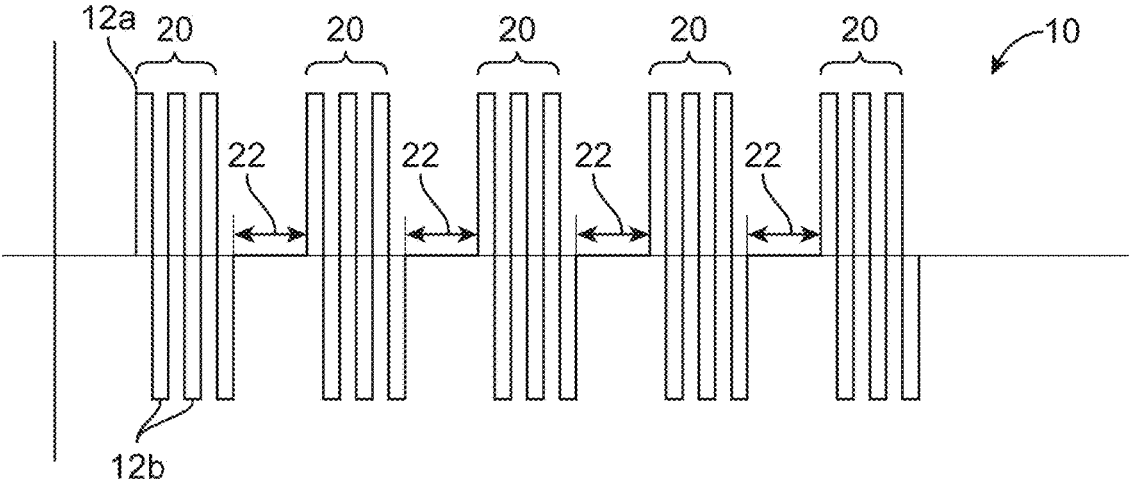
FIG. 4 illustrates example pulses grouped in bursts or packets.

In some instances, pulses 12 are grouped in bursts or packets 20, such as illustrated in FIG. 4. Here, five packets 20 are illustrated, each packet 20 being comprised of a plurality of cycles or biphasic pulses. The packets 20 are separated by inter-packet delays 22. It may be appreciated that packets 20 may be comprised of a variety of different types of pulses (e.g. monophasic, biphasic, etc.) and the same or differing polarities. For example, in some embodiments, a packet 20 is comprised of a series of pulses 12 of the same polarity, followed by a switch in polarity for one or more pulses 12, which may or may not be followed by subsequent switches in polarity for one or more additional pulses 12.

Figure 5:
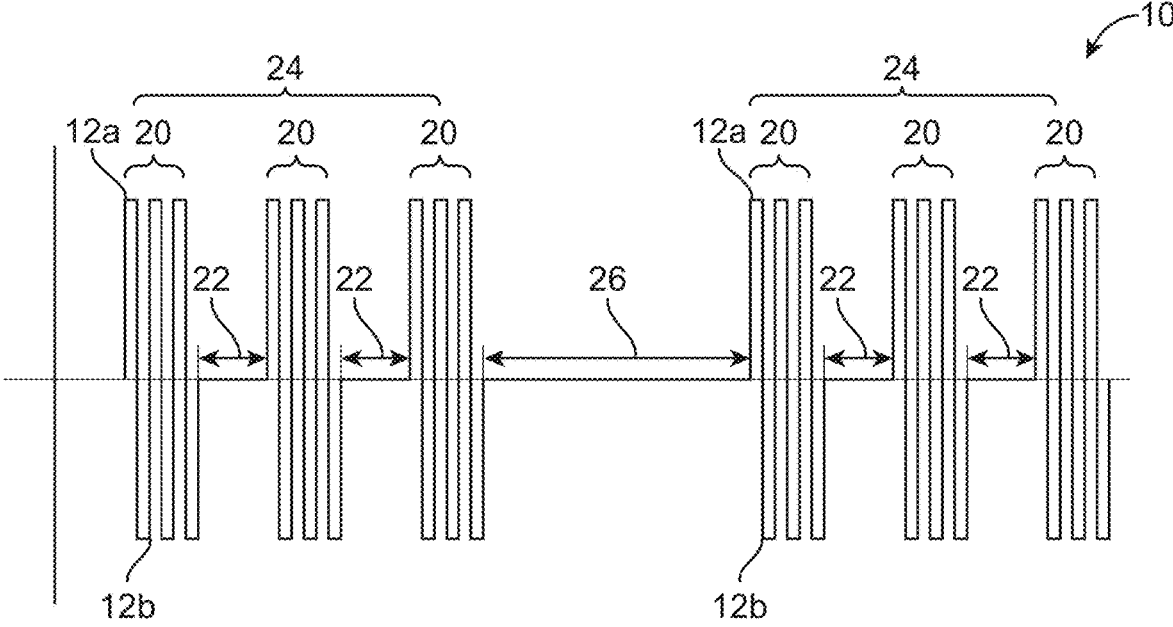
FIG. 5 illustrates example packets grouped into batches or bundles.

Optionally, in some instances, packets 20 are grouped into batches or bundles 24, such as illustrated in FIG. 5. Here, two bundles 24 are illustrated, each bundle 24 being comprised of three packets 20. The bundles 24 are separated by inter-bundle delays 26. Typically, the energy is applied to the patient so that the inter-bundle delays 26 are synced with the heartbeat, wherein the inter-bundle delays 26 occur during the sensitive portions of the heartbeat. Thus, energy is applied outside of sensitive portions of the heartbeat so as to avoid inducing arrhythmias. In some embodiments, energy is delivered during the R-T interval of a patient's ECG rhythm. In other embodiments, the PEF energy is delivered agnostic to the location in the ECG waveform. Biphasic waveforms, in particular, are able to be delivered in this manner safely without disrupting the normal electrophysiological behavior of the heart. Thus, bundles may be used for reasons such as expediting treatments, with varying inter-bundle delays 26 that are established for other reasons, such as thermal mitigation. Alternately, packets 20 can be delivered in quick succession, without bundling of the packets. These packets may be delivered synchronously or asynchronously to the ECG rhythm.

Typically, a treatment is considered the period of energy delivery to a target area before moving to the next target area. For example, when treating a passageway of a lung, an energy delivery device may comprise an electrode that circumferentially contacts an inner surface of a segment of the lung passageway. The energy from the waveform may be applied continuously, or the user may start and stop energy activation/application. In either case, energy is delivered to the electrode until the segment of target tissue receiving the energy is desirably treated. Energy delivery is then ceased, and the electrode is repositioned within the lung passageway so as to treat a new segment of target tissue (either overlapping or not overlapping with the first segment of target tissue). Each period of energy delivery to a target area before moving to the next target area is considered a treatment. Thus, a patient would typically undergo a plurality of treatments within a lung during a procedure.

When treating a portion of the heart, such as when ablating portions of heart to treat atrial fibrillation, an energy delivery device may comprise an electrode having a blunt tip that contacts a surface of the atrium or pulmonary vein. In such instances, energy is delivered from the tip to the cardiac tissue to create ablation at the area of contact. This is repeated as the tip is moved to various locations, so as to create a circular or linear ablation which blocks electrical conduction through the cardiac tissue. Again, a treatment is considered the period of energy delivery to a target area before moving to the next target area. Thus, a full conduction block would typically involve a plurality of treatments, wherein each treatment is comprised of one or more activations.

In summary, for the purposes described herein, a treatment typically comprises the entire period of PEF delivery to affect a targeted section of tissue that is delivered from one electrode (or set of electrodes) to another electrode (or set of electrodes) before moving one of the electrodes. Likewise, an activation typically comprises the PEF treatment delivery for a single "start" sequence initiated by a user. Multiple activations may be delivered in a single treatment. The time between activations would be determined by the user and any secondary constraints on PEF delivery (such as synchronization with a cardiac rhythm, time for temperature to return to baseline, or due to incidental incomplete treatment delivery of the first activation).

The PEF waveforms are delivered to tissue through one or more energy delivery bodies, each having one or more electrodes. Ultimately, the physical arrangement of electrodes forms a circuit. Electrodes may behave as the cathode or anode, or both, at any given time within a packet, a series of pulses, a cycle, an activation, or any other period that separates two pulses. When electrodes that partially or fully create the electrical circuit are in the same regional proximity, particularly in or near the targeted tissue, the system is referred as bipolar or multipolar electrode arrangements. Multipolar arrangements would apply when more than two polarity orientations are used, such as one electrode set at 1000 V, a second at 500 V, and a third at 0V, whereby the 2nd electrode is known to be a negative polarity to the first electrode, but a positive polarity to the third electrode. When one or more of the electrodes in the circuit are placed separate at a distant, non-targeted region of tissue (e.g., a dispersive pad) this arrangement is referred as a monopolar electrode arrangement. These descriptions are for convenience, and descriptions of the use of the concepts described herein for either of these arrangements may be interpreted as applicable to other arrangements of electrodes.

Energy delivery may be actuated by a variety of mechanisms, such as with the use of an actuator 132 on the device 102 or a foot switch operatively connected to the generator 104. Such actuation typically provides a single energy dose or activation. The energy dose is typically defined by the number of packets delivered and the voltage of the packets. Each energy dose delivered to the target tissue is configured to maintain the temperature at or in the target tissue below a threshold for thermal ablation, particularly thermal ablation or denaturing of stromal proteins in the basement membrane or deeper submucosal extracellular protein matrices. In addition, the doses may be titrated or moderated over time so as to further reduce or eliminate thermal buildup during the treatment procedure. Instead of inducing thermal damage, defined as extracellular protein coagulation at sites of danger to therapy, the energy dose provides energy at a level which induces treatment of the condition without damaging sensitive tissues.

It may be appreciated that the delays described herein (e.g. inter-pulse delay 14, inter-cycle delay 16, inter-phase delay 18, inter-packet delay 22, inter-bundle delay 26, etc.) may be consistent or varied throughout a packet 20, bundle 26 and/or treatment depending on the type of waveform. Likewise, some delays may not be present because they are zero or because they are not relevant to the waveform (e.g. if no bundles 24 are present, there are no inter-bundle delays 26 due to irrelevancy). Inter-pulse delays 14 may be consistent throughout a packet 20 of pulses 12, or they may change over the course of the packet 20. For example, a first inter-pulse delay may be 50 ns, followed by a second inter-pulse delay of 1 ms, after which the sequence is repeated. There may be sub-patterns within a packet 20 wherein a given sequence of pulses 12 of comparable with varying polarities is repeated (e.g.: up, up, down, delay, up, up, down, . . . ; up, up, down, down, up, delay, down, up, up, down, down, . . . ; etc), these sub-patterns are referred to as a series of pulses. Each series of pulses has the same pattern which defines it as a series. However, each series may have differing characteristics such as having pulses of differing polarity, differing pulse widths, differing amplitudes, and differing inter-phase and/or interpulse delays in differing patterns. In some embodiments, different series are positioned in a repeating sequence. Thus, in some embodiments, there are relevant intra-series delays from any given pulse to the subsequent pulse, and a secondary range of inter-series delays between the given series.

In some embodiments, inter-pulse delays 14 are consistent over the course of a packet 20 and in other embodiments, the inter-pulse delays 14 vary within a packet 20. In some embodiments, the duty cycle of pulses comprising a packet ranges from <0.01% to 100%. In some embodiments, a treatment comprises identical packets 20, wherein each packet 20 has consistent inter-pulse delays 14 or inconsistent inter-pulse delays 14. In other embodiments, a treatment comprises at least two different types of packets 20, wherein each of the at least two different types of packets 20 has consistent inter-pulse delays 14 yet the inter-pulse delays 14 differ between the at least two different types of packets 20. Or in other embodiments, at least one of the at least two different types of packets 20 has inconsistent inter-pulse delays 14 that differs from the other. Typically, when bundles 24 are present, the inter-bundle delay 26 is consistent when synced with a cardiac rhythm, however it may be appreciated that the inter-bundle delay 26 may vary either with the patient changes in cardiac rhythm or upon other treatment delivery protocol constraints.

In any case, it may be appreciated that any combination of delays (e.g. inter-pulse delay 14, inter-cycle delay 16, inter-phase delay 18, inter-packet delay 22, inter-bundle delay 26, etc.) may be utilized within a treatment to obtain a desired outcome. In particular, these delays may be specifically manipulated to obtain particular desired outcomes. For example, one, some or all of these delays may be manipulated to control various aspects of PEF therapy so as to mitigate any associated risks, such as gas formation, electrical discharge, cavity formation, muscle contraction, and temperature rise, to name a few. In some embodiments, the delays distribute the period over which (high) voltage PEF energy is delivered, resulting in marked changes and optimization to the treatment delivery outcomes. In some embodiments, the range of delays described herein are between 0 s and 100 ms.

In some embodiments, the delay periods are manipulated to distribute the pace of energy delivery and permit resolution and decay of certain effects prior to them inducing effects from their accumulation. When applying PEFs for biological cell and tissue manipulation, where charge accumulation and decay is at a different timescale than the other effects, it is possible to accumulate treatment effect on the cell with multiple cycles or series of pulses, but without causing a variety of secondary treatment effects, such as gas formation, electrical discharge, cavity formation, muscle contraction, and temperature rise, to name a few. In other instances, these secondary accumulated treatment effects may be desirable to initiate or enhance therapy outcomes, and thus the delays will be selected to encourage these effects, which again are done in a manner that does not alter the primary objective of inducing cellular and tissue responses to the PEFs. These examples of secondary effects are not an exhaustive list and other secondary effects desired to be manipulated may also be controlled by selecting appropriate delays.

Gas Formation

In some embodiments, delays are manipulated to discourage the gas formation generated by PEF therapies. As mentioned previously, in order for molecular bonds to break, thereby forming gas, energy needs to be delivered for a sufficient period of time. Further, once gas has formed, it aggregates over time and coalesces into collectively larger regions, forming progressively larger bubbles. The larger the bubbles, the longer the time taken for the bubbles to resorb into fluid. These processes can be diminished or avoided by skillfully introducing delays into the waveform. Such delays provide energy in time periods insufficient to form any or any substantial quantities of gas and/or insufficient to allow any bubbles that may have been generated to grow large enough to avoid dissolution. The total energy being delivered is not altered by such manipulation the delays, thereby preserving the overall treatment effect. Thus, with the proper choice of delays, it may be possible for gas formation to be avoided or for bubbles to entirely re-dissolve or re-form into other molecules.

Even if the delays are insufficient for complete elimination of the gas from resorbing into the fluid, is the delays may be sufficient to prevent the meaningful aggregation of the gases into larger bubbles. In such instances, the smaller bubbles are migrating and beginning to resorb prior to the next onset of energy and additional gas formation. In this way, the bubbles do not coalesce into large bubbles. Importantly, the size of the bubble also relates to its effects in the body. A small (<0.1 mm diameter) bubble typically will resorb in the order of seconds and is generally too small to induce a meaningful ischemic event. Thus, bubbles produced at this size typically do not pose a meaningful threat to patient safety. Conversely, larger bubbles (>0.1 mm) may take minutes or longer to resorb and may disrupt or occlude blood vessels. Therefore, even if bubble generation cannot be eliminated entirely, suppressing the size and quantity of bubbles produced to only those that are clinically insignificant and/or will resorb quickly may be equally effective.

In some embodiments, when delivering PEF therapies in blood (an electrolytic fluid) in a monopolar fashion (i.e. with the use of a remotely positioned return electrode) using 7 F tip cardiac ablation focal electrode catheter, the suppression of the amount and size of produced gas formation may begin setting in when cycle delays of 1 s are present in a waveform having pulses 12 that are biphasic (1 μs duration) and have a voltage of 3000V. In other embodiments, a comparable energy delivery begins showing meaningful reductions in gas formation when cycle delays are 10 or 20 μs, with a complete elimination of hyperechoic bubbles when cycle delays are greater than or equal to 150 μs.

Figures 6A, 6B, 6C:
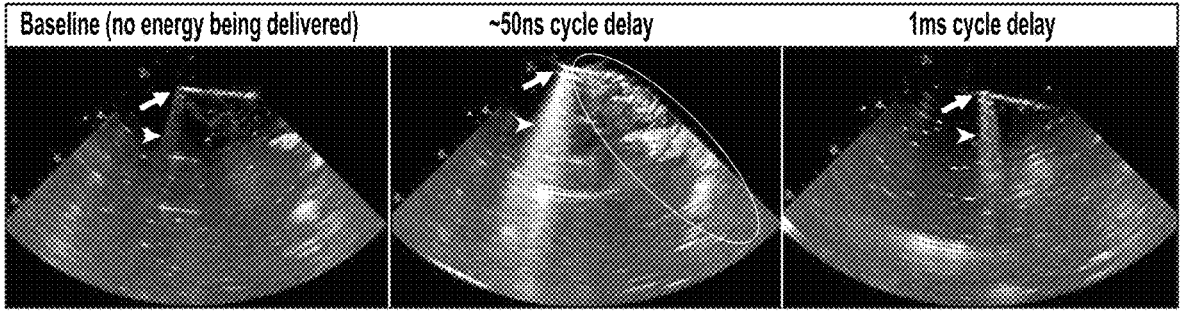
FIGS. 6A-6C provides ultrasound images which illustrate bubble formation under various conditions when an energy delivery body is submerged into a saline bath.

FIGS. 6A-6C provides ultrasound images which illustrate bubble formation under various conditions when an energy delivery body 108 (e.g. electrode) is submerged into a saline bath. FIG. 6A illustrates a baseline image of an energy delivery body 108, indicated by an arrow, wherein no energy is being delivered. Thus, this image serves as a control. A shadow artifact is highlighted at the arrowhead. FIG. 6B illustrates energy delivery by the energy delivery body 108 wherein the waveform has a cycle delay of 50 ns. This shows an extensive degree of hyperechoic bubbles being generated and visualized on the screen. FIG. 6D illustrates energy delivery by the energy delivery body 108 wherein the waveform has the same parameters as in FIG. 6B, however the waveform has a cycle delay of 1 ms. As shown, no bubbles are visible anywhere within the imaging window.

Thus, in some embodiments, when delivering PEF therapies in blood or any electrolytic fluid, adjacent to a target tissue, such as in cardiac or vascular clinical applications, gas formation can be eliminated with the use of delays, such as cycle delays or other delays, in the range of 100 μs-10,000 μs, preferably 100 μs-1000 μs, such as 250 μs-1000 μs. It may be appreciated that in some embodiments delays are 100 μs, 150 μs, 200 μs, 250 μs, 300 μs, 400 μs, 500 μs, 600 μs, 700 μs, 800 μs, 900 μs, 1000 μs, in the range of 100-250 μs, 250-500 μs, 500-1000 μs, greater than 250 μs, greater than 500 μs, greater than 1000 μs, 1000-5,000 μs, 1000-10,000 μs, to name a few. In some embodiments, when delivering PEF to solid tissues, such as when the energy deliver body 108 is positioning into a target tissue, gas formation can be eliminated with the use of delays, such as cycle delays or other delays, in the range of 10 μs-1000 μs, preferably 25 μs-100 μs. It may be appreciated that in some embodiments delays are 10 μs, 20 μs, 25 μs, 30 μs, 40 μs, 50 μs, 60 μs, 70 μs, 80 μs, 90 μs, 100 μs, in the range of 10-100 μs, 25-500 μs, 500-1000 μs, greater than 25 μs, greater than 50 μs, greater than 100 μs, to name a few.

Electrical Discharge

In some instances, when energy is delivered from an energy delivery body 108 to the patient, electric current concentrates and accumulates in a focal region around the energy delivery body 108. At a point, the cumulative energy delivery exceeds the breakdown potentials of the energy delivery body 108 material or the surrounding tissue or fluid. This causes electrical discharge events (e.g. sudden flow of electricity, such as arcing) from the energy delivery body 108 to the nearby tissue, fluid, or cells. However, the introduction of appropriate waveform delays permits relaxation of charge buildup in the fluids and tissue materials. Thus, by introducing delays, the energy delivery is not constant, thus allowing for relaxation of the charge buildup at various times prior to resuming energy delivery. With a sufficient number and duration of delays, discharge events can be prevented. The sufficient number and duration of delays to prevent discharge is related to the energy and intensity of the treatment protocol; higher voltages will involve longer delays.

Electrical discharge events are very likely in PEF therapies that involve waveforms having voltages in the range of 500-5000 V to invoke their therapeutic effects, especially when using bipolar electrode arrangements. It may be appreciated that electrical discharge events can occur outside of this range depending on specific conditions, particularly when energy is delivered via bipolar electrodes. For these ranges of parameters, delays (e.g. cycle delays, etc.) of 50, 250, 500, or 1000 µs and beyond may be most appropriate at retaining the predominant degree of treatment effect while also preventing electrical arcing discharge.

Figures 7A, 7B:
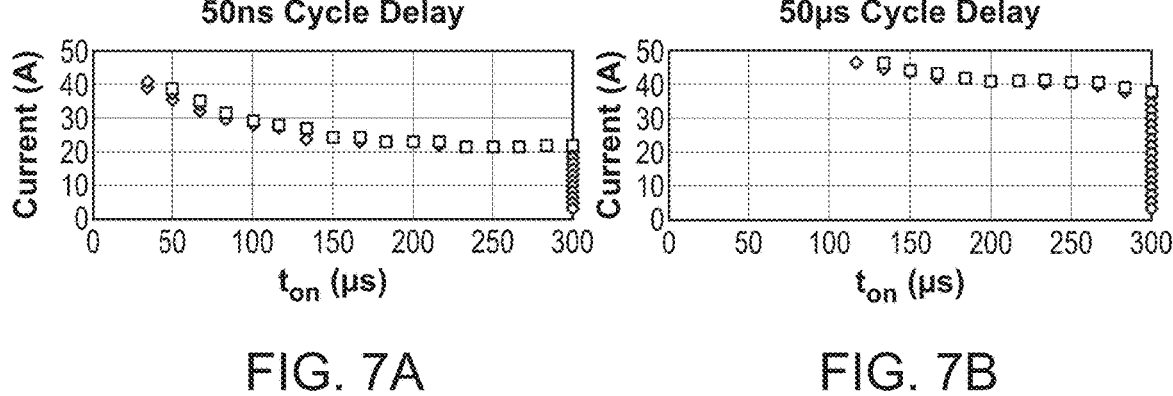
FIGS. 7A-7B illustrates an example comparison between the effects of different sized cycle delays on electrical discharge.

FIGS. 7A-7B illustrates an example comparison between the effects of different sized cycle delays on electrical discharge. Here, an energy delivery body 108 was immersed in a saline bath and delivered a PEF treatment until a visible electric discharge was encountered. The waveform was comprised of a plurality of pulses 12 forming a packet 20 having an on-time of 300 µs. This 300 µs on-time packet was delivered at progressively higher voltages until a visible electrical discharge event was encountered. After this, the on-time was decreased, and the voltage was continued to be increased until an electric discharge was again visible. FIG. 7A illustrates a waveform having a very small cycle delay (50 ns). FIG. 7B illustrates a waveform having a modest cycle delay (50 µs). Notably, the 50 µs cycle delay trial set shows an increase of 78% in electric current that may be delivered before an electric discharge was noted when compared to a very small, —50 ns, cycle delay. Thus, this modest cycle delay was shown to markedly increase the amount of energy that can be delivered by the electrode prior to an electric discharge. This cycle delay is well below the realm where a reduced efficacy in treatment effect may be encountered (depending on cell size and properties, most likely begins to occur in the 5-10 ms cycle delay range). This greater resilience to electrical arcing was demonstrated to remain for all packet on-times tested in this series.

It may be appreciated that the design of the energy delivery body 108 or the physical arrangements of the energy delivery bodies 108 also play a role. When the design or arrangement of the energy delivery bodies 108 encourage concentration of electric currents, such as smaller contact areas or regions of sharp boundaries on the energy delivery bodies 108, longer delays are utilized to mitigate electrical discharge events.

Thus, in some embodiments, when delivering PEF therapies in blood or any electrolytic fluid, adjacent to a target tissue, such as in cardiac or vascular clinical applications, electric discharge can be eliminated with the use of delays, such as cycle delays or other delays, in the range of 50 µs-10,000 µs, preferably 250 µs-1000 µs. It may be appreciated that in some embodiments delays are 50 µs, 100 µs, 150 µs, 200 µs, 250 µs, 300 µs, 400 µs, 500 µs, 600 µs, 700 µs, 800 µs, 900 µs, 1000 µs, in the range of 50-250 µs, 250-500 µs, 500-1000 µs, greater than 250 µs, greater than 500 µs, greater than 1000 µs, 1000-5,000 µs, 1000-10,000 µs, to name a few. In some embodiments, when delivering PEF to solid tissues, such as when the energy deliver body 108 is positioning into a target tissue, electric discharge can be eliminated with the use of delays, such as cycle delays or other delays, in the range of 100 µs-10,000 µs, preferably 250 µs-2000 µs. It may be appreciated that in some embodiments delays are 100 µs, 200 µs, 250 µs, 300 µs, 400 µs, 500 µs, 600 µs, 700 µs, 800 µs, 900 µs, 1000 µs, 1500 µs, 2000 µs, in the range of 250-500 µs, 250-1000 µs, 500-1000 µs, 1000-2000 µs, greater than 250 µs, greater than 500 µs, greater than 1000 µs, to name a few. In some embodiments, when delivering PEF to luminal targets (e.g. airways), such as when the energy delivery body 108 is positioned within the lumen of a target tissue having no conductive fluid, electric discharge can be eliminated with the use of delays, such as cycle delays or other delays in the range of 10 µs-10,000 µs, preferably 50 µs-500 µs. It may be appreciated that in some embodiments delays are 10 µs, 20 µs, 30 µs, 40 µs, 50 µs, 60 µs, 70 µs, 80 µs, 90 µs, 100 µs, 200 µs, 300 µs, 400 µs, 500 µs, in the range of 50-100 µs, 100-250 µs, 250-500 µs, 1000-10,000 µs, greater than 50 µs, greater than 250 µs, greater than 500 µs, greater than 1000 µs to name a few.

Cavity Formation

As mentioned, when electrical discharge does occur a pressure wave is generated that is apparent as an audible "popping" tone. When the discharge and the pressure wave is of sufficient intensity and repeated a sufficient number of times, the energy transferred and deposited into the tissue from this pressure wave can severely disrupt the tissue architecture and cells. The resulting effect is the accumulated generation of a defect or cavity within the tissue at the regions near the electrode, which experience the strongest intensity of these effects.

By incorporating delays between the energized portions of the waveform, such as within a PEF packet, time is permitted for resolution of physical effects at a molecular level before these effects accumulate into a pressure wave capable of generating a tissue cavity. This results in a more distributed deposition of energy into the tissue, reducing or eliminating the pressure waves that occur as a result of PEF therapies. Thus, the introduction of cycle delays and other delays into the waveform can be used to mitigate or eliminate the generation of cavities. This can be harnessed to increase the predictability of the treatment effect outcome, and also be used to eliminate the dangers associated with the cavity formation, such as the disruption of vasculature integrity, fistula formation, or damage to other sensitive tissues.

Figures 8A, 8B:
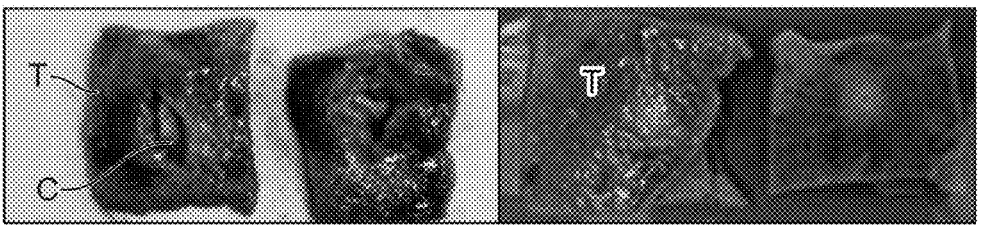
FIGS. 8A-8B illustrate the effects of identical pulsed electric field treatment protocols, apart from different cycle delays, delivered to liver tissue.

FIGS. 8A-8B illustrate the effects of identical PEF treatment protocols, apart from different cycle delays, delivered to liver tissue T. FIG. 8A illustrates the result of using a waveform having a cycle delay of approximately 50 ns which resulted in significant tissue cavity C formation. FIG. 8B illustrates the result of using the same waveform but with a cycle delay of approximately 1000 µs. Thus, the same amount of energy is delivered. As shown, such a longer cycle delay is able to entirely eliminate the large cavities formed in the liver tissue T.

One collateral benefit of cavity elimination is more efficient energy deposition into tissue by potentially eliminating gaps at the tissue-electrode interface. This could result in the generation of larger treatment effects.

In some embodiments, when delivering PEF to solid tissues, such as when the energy deliver body 108 is positioning into a target tissue, cavity formation can be eliminated with the use of delays, such as cycle delays or other delays, in the range of 100 µs-10,000 µs, preferably 250 µs-2000 µs. It may be appreciated that in some embodiments, delays are 100 µs, 200 µs, 250 µs, 300 µs, 400 µs, 500 µs, 600 µs, 700 µs, 800 µs, 900 µs, 1000 µs, 1500 µs, 2000 µs, in the range of 250-500 µs, 250-1000 µs, 500-1000 µs, 1000-2000 µs, greater than 250 µs, greater than 500 µs, greater than 1000 µs, to name a few.

Muscle Contraction

Cells and tissues closest to the energy delivery bodies 108 are the most intensely affected cells and tissue in PEF therapies. It is possible to subject these cells and tissues to the accumulated generation of treatment effects while avoiding or preventing the generation of action potentials in distant motor neurons and skeletal muscle (as well as cardiac and smooth muscle). This is achieved with the use of biphasic pulses and is further achieved with delays within the waveform. It has been found that the charging and relaxation characteristics of these distant motor neurons involve longer duration cycle delays to prevent their occurrence. For example, 10 ms, 20 ms, 30 ms, 40 ms, or 50 ms cycle delays may be used.

In some instances, desired cycle delays are determined at least in part by numerical simulations of action potential generation. In some embodiments, a model is utilized that is based on an array of Nodes of Ranvier between myelinated regions of axons. Referring to FIG. 9, Nodes of Ranvier NR, also known as myelin-sheath gaps, occur along a myelinated axon MA where the axolemma AA (axon membrane) is exposed to the extracellular space. Nodes of Ranvier NR are uninsulated and highly enriched in ion channels, allowing them to participate in the exchange of ions required to regenerate the action potential. Nerve conduction in myelinated axons MA occurs in a manner in which the action potential seems to "jump" from one node NR to the next along the axon MA. This results in faster conduction of the action potential.

Referring to FIG. 10, the myelinated axon MA regions are modeled as resistors for the intracellular environment. Each node NR is comprised of a membrane for the cell that separates the intracellular environment from the extracellular environment and is modeled as a capacitor in parallel with a leakage resistor and voltage source. When exposed to an electric field, the myelinated axon MA begins charging along the capacitor. When the electric field is removed (e.g. the pulse is ceased for a delay period), the charge accumulation on the myelinated axon MA begins discharging. Thus, the ability for a PEF therapy to induce an action potential in motor neurons relates to the effective duty cycle of the PEF waveform.

This concept is conveyed in FIGS. 11A-11D. FIG. 11A illustrates an example PEF waveform 10 having no or low cycle delay 16 and FIG. 11B provides a schematic depiction of the charging 62 and discharging 64 behavior of a motor neuron. Two packets 20 of the waveform 10 are depicted, separated by an inter-packet delay 22. As the packet 20 is delivered, the motor neuron incrementally charges throughout the delivery. After a period of time, the accumulated transmembrane potential induces an action potential (indicated by dashed line 66). The motor neuron then begins discharging upon commencement of the inter-packet delay 22. This repeats for each later packet 20.

FIG. 11C illustrates an example PEF waveform 10 having larger cycle delay 16 than the waveform of FIG. 11A. FIG. 11D provides a schematic depiction of the charging 62 and discharging 64 behavior of the motor neuron. As the waveform 10 is delivered, the motor neuron incrementally charges throughout the delivery, however discharging begins upon commencement of the cycle delay 16. Thus, it is apparent that the inclusion of larger cycle delays 16 results in constraining the accumulated transmembrane potential below that which would induce an action potential (below the dashed line 66). For a given active period of energy delivery, a characteristic delay for that waveform and electric field intensity exists that prevents accumulated axon charge from reaching the threshold that induces an action potential.

Figure 12:
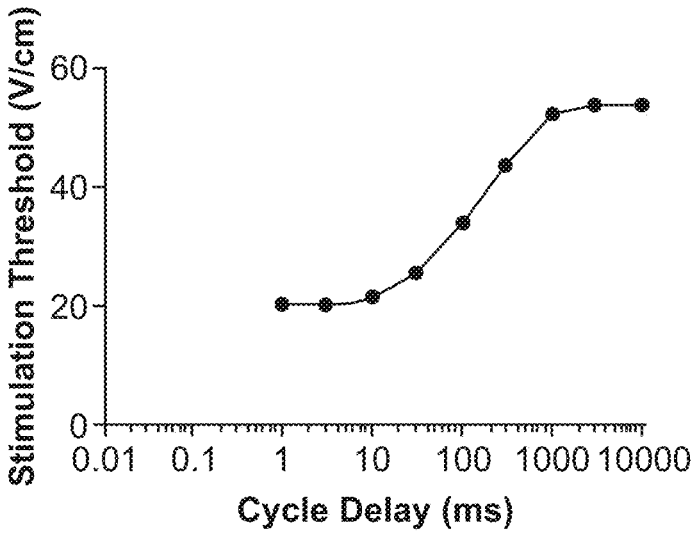
FIG. 12 illustrates the effect of cycle delay on muscle stimulation threshold.

Properties for the mathematical model are selected to mimic that of motor neuron axons. By utilizing the model, it is found that benefits of cycle delays 16 to mitigate muscle contractions begin occurring at cycle delays of 10 ms and plateau at cycle delays of 1 second, as illustrated in FIG. 12. Thus, this is the modeled effective range to limit muscle contraction. It should be noted that these ranges will change relative to the intensity, phase-behavior (monophasic or biphasic or varying asymmetry levels of biphasic), other parameters of the PEF waveform (total packet on-time, etc), geometry of the electrode arrangement (bipolar, multipolar, or monopolar), and the proximity of a given motor neuron to the PEF electrode(s) for whether an action potential is ultimately induced in the neuron. Muscle cells (skeletal, cardiac, smooth) will also have similar effects and characteristics affecting their susceptibility to contraction, though at different inherent sensitivities based on the inherent characteristics and specific properties of these cells.

Depending on the specifics of the PEF waveform, as cycle delays 16 are increased generally from 5 ms up to and beyond 10 ms, there is a chance that the total volume of tissue treated by the PEFs will begin to decrease. However, the closest cells to the energized electrode will still remain affected and thus treated by the tissue. Thus, although treatment effects will vary as cycle delays 16 begin ranging into the 10 s of milliseconds, it is still possible to generate meaningful treatment outcomes using cycle delays that will reduce or eliminate muscle contraction. Conversely, short to eliminated delays could be used to encourage additional muscle contraction, where desired.

In some embodiments, when delivering PEF to solid tissues, such as when the energy deliver body 108 is positioning into a target tissue, muscle contraction can be reduced or eliminated with the use of delays, such as cycle delays or other delays, in the range of 5 ms-100 ms, preferably 10-30 ms. In some embodiments, when delivering PEF to luminal targets (e.g. airways), such as when the energy delivery body 108 is positioned within the lumen of a target tissue having no conductive fluid, muscle contraction can be reduced or eliminated with the use of cycle delays in the range of 5 ms-100 ms, preferably 10-30 ms. In either case, it may be appreciated that in some embodiments delays are 5 ms, 10 ms, 25 ms, 30 ms, 40 ms, 50 ms, 60 ms, 70 ms, 80 ms, 90 ms, 100 ms, in the range of 5-10 ms, 10-20 ms, 20-30 ms, greater than 5 ms, greater than 10 ms, greater than 15 ms, greater than 30 ms, to name a few.

Temperature Rise

As described herein, introducing and manipulating delay periods between active periods of a PEF waveform distributes the energy deposition into the tissue over a longer period of time. This significantly affects the shape and amplitude of the temperature rise spike that characteristically occurs for PEF therapies during the pulse delivery period, particularly at the region very close to the electrode (tissue-electrode interface). This improves the safety of the treatment, reduces the chance for collateral tissue effects, and reduces the chances for electrical discharge events, including sparking or arc formation, by eliminating the potential for hot-spots in the tissue or fluid that would encourage arcing. Thus, introduction of cycle delays can be used to significantly improve treatment outcomes by attenuating the peak temperatures that occur.

Figure 13:
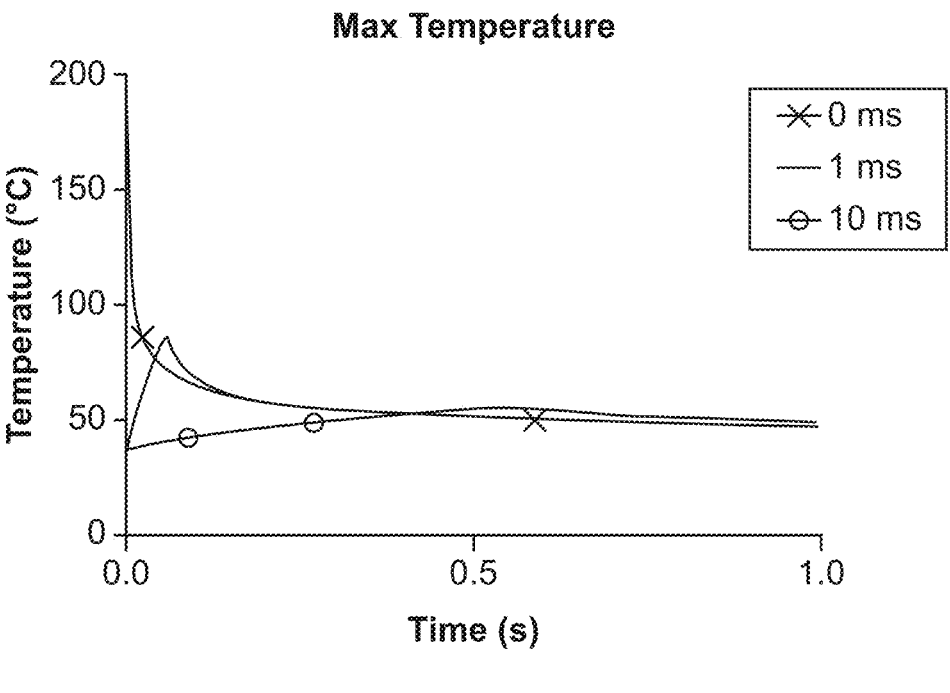
FIG. 13 illustrates amplitude and distribution of a temperature rise from a pulsed electric field protocol generated by a numerical simulation.
Figure 14A:
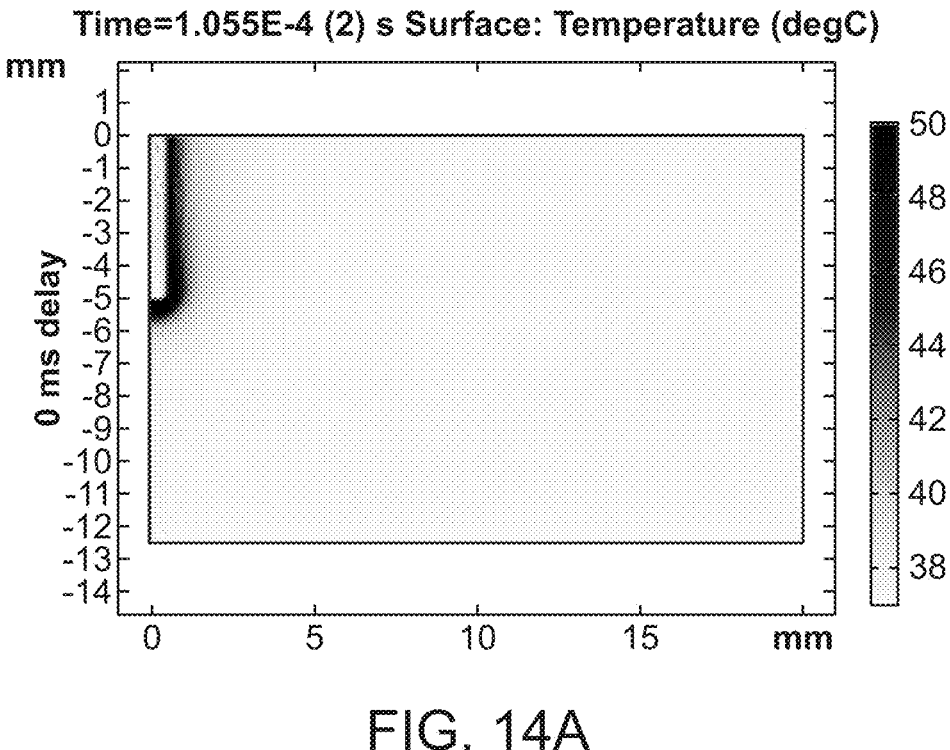
FIGS. 14A-14B illustrate the temperature distribution at the time of maximum temperature rise as related to FIG. 13.
Figure 14B:
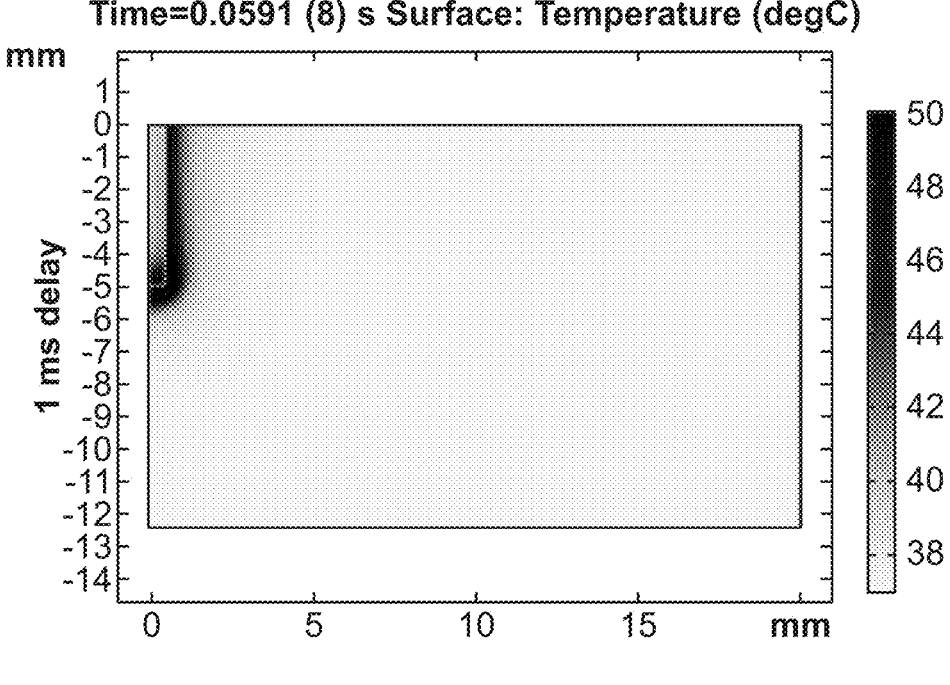

Referring to FIG. 13, calculation of the amplitude and distribution of a temperature rise from a PEF protocol can be generated by a numerical simulation. In this example, three PEF protocols are compared, each comprising a waveform 10 having a single packet 20 of biphasic pulses 12. A first PEF protocol includes no cycle delays, a second PEF protocol includes 1 ms cycle delays 16 and a third PEF protocol includes 10 ms cycle delays 16. As shown in FIG. 13, the general mm-scale distribution of temperatures exceeding 50° C. was comparable between the protocols having no cycle delays and 1 ms cycle delays. However, the instantaneous spike in max temperature at the tissue-electrode interface is dramatically different. The protocol having no cycle delay generated maximum temperatures of ~175° C., while the protocol having 1 ms cycle delays reached a peak temperature of ~80° C., and the protocol having 10 ms cycle delays muted the maximum temperature rise to ~55° C. The temperature distribution at the time of maximum temperature rise is illustrated in FIGS. 14A-14B, thus reflecting a different duration into the packet for the Oms delay (FIG. 14A) versus the 1 ms delay (FIG. 14B). Thus, the introduction and manipulation of cycle delays 16 induces a marked, scalable, effect on thermal effects that occur to the tissue.

It should be noted that these values are at the immediate tissue-electrode boundary, where maximum temperatures are encountered, followed by a very steep decline in temperature. Once the packet is completed, there is a steep decline in temperature as well. Thus, while these values indicate very high temperatures, they do not indicate that significant degrees of thermal damage would occur from the modeled PEF therapy at mm-scale distances into the tissue from the electrode. However, the mitigated temperature peaks would significantly reduce the potential generation of harmful thermal damage and protein denaturation in close proximity to the electrode, as well as reduce the chances of generating electrical discharge events. These are two of the key benefits for utilizing cycle delays in these procedures.

Thus, in some embodiments, when delivering PEF therapies in blood or any electrolytic fluid, adjacent to a target tissue, such as in cardiac or vascular clinical applications, peak temperatures can be reduced with the use of delays, such as cycle delays or other delays, in the range of 200 $\mu$s-20,000 $\mu$s, preferably 500 $\mu$s-10,000 $\mu$s. In some embodiments, when delivering PEF to solid tissues, such as when the energy deliver body 108 is positioning into a target tissue, peak temperatures can be reduced with the use of delays, such as cycle delays or other delays, in the range of 200 $\mu$s-20,000 $\mu$s, preferably 500 $\mu$s-10,000 $\mu$s. In either case, it may be appreciated that in some embodiments delays are 500 $\mu$s, 1000 $\mu$s, 2000 $\mu$s, 3000 $\mu$s, 4000 $\mu$s, 5000 $\mu$s, 6000 $\mu$s, 7000 $\mu$s, 8000 $\mu$s, 9000 $\mu$s, 10,000 $\mu$s, in the range of 200-500 $\mu$s, 500-1000 $\mu$s, 500-1000 $\mu$s, 1000-10,000 $\mu$s, 10,000-20,000 $\mu$s, greater than 200 $\mu$s, greater than 500 $\mu$s, greater than 1000 $\mu$s, to name a few.

In some embodiments, when delivering PEF to luminal targets (e.g. airways), such as when the energy delivery body 108 is positioned within the lumen of a target tissue having no conductive fluid, peak temperatures can be reduced with the use of delays, such as cycle delays or other delays, in the range of 100 $\mu$s-10,000 $\mu$s, preferably 200 $\mu$s-1000 $\mu$s. In either case, it may be appreciated that in some embodiments delays are 100 $\mu$s, 200 $\mu$s, 300 $\mu$s, 400 $\mu$s, 500 $\mu$s, 600 $\mu$s, 700 $\mu$s, 800 $\mu$s, 900 $\mu$s, 1000 $\mu$s, in the range of 100-200 $\mu$s, 100-500 $\mu$s, 500-1000 $\mu$s, 500-1000 $\mu$s, 1000-10,000 $\mu$s, greater than 200 $\mu$s, greater than 500 $\mu$s, greater than 1000 $\mu$s, to name a few.

Comparisons of Delay Ranges to Control Effects

Overall, the susceptibility and sensitivity for a given therapy to each secondary treatment effect, such as gas formation, electrical discharge, cavity formation, muscle contraction, and temperature rise, will vary. Table 1, below, summarizes the potential most applicable ranges of delays that may be used to mitigate these effects for various targeted tissue varieties. Notably, this table focuses on applications to mitigate the secondary effects, but there are other times when these effects may want to be encouraged, and thus a different range of delays may be applicable for a given therapeutic target.

TABLE 1

| Summary Table of Basic Cycle Delays | | | |
|---|---|---|---|
| Target | Electrode(s) Location | Objective | Cycle Delay General Range (Targeted Range) |
| Cardiac/Vascular | In blood, adjacent to target tissue | Eliminate gas formation | 100 $\mu$s-10 ms (250-1000 $\mu$s) |
| | | Eliminate electric discharge | 50 $\mu$s-10 ms (250-1000 $\mu$s) |
| | | Increase treatment effect | 100 $\mu$s-10 ms (500 $\mu$s-5 ms) |
| | | Reduce peak temperatures | 200 $\mu$s-20 ms (500 $\mu$s-10 ms) |
| | | Reduce muscle contraction | 5 ms-100 ms (10-30 ms) |
| Solid Tissues | Placed into target tissue | Eliminate gas formation | 10 $\mu$s-1 ms (25-100 $\mu$s) |
| | | Eliminate electric discharge | 100 $\mu$s-10 ms (250-2000 $\mu$s) |
| | | Increase treatment effect | 100 $\mu$s-10 ms (500 $\mu$s-5 ms) |
| | | Eliminate cavity formation | 100 $\mu$s-10 ms (250-2000ps) |
| | | Reduce muscle contraction | 5 ms-100 ms (10-30 ms) |
| | | Reduce peak temperatures | 200 $\mu$s-20 ms (500 $\mu$s-10 ms) |
| Luminal Targets (airways, etc) | Within lumen of target tissue, no conductive fluid | Eliminate electric discharge | 10 $\mu$s-10 ms (50-500 $\mu$s) |
| | | Increase treatment effect | 100 $\mu$s-10 ms (500 $\mu$s-2 ms) |
| | | Reduce muscle contraction | 5 ms-100 ms (10-30 ms) |
| | | Reduce peak temperatures | 100 $\mu$s-10 ms (200 $\mu$s-1 ms) |

Thus, the inclusion and manipulation of various delays within PEF waveforms, particularly phase delays, cycle delays 16, and/or inter-packet delays 20, provides a powerful tool to dramatically improve treatment outcomes. This is achieved by eliminating or reducing the risks associated cavity formation) are provided given the particular scenario. Thus, it is apparent that delay values are dependent on a variety of factors related to the treatment protocol, however unifying concepts are elucidated as described herein-throughout.

TABLE 2

| Treatment Effect (depth) | Electrode shape | Circuit Type | Frequency kHz | Cycle Count | Packets | Amperage A | Calculated impedance ohms | Calculated Voltage, kV | Min Cyc delay to avoid bubbles, µs | Min Cyc delay to avoid arcing, µs | Min Cyc delay to avoid cavity, µs |
|---|---|---|---|---|---|---|---|---|---|---|---|
| ~5 mm | Focal tip | Monopolar | 400 | 45 | 12 | 19 | 100 | 1900 | 10 | 0 | 0 |
| ~6.5 mm | Focal tip | Monopolar | 400 | 45 | 21 | 22 | 100 | 2200 | 50 | 0 | 0 |
| ~8 mm | Focal tip | Monopolar | 400 | 45 | 30 | 25 | 100 | 2500 | 100 | 10 | 0 |
| ~10 mm | Focal tip | Monopolar | 400 | 45 | 30 | 30 | 100 | 3000 | 200 | 40 | 5 |
| ~8 mm | ½ surface area of Focal tip | Monopolar | 400 | 45 | 30 | 25 | 100 | 2500 | 200 | 20 | 10 |
| ~8 mm | Focal tip | Monopolar | Monophasic | 10 µs pulses, 10 cycs total | 30 | 15 | 100 | 1500 | 200 | 50 | 10 |
| ~10 mm | Focal tip | Monopolar | 200 | 20 | 30 | 22 | 100 | 2200 | 300 | 60 | 15 |

| Treatment Effect (width) | Electrode shape | Cicuit Type | Frequency kHz | Cycle count | Packets | Amperage A | Calculated impedance, ohms | Calculated Voltage, kV | Min Cyc delay to avoid bubbles, µs | Min Cyc delay to avoid arcing, µs | Min Cyc delay to avoid cavity, µs |
|---|---|---|---|---|---|---|---|---|---|---|---|
| ~1 cm | Needle | Monopolar | 400 | 40 | 100 | 22 | 150 | 3300 | 150 | 250 | 100 |
| ~2 cm | Needle | Monopolar | 100 | 10 | 100 | 22 | 150 | 3300 | 200 | 300 | 200 |
| ~3 cm | Needle | Monopolar | 80 | 8 | 100 | 26.7 | 150 | 4000 | 500 | 350 | 250 |
| ~1 cm | Needle | Monopolar | Monophasic | 10 µs pulses, 10 pulses total | 30 | 22 | 150 | 3300 | 50 | 25 | 10 | with secondary effects inherently caused by PEF therapies due to their nature of delivering high voltage electric pulses. These effects and benefits will apply regardless of the ranges of energy delivered in the waveform.

Thus, methods have been provided for controlling the secondary effects described above (e.g. gas formation, electrical discharge, muscle contraction, cavity formation and temperature rise) by controlling the duration and/or sequences of the constituent delays comprising a PEF treatment waveform contained within a cycle, series, packet, bundle, and/or activation that comprises what is collectively referred as the PEF waveform. It may be appreciated that although the examples and embodiments described herein focus on cycle delays 16, such information (e.g. example ranges for delay values, delay positions, number of delays, delay types, etc.) applies to any delay or combination of delays in a PEF waveform. Different types of delays, alone or in combination, may have the same effect by allowing a particular treatment effect while spreading out the energy delivery so as to mitigate various secondary effects. Thus, in some instances, manipulation of the timing of the energy delivery can be achieved in various ways with the same or similar outcome. Such effects may also be influence by electrode arrangements.

In an effort to provide sufficient examples of the various parameter combinations and outcome effects, Table 2 is provided hereinbelow. Table 2 provides a variety of combinations of treatment scenarios including electrode shape, circuit type, various parameter values and treatment effects. Example minimum values for cycle delays 16 to avoid various secondary effects (e.g. bubble formation, arcing, When reducing secondary effects, a primary principle underlying the use of these methods is that the delays are too short for complete discharge of accumulated charge distortions and/or recovery of the cell and organelles from the effects induced by the pulsed electric field (e.g., cell polarization, ATP depletion, etc). Thus, the repeated exposure of the targeted cells and tissue to a subsequent pulse, pulses, or series of pulses following the initial pulse or series of pulses results in the accumulation of injury to the cell, which ultimately increases its susceptibility to macromolecule transport (drugs, genetic material, etc) or results in its death (phagocytized, programmed cell death (parthanatos, pyroptosis, apoptosis, etc), necrosis, etc). Thus, the efficacy of the PEF therapy remains, at a consistent or altered extent, while the secondary effects are controlled.

Regarding these methods, the secondary effects may be reduced when delays are selected of sufficient duration whereby the induction of one or more of these behaviors is attenuated or prevented entirely. The effects may also be selectively encouraged, such as by using delays that are sufficiently low so as to foster their occurrence, especially when subsequent pulses within a portion of the waveform are of similar polarity arrangement. For example, in some instances, gas formation may be used to the advantage of the clinician via mechanisms such as physically disrupting the treatment environment. This may be used for purposes such as encouraging cell death, encouraging cell susceptibility to cytoactive agents, increasing mixing efficiency for infusions, and other potential uses. Therefore, at times it is desirable to control and encourage the formation of gas resulting from PEF therapies. However, for convenience, methods are primarily described herein to reduce the secondary (acellular) effects that may occur as a result of PEF therapies.

Waveform Lengths

When introducing and/or manipulating delays in a PEF waveform, various characteristics of the waveform may change. For example, when introducing or increasing cycle delays 16 in a packet 20 of a PEF waveform 10, the time to complete a packet will increase. It may be appreciated that such increase in packet duration or completion time will not increase packet on-time if the only change is an increase in delays. If a treatment is determined by delivering a particular number of packets 20, then the treatment time will increase with an increase in packet duration. Likewise, if inter-packet delays 26 are introduced or increased, the treatment time will also increase if the treatment comprises more than one packet.

In some instances, PEF waveforms without delays are delivered in pulses or packets that are 100 μs in length. When using a waveform having a base frequency of 400 kHz, the waveform has 400,000 cycles per second or one cycle is 2.5 μs long. Thus, in such instances the packet would comprise 40 cycles. If a cycle delay of 250 μs was introduced to such a packet (e.g. after each cycle within the packet), the packet length or packet duration would increase by 10,000 μs for a total packet duration of 10,100 μs. Table 3, below, illustrates the total packet time for a variety of introduced cycle delays (e.g. 250 μs, 500 μs, 1000 μs) in comparison to the packet duration for conventional PEF waveforms. In this table, a cycle delay is introduced after each cycle within the packet. This behavior is the same for phase-delays instead of cycle delays.

TABLE 3

| | # of packets | # cycles per packet | Total packet time (μs) | % on-time during total packet time |
|---|---|---|---|---|
| No delays | 1 | 40 | 100 | 100% |
| With 250 μs cycle delays | 1 | 10 | 2,525 | 0.99% |
| With 250 μs cycle delays | 1 | 25 | 6,313 | 0.99% |
| With 250 μs cycle delays | 1 | 50 | 12,625 | 0.99% |
| With 250 μs cycle delays | 1 | 100 | 25,250 | 0.99% |
| With 500 μs cycle delays | 1 | 10 | 5,025 | 0.50% |
| With 500 μs cycle delays | 1 | 25 | 12,563 | 0.50% |
| With 500 μs cycle delays | 1 | 50 | 25,125 | 0.50% |
| With 500 μs cycle delays | 1 | 100 | 50,250 | 0.50% |
| With 1000 μs cycle delays | 1 | 10 | 10,025 | 0.25% |
| With 1000 μs cycle delays | 1 | 25 | 25,063 | 0.25% |
| With 1000 μs cycle delays | 1 | 50 | 50,125 | 0.25% |
| With 1000 μs cycle delays | 1 | 100 | 100,250 | 0.25% |

In some embodiments, the inclusion of delays may increase the packet duration to a range of approximately 1000 to 200,000 microseconds, such as 2,000 μs, 5,000 μs, 10,000 μs, 20,000 μs, 25,000 μs, 30,000 μs, 40,000 μs, 50,000 μs, 60,000 μs, 70,000 μs, 80,000 μs, 90,000 μs, 100,000 μs, 110,000 μs, 120,000 μs, 130,000 μs, 140,000 μs, 150,000 μs, 160,000 μs, 170,000 μs, 180,000 μs, 190,000 μs, 200,000 μs, 1000-2000 μs, 1000-3000 μs, 1000-4000 μs, 1000-5000 μs, 1000-10,000 μs, 10,000-20,000 μs, 10,000-30,000 μs, 10,000-40,000 μs, 10,000-50,000 μs, 50,000-100,000 μs, 50,000-150,000 μs, 50,000-200,000 μs, greater than 10,000 μs, greater than 25,000 μs, greater than 50,000 μs, greater than 100,000 μs, greater than 200,000 μs to name a few.

It may be appreciated that Table 3 illustrates a small sample of combinations. Waveforms can include delays of any length, any number of delays and any type of delay (i.e. not limited to cycle delays). The delays may be consistent (e.g. same length, same position, etc., throughout waveform) or inconsistent (e.g. at least one of differing length, at least one in differing position or skipping position, differing between packets, differing between batches, etc.). Likewise, different base frequencies may be used. Further, any number of packets may be present in a waveform and any number of batches may be present, including no batches. In any case, the introduction of these types of delays significantly increases the packet time, as illustrated above. However, such increases have minimal impact on overall treatment time given the relatively small timescale of such increases. In other words, the tolerable limit for treatment times during a procedure is well beyond such increases due to inclusion of delays.

Delivery Devices and Systems

Typically, the energy is delivered with the use of systems and devices designed for the particular clinical application. With sufficient access, energy can be delivered to any target within the body of the patient. In some embodiments, the systems and devices are designed for endoluminal access to target tissue throughout the body, particularly in locations previously considered inaccessible to percutaneous approaches. Endoluminal access allows treatment of target tissue from within various lumens in the body. Lumens are the spaces inside of tubular-shaped or hollow structures within the body and include passageways, canals, ducts and cavities to name a few. Example luminal structures include blood vessels, esophagus, stomach, small and large intestines, colon, bladder, urethra, urinary collecting ducts, uterus, vagina, fallopian tubes, ureters, kidneys, renal tubules, spinal canal, spinal cord, and others throughout the body, as well as structures within and including such organs as the lung, heart and kidneys, to name a few. In some embodiments, the target tissue is accessed via the nearby luminal structure. In some instances, a treatment device 102 is advanced through various luminal structures or branches of a luminal system to reach the target tissue location. For example, when accessing a target tissue site via a blood vessel, the treatment device 102 may be inserted remotely and advanced through various branches of the vasculature to reach the target site. Likewise, if the luminal structure originates in a natural orifice, such as the nose, mouth, urethra or rectum, entry may occur through the natural orifice and the treatment device 102 is then advanced through the branches of the luminal system to reach the target tissue location. Alternatively, a luminal structure may be entered near the target tissue via cut-down or other methods. This may be the case when accessing luminal structures that are not part of a large system or that are difficult to access otherwise.

Target tissues include any of the luminal structures themselves, tissue nearby these luminal structures and any tissue accessible from these endoluminal approaches or other approaches, such as percutaneous, laparoscopic or open surgical approaches. These include cells, tissues and/or organs in the integumentary, skeletal, muscular, nervous, endocrine, cardiovascular, lymphatic, respiratory, digestive, urinary, and reproductive systems, to name a few. Examples cells, tissues and/or organs include luminal structures themselves, soft tissues throughout the body located near luminal structures and solid organs accessible from luminal structures, including but not limited to liver, pancreas, gall bladder, kidney, prostate, ovary, lymph nodes and lymphatic drainage ducts, underlying musculature, bony tissue, brain, eyes, thyroid, etc.

Examples of systems which may utilize waveform manipulations such as described herein include the tissue modification systems (e.g., energy delivery catheter systems) described in commonly assigned patent applications including international patent application number PCT/US2017/039527 titled "GENERATOR AND A CATHETER WITH AN ELECTRODE AND A METHOD FOR TREATING A LUNG PASSAGEWAY," international patent application number PCT/US2018/067501 titled "METHODS, APPARATUSES, AND SYSTEMS FOR THE TREATMENT OF DISORDERS", international patent application number PCT/US2018/067504 titled "OPTIMIZATION OF ENERGY DELIVERY FOR VARIOUS APPLICATIONS", international patent application number PCT/US2020/028844 titled "DEVICES, SYSTEMS AND METHODS FOR THE TREATMENT OF ABNORMAL TISSUE", and international patent application number PCT/US2020/042260 titled "TREATMENT OF THE REPRODUCTIVE TRACT WITH PULSED ELECTRIC FIELDS", international patent application number PCT/US2020/066205 titled "TREATMENT OF CARDIAC TISSUE WITH PULSED ELECTRIC FIELDS", all of which are incorporated herein by reference for all purposes.

Figure 15:
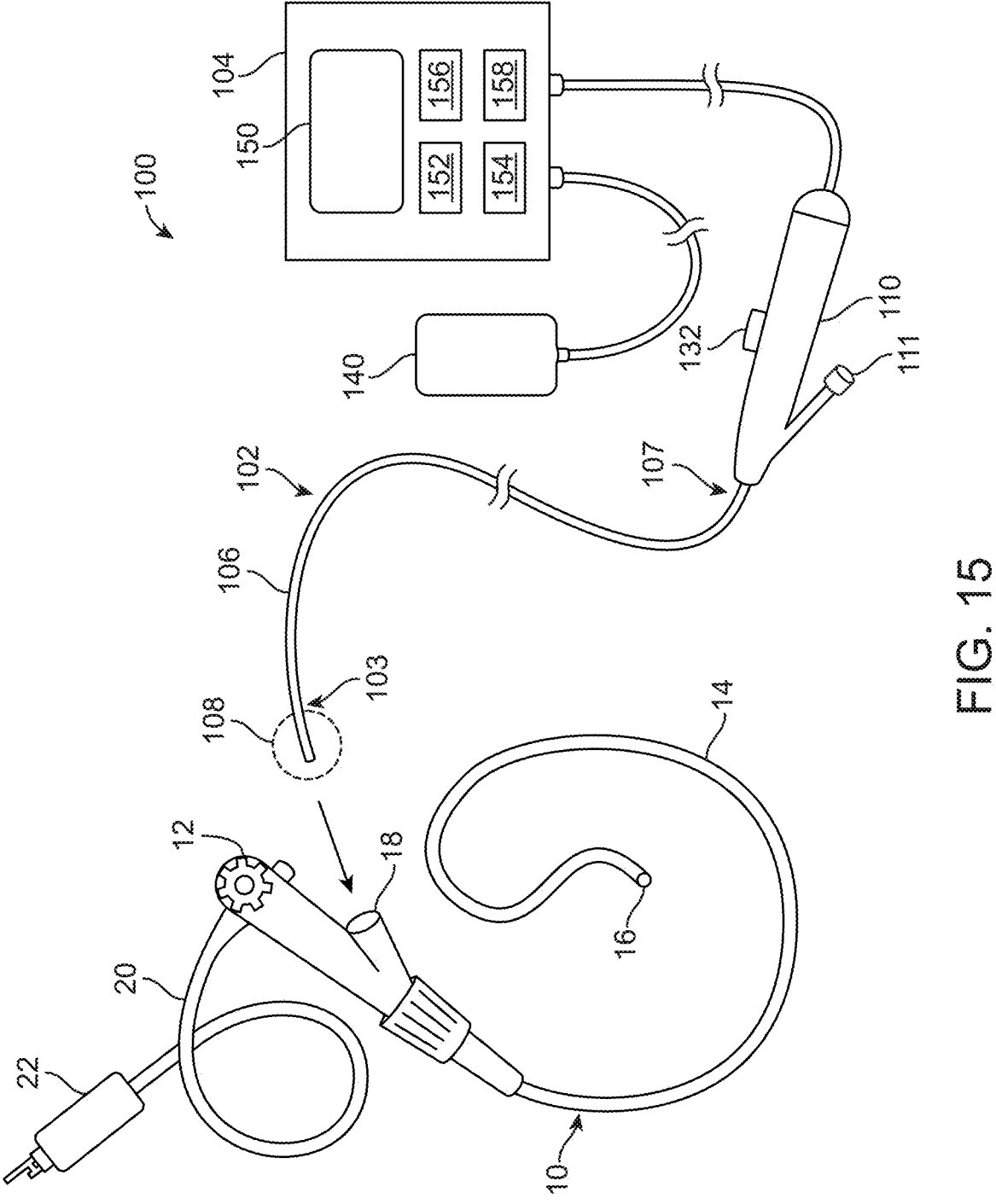
FIG. 15 provides an overview illustration of an example therapeutic system for use in delivering specialized pulsed electric field energy.

FIG. 15 provides an overview illustration of an example therapeutic system 100 for use in delivering the specialized PEF energy. In this embodiment, the system 100 comprises an elongate device 102 comprising a shaft 106 having a distal end 103 and a proximal end 107. The device 102 includes an energy delivery body 108 which is generically illustrated as a dashed circle near the distal end 103 of the shaft 106. It may be appreciated that the energy delivery body 108 may take a variety of forms having structural differences which encumber the drawing of a single representation, however individual example embodiments will be described and illustrated herein. The energy delivery body 108 may be mounted on or integral with an exterior of the shaft 106 so as to be externally visible. Or, the energy delivery body 108 may be housed internally within the shaft 106 and exposed by advancing from the shaft 106 or retracting the shaft 106 itself. Likewise, more than one energy delivery body 108 may be present and may be external, internal or both. In some embodiments, the shaft 106 is comprised of a polymer, such as an extruded polymer. It may be appreciated that in some embodiments, the shaft 106 is comprised of multiple layers of material with different durometers to control flexibility and/or stiffness. In some embodiments, the shaft 106 is reinforced with various elements such as individual wires or wire braiding. In either case, such wires may be flat wires or round wires. Wire braiding has a braid pattern and in some embodiments the braid pattern is tailored for desired flexibility and/or stiffness. In other embodiments, the wire braiding that reinforces the shaft 106 may be combined advantageously with multiple layers of material with different durometers to provide additional control of flexibility and/or stiffness along the length of the shaft.

In any case, each energy delivery body 108 comprises at least one electrode for delivery of the PEF energy. Typically, the energy delivery body 108 comprises a single delivery electrode and operates in a monopolar arrangement which is achieved by supplying energy between the energy delivery body 108 disposed near the distal end 103 of the device 102 and a return electrode 140 positioned upon the skin of the patient. It will be appreciated, however, that bipolar energy delivery and other arrangements may alternatively be used. When using bipolar energy delivery, the device 102 may include a plurality of energy delivery bodies 108 configured to function in a bipolar manner or may include a single energy delivery body 108 having multiple electrodes configured to function in a bipolar manner. The device 102 typically includes a handle 110 disposed near the proximal end 107. The handle 110 is used to maneuver the device 102, and typically includes an actuator 132 for manipulating the energy delivery body 108. In some embodiments, the energy delivery body 108 transitions from a closed or retracted position (during access) to an open or exposed position (for energy delivery) which is controlled by the actuator 132. Thus, the actuator 132 typically has the form of a knob, button, lever, slide or other mechanism. It may be appreciated that in some embodiments, the handle 110 includes a port 111 for introduction of liquids, agents, substances, tools or other devices for delivery through the device 102. Example liquids include suspensions, mixtures, chemicals, fluids, chemotherapy agents, immunotherapy agents, micelles, liposomes, embolics, nanoparticles, drug-eluting particles, genes, plasmids, and proteins, to name a few.

The device 102 is in electrical communication with a generator 104 which is configured to generate the PEF energy. In this embodiment, the generator 104 includes a user interface 150, one or more energy delivery algorithms 152, a processor 154, a data storage/retrieval unit 156 (such as a memory and/or database), and an energy-storage subsystem 158 which generates and stores the energy to be delivered. In some embodiments, the user interface 150 on the generator 104 is used to select the desired treatment algorithm 152. In other embodiments, the algorithm 152 is automatically selected by the generator 104 based upon information obtained by one or more sensors, which will be described in more detail in later sections. A variety of energy delivery algorithms may be used. In some embodiments, one or more capacitors are used for energy storage/delivery, however any other suitable energy storage element may be used. In addition, one or more communication ports are typically included.

As illustrated in FIG. 15, the distal end 103 of the device 102 is typically advanceable through a delivery device, such as an endoscope 10. Endoscopes 10 typically comprise a control body 12 attached to an elongate insertion tube 14 having a distal tip 16. The endoscope 10 has an interior lumen accessible by a port 18 into which the distal end 103 of the device 102 passes. The shaft 106 of the device 102 advanceable through the interior lumen and exits out of the distal tip 16. Imaging is achieved through the endoscope 10 with the use of a light guide tube 20 having an endoscopic connector 22 which connects to a light and energy source. The distal tip 16 of the endoscope may be outfitted with visualization technologies including but not limited to video, ultrasound, laser scanning, etc. These visualization technologies collect signals consistent with their design and transmit the signal either through the length of the shaft over wires or wirelessly to a video processing unit. The video processing unit then processes the video signals and displays the output on a screen. It may be appreciated that the endoscope 10 is typically specific to the anatomical location to which it is being used, such as gastroscopes (upper GI endoscopy, which includes the stomach, esophagus, and small intestine (duodenum)), colonoscopes (large intestine), bronchoscopes (lungs), laryngoscopes (larynx), cystoscopes (urinary tract), duodenoscopes (small intestine), enteroscopes (digestive system), ureteroscopes (ureter), hysteroscopes (cervix, uterus), etc. It may be appreciated that in other embodiments, the device 102 is deliverable through a catheter, sheath, introducer, needle or other delivery system.

Once a target tissue area has been approached endoluminally, energy can be delivered to the target tissue in a variety of ways. In one arrangement, an energy delivery body 108 is positioned within a body lumen and energy is delivered to the target tissue that is has entered the body lumen, through at least a portion of the lumen wall to target tissue either within the lumen wall and/or at least partially surrounding the lumen wall or through the lumen wall to target tissue outside and nearby the lumen wall. In another arrangement, the energy delivery body 108 is advanced through the lumen wall and inserted within or near target tissue outside of the lumen wall. It may be appreciated that such arrangements may be combined, involving at least two energy delivery bodies 108, one positioned within the body lumen and one extending through the wall of the body lumen. In some embodiments, each of the energy delivery bodies 108 function in a monopolar manner (e.g. utilizing a return electrode placed at a distance). In other embodiments, at least some of the energy delivery bodies 108 function in a bipolar manner (e.g. utilizing an energy delivery body 108 as a return electrode). Optionally, each of two energy delivery bodies 108 may be positioned on opposite sides of a lumen wall and function in a bipolar manner so as to treat tissue therebetween (e.g. within the lumen wall). Since the lumen itself is preserved throughout the treatment, these delivery options are possible and allow treatment of tissue in, on or nearby the lumen itself. Such delivery of therapy allows access to previously inaccessible tissue, such as tumors or diseased tissue that has invaded lumen walls or has wrapped at least partially around a body lumen, too close to be surgically removed or treated with conventional focal therapies. Many conventional focal therapies, such as treatment with thermal energy, damage or destroy the structure of the lumen walls due to thermal protein coagulation, etc.

The endoscopic approach also lends itself to monopolar energy delivery. As mentioned, monopolar delivery involves the passage of current from the energy delivery body 108 (near the distal end of the device 102) to the target tissue and through the patient to a return pad 140 positioned against the skin of the patient to complete the electric current circuit. Thus, in some embodiments, the device 102 includes only one energy delivery body 108 or electrode. This allows the device 102 to have a low profile so as to be positionable within smaller body lumens. This also allows deep penetration of tissue surrounding the energy delivery body 108. Likewise, when penetrating the lumen wall with such devices, only one penetration is needed per treatment due to the use of only one energy delivery body 108. It may be appreciated that additional penetrations may occur due to various device designs or treatment protocols, however in some embodiments, the monopolar delivery design reduces the invasiveness of the procedure, simplifies the device and treatment design and provides superior treatment zones in target tissue.

In contrast, bipolar delivery involves the passage of current through target tissue between two electrodes either on the same energy delivery body 108, on different energy delivery bodies 108 or by other arrangements. Most conventional energy therapies are bipolar and are typically percutaneous. Such therapies involve multiple penetrations of the skin, increasing discomfort, prolonging healing and adding complexity to the procedure. It may be appreciated that although the systems described herein may be utilized in a variety of formats, including bipolar and percutaneous arrangements, the device features will typically be combined in a manner that reduces overall invasiveness and provides better outcomes.

Figure 16:
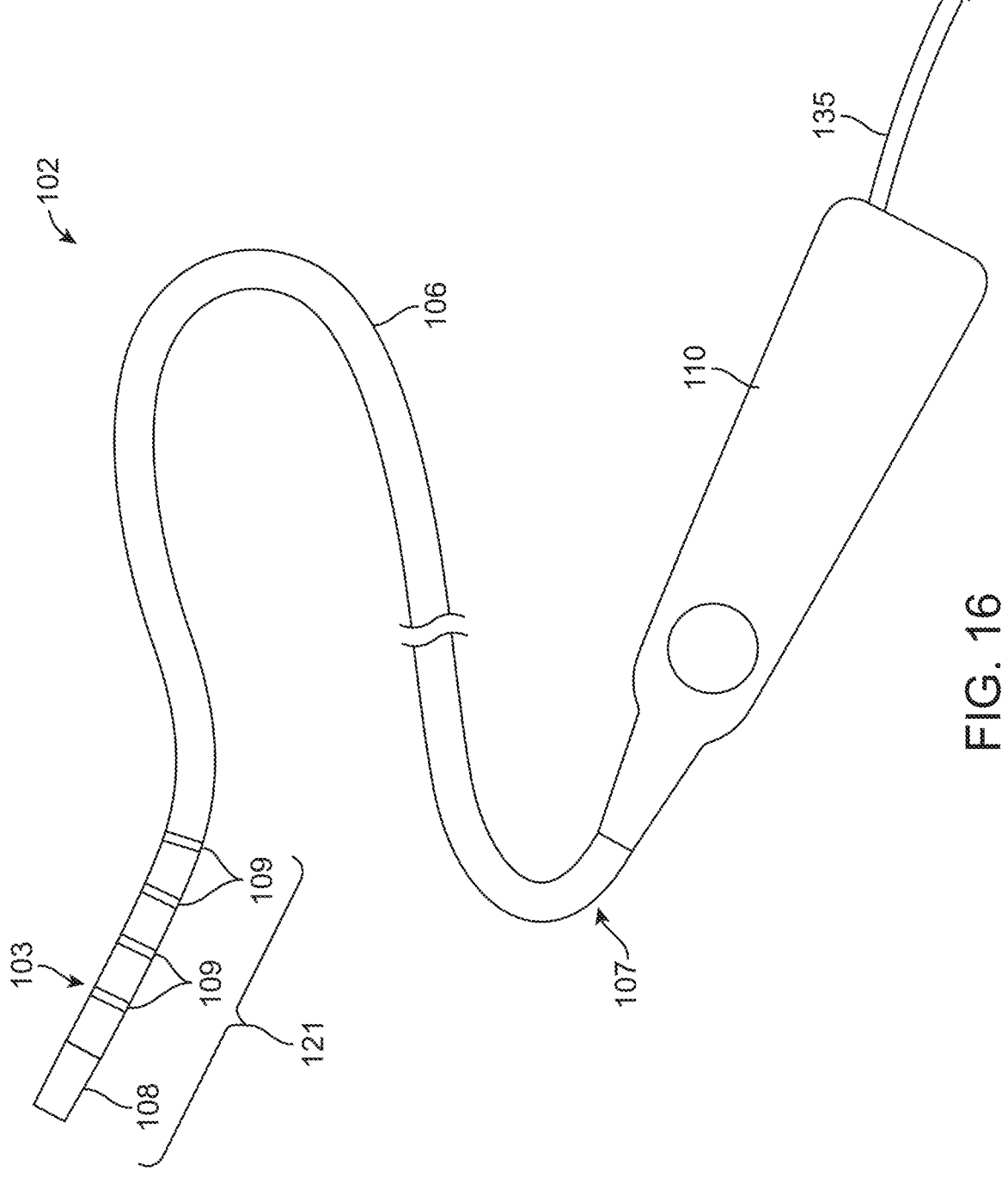
FIG. 16 illustrates another embodiment of a treatment device configured for use in delivering the specialized pulsed electric field energy, particularly configured to deliver focal therapy.

FIG. 16 illustrates another embodiment of a treatment device 102 configured for use in delivering the specialized PEF energy, particularly configured to deliver focal therapy. In this embodiment, the device 102 comprises an elongate shaft 106 having at least one energy delivery body 108 near its distal end 103 and a handle 110 near its proximal end 107. In this embodiment, the at least one energy delivery body 108 comprises a "focal electrode" having a cylindrical shape. The cylindrical shape has a circular, substantially flat face or curved face for positioning against tissue. In some embodiments, the device 102 has an overall length of 50-150 cm, preferably 100-125 cm, more preferably 110-115 cm. Likewise, in some embodiments, it has a 7 Fr outer diameter 3-15 Fr, preferably 4-12 Fr, more preferably 7-8.5 Fr. It may be appreciated that in some embodiments, the shaft 106 has a deflectable end portion 121 and optionally the deflectable end portion 121 may have a length of 50-105 mm resulting in curves with diameters ranging from approximately 15 to 55 mm. Deflection may be achieved by a variety of mechanism including a pull-wire which extends to the handle 110. Thus, the handle 110 is used to manipulate the device 102, particularly to steer the distal end 103 during delivery and treatment. Energy is provided to the device 102, and therefore to the at least one energy delivery body 108, via a cable 13 that is connectable to the generator 104.

Figures 17, 18:
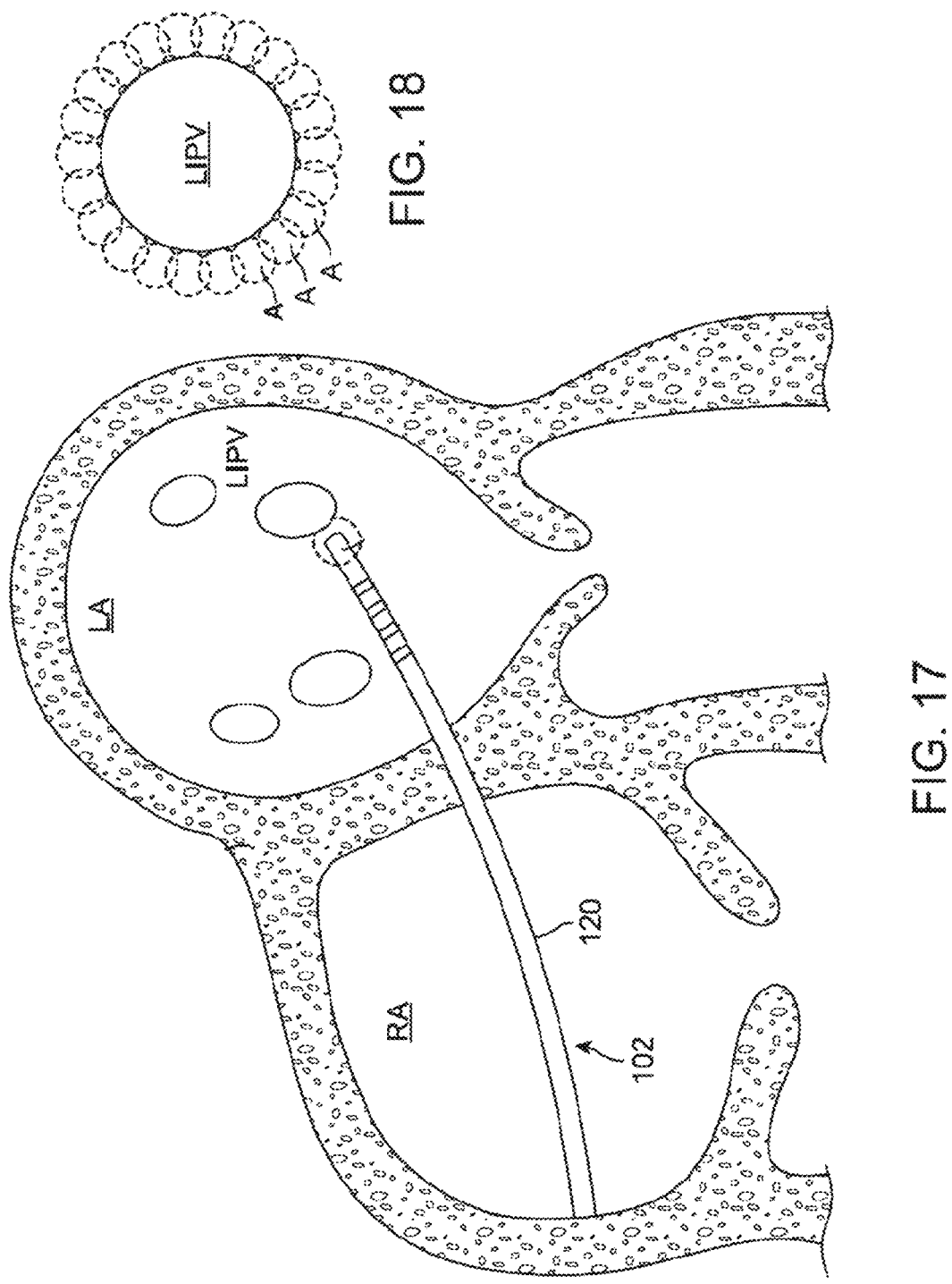
FIG. 17 illustrates a portion of the heart showing a cut-away of the right atrium and left atrium along with the treatment device of FIG. 16 disposed therein.
FIG. 18 illustrates treatment of the tissue surrounding the opening of the left inferior pulmonary vein in a point by point fashion with the use of the treatment device of FIG. 16.

In some embodiments, the treatment device 102 of FIG. 16 is utilized for treating cardiac tissues, particularly for treating arrhythmias, such as atrial fibrillation. FIG. 17 illustrates a portion of the heart H showing a cut-away of the right atrium RA and left atrium LA. The largest pulmonary veins are the four main pulmonary veins (right superior pulmonary vein RSPV, right inferior pulmonary vein RIPV, left superior pulmonary vein LSPV and left inferior pulmonary vein LIPV), two from each lung that drain into the left atrium LA of the heart H. In some embodiments, treatment of atrial fibrillation involves placing the treatment device 102 deep within the pulmonary vein and gradually withdrawing to the ostium, proximal to the mapping catheter. Mapping and treatment then commences.

In some embodiments, the tissue surrounding the opening of the left inferior pulmonary vein LIPV is treated in a point by point fashion with the use of the treatment device 102 (with assistance of mapping) to create a circular treatment zone around the left inferior pulmonary vein LIPV, as illustrated in FIG. 18. In some instances, specialized navigation software can be used to allow appropriate positioning of the treatment catheter 120. The delivery electrode 122 is positioned near or against the target tissue area, and energy is provided to the delivery electrode 122 so as to create a treatment area A. Since the energy is delivered to a localized area (focal delivery), the electrical energy is concentrated over a smaller surface area, resulting in stronger effects than delivery through an electrode extending circumferentially around the lumen or ostium. It also forces the electrical energy to be delivered in a staged regional approach, mitigating the potential effect of preferential current pathways through the surrounding tissue. These preferential current pathways are regions with electrical characteristics that induce locally increased electric current flow therethrough rather than through adjacent regions. Such pathways can result in an irregular electric current distribution around the circumference of a targeted lumen, which thus can distort the electric field and cause an irregular increase in treatment effect for some regions and a lower treatment effect in other regions. This may be mitigated or avoided with the use of focal therapy which stabilizes the treatment effect around the circumference of the targeted region. Thus, by providing the energy to certain regions at a time, the electrical energy is "forced" across different regions of the circumference, ensuring an improved degree of treatment circumferential regularity. FIG. 18 illustrates the repeated application of energy in point by point fashion around the left inferior pulmonary vein LIPV with the use of the treatment device 102 to create a circular treatment zone. As illustrated, in this embodiment each treatment area A overlaps an adjacent treatment area A so as to create a continuous treatment zone. The size and depth of each treatment area A may depend on a variety of factors, such as parameter values, treatment times, tissue characteristics, etc. It may be appreciated that the number of treatment areas A may vary depending on a variety of factors, particularly the unique conditions of each patient's anatomy and electrophysiology. In some embodiments, the number of treatment areas A include one, two, three, four, five, six, seven, eight, nine, ten, fifteen, twenty, twenty five, thirty or more.

When all the electrical connections between the atrium and the vein have been treated, there is electrical silence within the pulmonary vein, with only the far field atrial signal being recorded. Occasionally spikes of electrical activity are seen within the pulmonary vein with no conduction to the rest of the atrium; these clearly demonstrate electrical discontinuity of the vein from the rest of the atrial myocardium.

It may be appreciated that in various embodiments the treatment device 102 includes a variety of specialized features. For example, in some embodiments, the device 102 includes a mechanism for real time measurement of the contact force applied by the catheter tip to a patient's heart wall during an ablation procedure. In some embodiments, this mechanism is included in the shaft 120 and comprises a tri-axial optical force sensor which utilizes white light interferometry. By monitoring and modifying the applied force throughout the procedure, the user is able to better control the device 102 so as to create more consistent and effective lesions.

Referring back to FIG. 16, in some embodiments, the device 102 includes one or more additional electrodes 109 (e.g. ring electrodes) positioned along the shaft 120, proximal to the energy delivery body 108. In some embodiments, some or all of the electrodes 109 can be used for stimulating and recording (for electrophysiological mapping), so a separate cardiac mapping catheter is not needed when using device 102 for ablation.

In some embodiments, the device 102 includes a thermocouple temperature sensor, optionally embedded in the energy delivery body 108. Likewise, in some embodiments the device 102 includes a lumen which may be used for irrigation and/or suction. In some embodiments, the device 102 includes one or more sensors that can be used to determine temperature, impedance, resistance, capacitance, conductivity, permittivity, and/or conductance, to name a few. In some embodiments, one or more of the electrodes act as the one or more sensors. In other embodiments, the one or more sensors are separate from the electrodes. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It may be appreciated that in some embodiments the system 100 includes an automated treatment delivery algorithm that dynamically responds and adjusts and/or terminates treatment in response to inputs such as temperature, impedance at various voltages or AC frequencies, treatment duration or other timing aspects of the energy delivery pulse, treatment power and/or system status.

As mentioned previously, one or more energy delivery algorithms 152 are programmable, or can be pre-programmed, into the generator 104 for delivery to the patient P. The one or more energy delivery algorithms 152 specify electric signals which provide energy delivered to the walls of the heart which are non-thermal (e.g. below a threshold for thermal ablation; below a threshold for inducing coagulative thermal damage), reducing or avoiding inflammation, and/or preventing denaturation of stromal proteins in the luminal structures. In general, the algorithm 152 is tailored to affect tissue to a pre-determined depth and/or volume and/or to target specific types of cellular responses to the energy delivered.

Figures 19A, 19B:
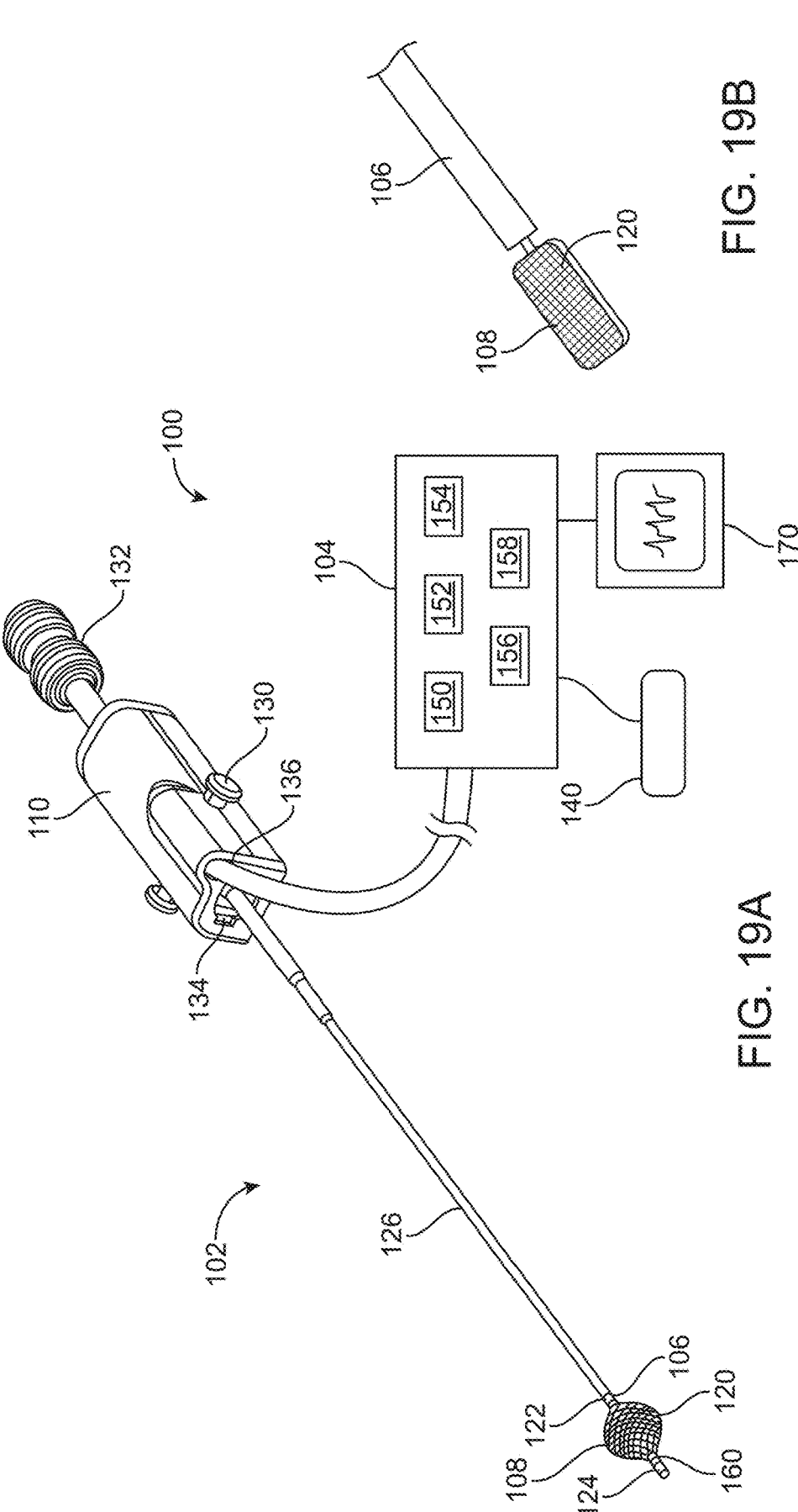
FIG. 19A-19B illustrate another embodiment of a therapeutic energy delivery catheter or device.

FIG. 19A illustrates another embodiment of a therapeutic energy delivery catheter or device 102. In this embodiment, the device 102 has an elongate shaft 106 with at least one energy delivery body 108 near its distal end and a handle 110 at its proximal end. The device 102 is connectable to a generator 104 as part of a treatment system 100. Connection of the device 102 to the generator 104 provides electrical energy to the energy delivery body 108, among other features. In this embodiment, the energy delivery body 108 includes a plurality of wires or ribbons 120, constrained by a proximal end constraint 122 and a distal end constraint 124, and forms a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. It may be appreciated that a variety of other designs may be used. For example, FIG. 19B illustrates an energy delivery body 108 having a paddle shape. In this embodiment, the energy delivery body 108 is comprised of a plurality of wires or ribbons 120 arranged so as to form a flat pad or paddle. Such an energy delivery body 108 is flexible so as to be retracted into the shaft 106. Referring back to FIG. 19A, in this embodiment the energy delivery body 108 is self-expandable and delivered to a targeted area in a collapsed configuration. This collapsed configuration can be achieved, for example, by placing a sheath 126 over the energy delivery body 108. The instrument shaft 106 (within the sheath 126) terminates at the proximal end constraint 122, leaving the distal end constraint 124 essentially axially unconstrained and free to move relative to the shaft 106 of the device 102. Advancing the sheath 126 over the energy delivery body 108 allows the distal end constraint 124 to move forward, thereby lengthening/collapsing and constraining the energy delivery body 108.

As shown in this example, the device 102 includes a handle 110 at its proximal end. In some embodiments, the handle 110 is removable, such as by pressing a handle removal button 130. In this embodiment, the handle 110 includes an energy delivery body manipulation knob or actuator 132 wherein movement of the actuator 132 causes expansion or retraction/collapse of the basket-shaped electrode. In this example, the handle 110 also includes a working port snap 134 for optional connection with an endoscope or other type of visualization device and a cable plug-in port 136 for connection with the generator 104. It may be appreciated that a variety of types of visualization may be used, including angiography (optionally including markers), computed tomography, optical coherence tomography, ultrasound, and direct video visualization, to name a few.

In this embodiment, the therapeutic energy delivery device 102 is connectable with the generator 104 along with a dispersive (return) electrode 140 applied externally to the skin of the patient P. Thus, in this embodiment, monopolar energy delivery is achieved by supplying energy between the energy delivery body 108 disposed near the distal end of the device 102 and the return electrode 140. It will be appreciated, however, that bipolar energy delivery and other arrangements may alternatively be used. When using bipolar energy delivery, the therapeutic energy delivery device 102 may differ in overall design, such as to include a plurality of energy delivery bodies 108, or may appear similar in overall design, such as to include a single energy delivery body 108 which is configured to function in a bipolar manner. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can spread the treatment effect over a larger, shallower surface area thus requiring a lower voltage to achieve the treatment effect, compared to monopolar. Likewise, this lower voltage may be used to reduce the depth of penetration.

As mentioned previously, one or more energy delivery algorithms 152 are programmable, or can be pre-programmed, into the generator 104 for delivery to the patient. The one or more energy delivery algorithms 152 specify electric signals which provide energy delivered to the tissue that are non-thermal (e.g. below a threshold for thermal ablation; below a threshold for inducing coagulative thermal damage), reducing or avoiding inflammation, and/or preventing denaturation of stromal proteins in the luminal structures. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the device 102 (particularly the one or more energy delivery bodies 108), and/or the choice of monopolar or bipolar energy delivery. Typically, depths of up to 0.01 cm, up to 0.02 cm, 0.01-0.02 cm, up to 0.03 cm, 0.03-0.05 cm, up to 0.05 cm, up to 0.08 cm, up to 0.09 cm, up to 0.1 cm, up to 0.2 cm, up to 0.5 cm, up to 0.7 cm, up to 1.0 cm, up to 1.5 cm, up to 2.0 cm, up to 2.5 cm, up to 3.0 cm, up to 3.5 cm, up to 4.0 cm, up to 4.5 cm, or up to 5.0 cm, to name a few. These depths may be larger for circumferentially focal targets, or they may exist for entire circumferential depths through a lumen and parenchymal tissue.

Figures 20A, 20B:
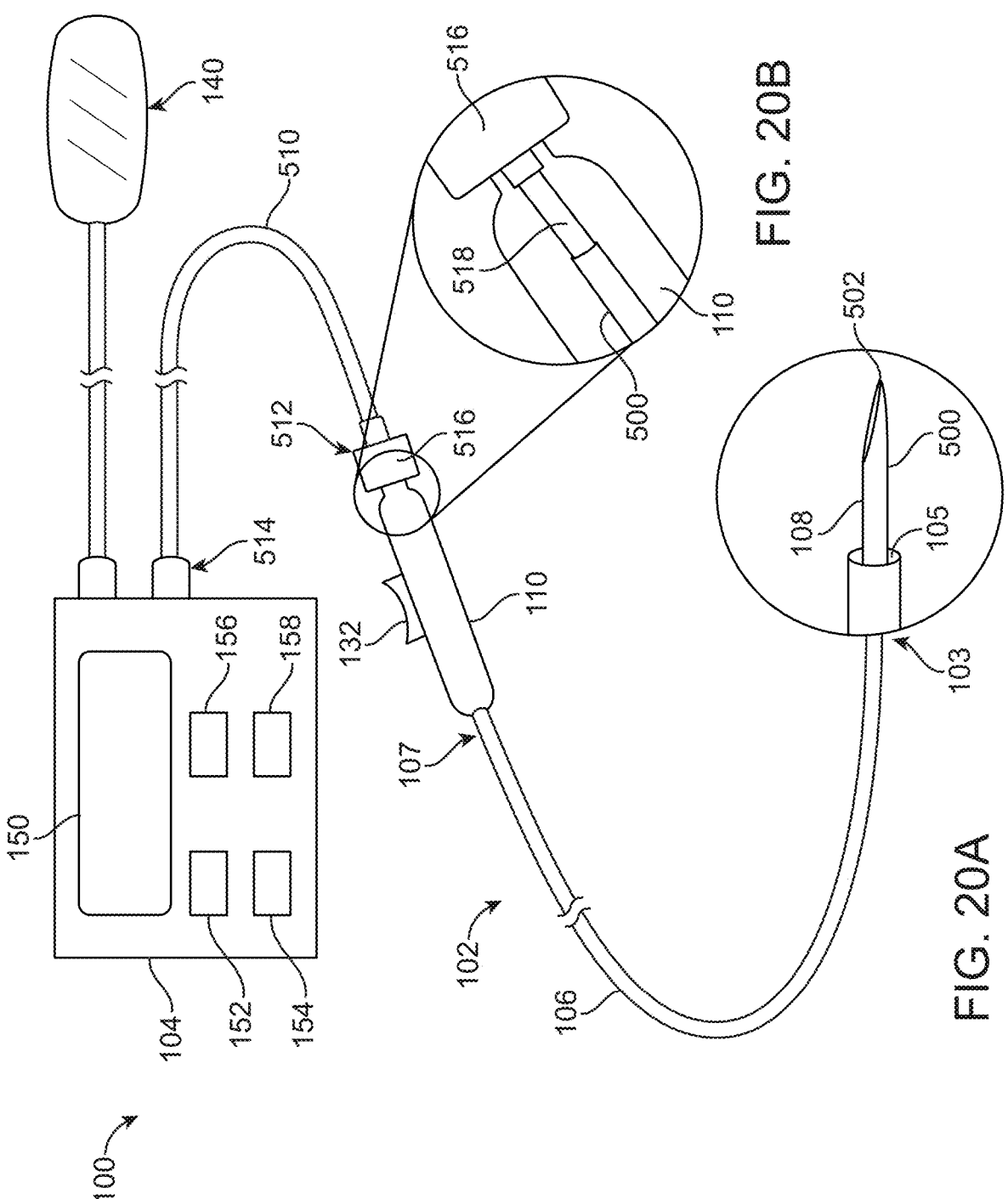
FIGS. 20A-20B illustrate another embodiment of a treatment system.

FIGS. 20A-20B illustrate another embodiment of a treatment system 100. Here, the system 100 is configured to treat target tissue that is located at least partially outside of a body lumen wherein treatment may benefit from originating the treatment energy at a distance from the body lumen. In this embodiment, the system 100 comprises an energy delivery device 102 connectable with a generator 104. It may be appreciated that many of the system components described above are utilized in this embodiment of the system 100, such as particular aspects of the device 102, generator 104 and other accessories. Therefore, such description provided above is applicable to the system 100 described herein below. The main differences are related to the energy delivery body 108.

Here, the device 102 comprises a shaft 106 having a distal end 103, a proximal end 107 and at least one lumen 105 extending at least partially therethrough. Likewise, the device 102 also includes at least one energy delivery body 108. In this embodiment, an energy delivery body 108 has the form of a probe 500 that is disposed within the lumen 105 of the shaft 106. The probe 500 has a probe tip 502 that is advanceable through the lumen 105 and extendable from the distal end 103 of the shaft 106 (expanded in FIG. 20A to show detail). In this embodiment, the tip 502 has a pointed shape configured to penetrate tissue, such as to resemble a needle. Thus, in this embodiment, the probe tip 502 is utilized to penetrate the lumen wall W and surrounding tissue so that it may be inserted into the target tissue external to the body lumen. Thus, the probe 500 has sufficient flexibility to be endoluminally delivered yet has sufficient column strength to penetrate the lumen wall W and target tissue. In some embodiments, the device 102 has markings to indicate to the user the distance that the probe tip 502 has been advanced so as to ensure desired placement.

In some embodiments, the probe extends from the distal end 103 of the shaft 106 approximately less than 0.5 cm, 0.5 cm, 1 cm, 2 cm, 3 cm, 4 cm, 5 cm, 6 cm, 7 cm, 8 cm or more than 8 cm. In some embodiments, the probe extends 1-3 cm or 2-3 cm from the distal end of the shaft 106. In some embodiments, the probe is 18 gauge, 19 gauge, 20 gauge, 21 gauge, 22 gauge, 23 gauge, 24 gauge, or 25 gauge. In some embodiments, the probe 500 is comprised of a conductive material so as to serve as an electrode. Thus, the electrode would have the size of the exposed probe. Example materials include stainless steel, nitinol, cobalt-chromium alloy, copper, and gold. Thus, in these embodiments, the PEF energy is transmittable through the probe 500 to the probe tip 502. Consequently, the shaft 106 is comprised of an insulating material or is covered by an insulating sheath. Example insulating materials include polyimide, silicone, polytetrafluoroethylene, and polyether block amide. The insulating material may be consistent or varied along the length of the shaft 106 or sheath. Likewise, in either case, the insulating material typically comprises complete electrical insulation. However, in some embodiments, the insulating material allows for some leakage current to penetrate.

When the probe 500 is energized, the insulting shaft 106 protects the surrounding tissue from the treatment energy and directs the energy to the probe tip 502 (and any exposed portion of the probe 500) which is able to deliver treatment energy to surrounding tissue. Thus, the tip 502 acts as a delivery electrode and its size can be selected based on the amount of exposed probe 500. Larger electrodes can be formed by exposing a greater amount of the probe 500 and smaller electrodes can be formed by exposing less. In some embodiments, the exposed tip 502 (measured from its distal end to the distal edge of the insulating shaft) during energy delivery has a length of 0.1 cm, 0.2 cm, 0.3 cm, 0.4 cm, 0.5 cm, 0.6 cm, 0.7 cm, 0.8 cm, 0.9 cm, 1 cm, 2 cm, 3 cm, greater than 3 cm, up to 8 cm, less than or equal to 0.1 cm, less than or equal to 0.3 cm, less than or equal to 0.5 cm, less than or equal to 1 cm, 0.2-0.3 cm, 0.1-0.5 cm, 0.1-1 cm, and all ranges and subranges therebetween. In addition to changing the size of the electrode, the tip 502 is retractable into the shaft 106 to allow for atraumatic endoscopic delivery and is then advanceable as desired to reach the target tissue. In this embodiment, advancement and retraction are controlled by an actuator 132 (e.g. knob, button, lever, slide or other mechanism) on a handle 110 attached to the proximal end 107 of the shaft 106. It may be appreciated that the shaft 106 itself may be advanced toward the target tissue, with or without advancing the probe from the distal end 103 of the shaft 106. In some embodiments, the distal end of the shaft 106 is advanced up to 20 cm into the tissue, such as from an external surface of a luminal structure or from an external surface of the body of the patient.

The handle 110 is connected to the generator 104 with the use of a specialized energy plug 510. The energy plug 510 has a first end 512 that connects to the handle 110 and a second end 514 the connects to the generator 104. The connection of the first end 512 with the handle 110 is expanded for detail in FIG. 20B. In this embodiment, the first end 512 has an adapter 516 that includes a connection wire 518 extending therefrom. The connection wire 518 is insertable into the proximal end of the probe 500 within the handle 110. This allows the energy to be transferred from the generator 104, through the connection wire 518 to the probe 500. Thus, the probe 500 is able to be electrified throughout its length, however only the exposed tip 502 delivers energy to the tissue due to the presence of the insulated shaft 106.

The devices, systems and methods described herein may be used on their own or in combination with other treatments. Such combinatory treatment may be applicable to cancer treatment in particular. For example, the PEF treatment described herein may be used in combination with a variety of non-surgical therapies, neoadjuvant and adjuvant therapies such as radiotherapy, chemotherapy, targeted therapy/immunotherapy, focal therapy, gene therapy, plasmid therapy, to name a few. Example focal therapies include microwave ablation, radiofrequency ablation, cryoablation, high intensity focused ultrasound (HIFU), and other pulsed electric field ablation therapies. Such combination may condition the tissue for improved responsiveness and in some cases a synergistic response that is greater than either of the therapies alone. In addition, the PEF treatments described herein may lead to an abscopal effect due to the nature of the therapy.

Energy Algorithms

The PEF energy is provided by one or more energy delivery algorithms 152. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time or inter-phase delay between polarities in biphasic pulses, dead time or cycle delay between biphasic cycles, and rest time or inter-packet delay between packets. In some embodiments, there is a fixed rest period between packets and in other embodiments packets are gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 21A:
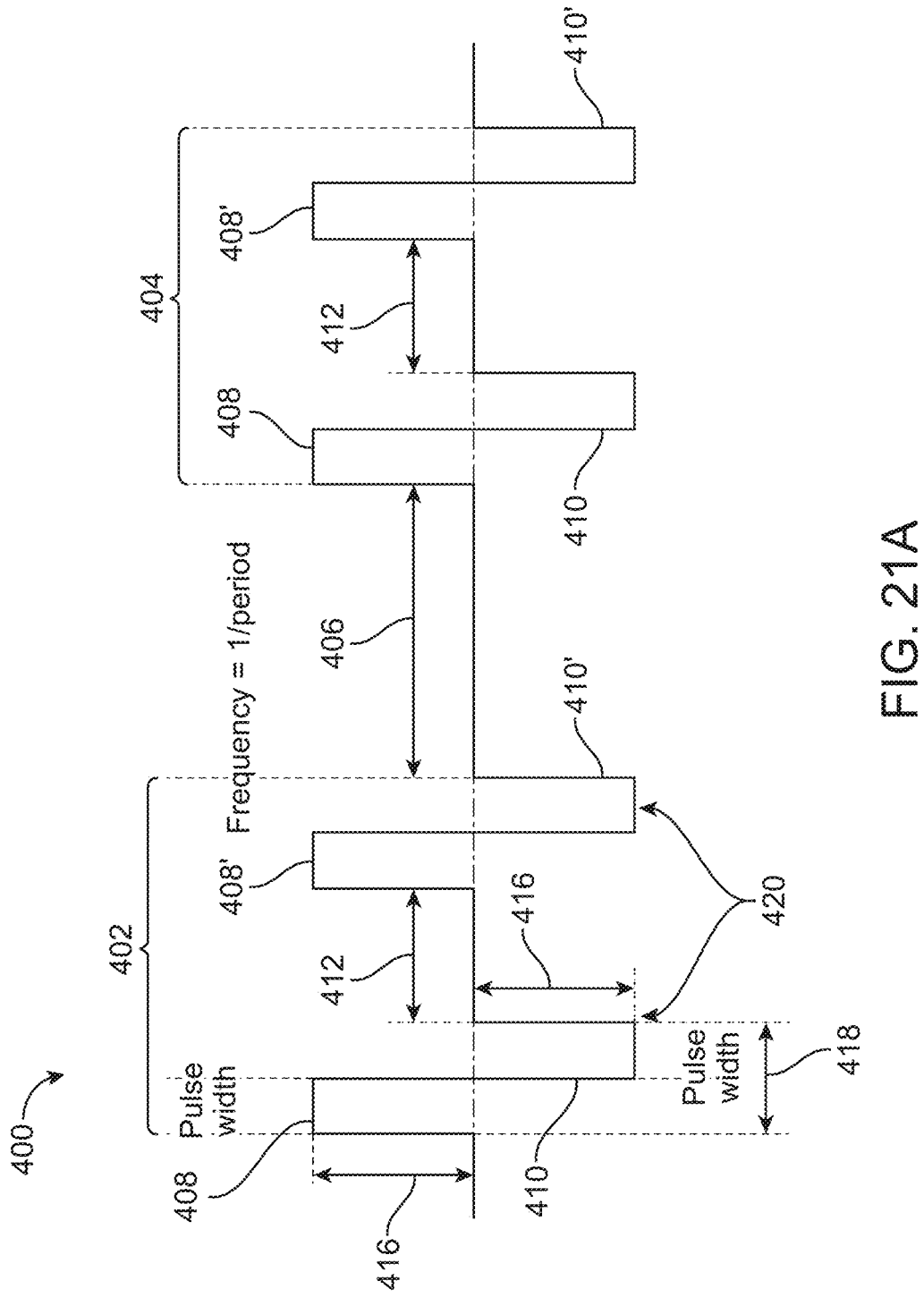
FIG. 21A illustrates an embodiment of a waveform of a signal prescribed by an energy delivery algorithm.

FIG. 21A illustrates an embodiment of a waveform 400 of a signal prescribed by an energy delivery algorithm 152. Here, two packets are shown, a first packet 402 and a second packet 404, wherein the packets 402, 404 are separated by an inter-packet delay or rest period 406. In this embodiment, each packet 402, 404 is comprised of a first biphasic cycle (comprising a first positive pulse peak 408 and a first negative pulse peak 410) and a second biphasic cycle (comprising a second positive pulse peak 408' and a second negative pulse peak 410'). The first and second biphasic pulses are separated by a cycle delay or dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave.

A. Voltage

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 3500 V to 4000 V, about 3500 V to 5000 V, about 3500 V to 6000 V, including all values and subranges in between including about 250 V, 500 V, 1000 V, 1500 V, 2000V, 2500 V, 3000 V, 3500 V, 4000 V, 4500 V, 5000 V, 5500 V, 6000 V to name a few. Voltages delivered to the tissue may be based on the setpoint on the generator 104 while either taking in to account the electrical losses along the length of the device 102 due to inherent impedance of the device 102 or not taking in to account the losses along the length, i.e., delivered voltages can be measured at the generator or at the tip of the instrument.

It may be appreciated that the set voltage 416 may vary depending on whether the energy is delivered in a monopolar or bipolar fashion. In bipolar delivery, a lower voltage may be used due to the smaller, more directed electric field. The bipolar voltage selected for use in therapy is dependent on the separation distance of the electrodes, whereas the monopolar electrode configurations that use one or more distant dispersive pad electrodes may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1.3 mm), if the separation distance is changed from 1 mm to 1.2 mm, this would result in a necessary increase in treatment voltage from 300 to about 360 V, a change of 20%.

B. Frequency

It may be appreciated that the number of biphasic cycles per second of time is the frequency when a signal is continuous. In some embodiments, biphasic pulses are utilized to reduce undesired muscle stimulation, particularly cardiac muscle stimulation. In other embodiments, the pulse waveform is monophasic and there is no clear inherent frequency. Instead, a fundamental frequency may be considered by doubling the monophasic pulse length to derive the frequency. In some embodiments, the signal has a frequency in the range 100 kHz-1 MHz, more particularly 100 kHz-1000 kHz. In some embodiments, the signal has a frequency in the range of approximately 100-600 kHz which typically penetrates the lumen wall so as to treat or affect particular cells somewhat deeply positioned, such as sub-mucosal cells or smooth muscle cells. In some embodiments, the signal has a base frequency or fundamental frequency in range of approximately 600 kHz-1000 kHz or 600 kHz-1 MHz which typically penetrates the lumen wall so as to treat or affect particular cells somewhat shallowly, such as epithelial or endothelial cells. It may be appreciated that at some voltages, frequencies at or below 100-250 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 800 kHz, while in other cases the treatment may be delivered using 2000 V with a waveform frequency of 400 kHz.

When used in opposing directions, the treatment parameters may be manipulated in a way that makes it too effective, which may increase muscle contraction likelihood or risk effects to undesirable tissues, such as cartilage for airway treatments. For instance, if the frequency is increased and the voltage is decreased, such as the use of 2000 V at 800 kHz, the treatment may not have sufficient clinical therapeutic benefit. Opposingly, if the voltage was increased to 3000 V and frequency decreased to 400 kHz, there may be undesirable treatment effect extent to collateral sensitive tissues. In some cases, the over-treatment of these undesired tissues could result in morbidity or safety concerns for the patient, such as destruction of cartilaginous tissue in the airways sufficient to cause airway collapse, or destruction of smooth muscle in the GI tract sufficient to cause interruption of normal peristaltic motion. In other cases, the overtreatment of the untargeted or undesirable tissues may have benign clinical outcomes and not affect patient response or morbidity if they are overtreated.

D. Packets

As mentioned, the algorithm 152 prescribes a signal having a waveform comprising a series of energy packets wherein each energy packet comprises a series of high voltage pulses. The cycle count 420 is half the number of pulses within each biphasic packet. Referring to FIG. 21A, the first packet 402 has a cycle count 420 of two (i.e. four biphasic pulses). In some embodiments, the cycle count 420 is set between 1 and 100 per packet, including all values and subranges in between. In some embodiments, the cycle count 420 is up to 5 pulses, up to 10 pulses, up to 25 pulses, up to 40 pulses, up to 60 pulses, up to 80 pulses, up to 100 pulses, up to 1,000 pulses or up to 2,000 pulses, including all values and subranges in between.

The packet duration is determined by the cycle count, among other factors such as inserted delays. In some embodiments, packet durations are in the range of approximately 50 to 1000 microseconds, such as 50 μs, 60 μs, 70 μs, 80 μs, 90 μs, 100 μs, 125 μs, 150 μs, 175 μs, 200 μs, 250 μs, 100 to 250 μs, 150 to 250 μs, 200 to 250 μs, 500 to 1000 μs to name a few. In other embodiments, the packet durations are in the range of approximately 100 to 1000 microseconds, such as 150 μs, 200 μs, 250 μs, 500 μs, or 1000 μs. In some embodiments, the inclusion of delays may increase the packet duration to a range of approximately 1000 to 200,000 microseconds, such as 2,000 μs, 5,000 μs, 10,000 μs, 20,000 μs, 25,000 μs, 30,000 μs, 40,000 μs, 50,000 μs, 60,000 μs, 70,000 μs, 80,000 μs, 90,000 μs, 100,000 μs, 110,000 μs, 120,000 μs, 130,000 μs, 140,000 μs, 150,000 μs, 160,000 μs, 170,000 μs, 180,000 μs, 190,000 μs, 200,000 μs, 1000-2000 μs, 1000-3000 μs, 1000-4000 μs, 1000-5000 μs, 1000-10, 000 μs, 10,000-20,000 μs, 10,000-30,000 μs, 10,000-40,000 μs, 10,000-50,000 μs, 50,000-100,000 μs, 50,000-150,000 μs, 50,000-200,000 μs, greater than 10,000 μs, greater than 25,000 μs, greater than 50,000 μs, greater than 100,000 μs, greater than 200,000 μs to name a few.

E. Waveforms

Figure 21B:
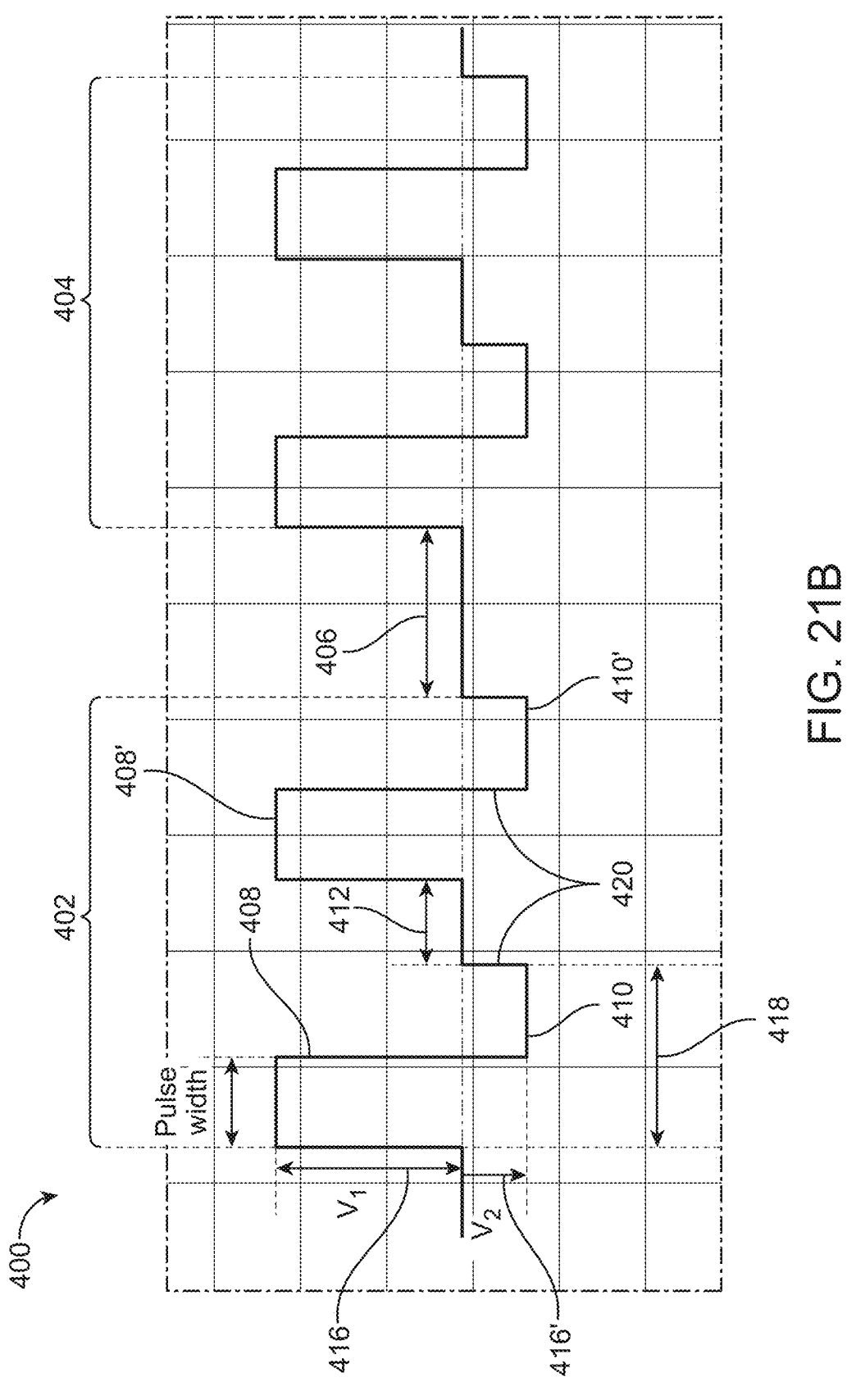
FIG. 21B illustrates various examples of biphasic pulses having an inter-phase time therebetween.
Figure 21C:
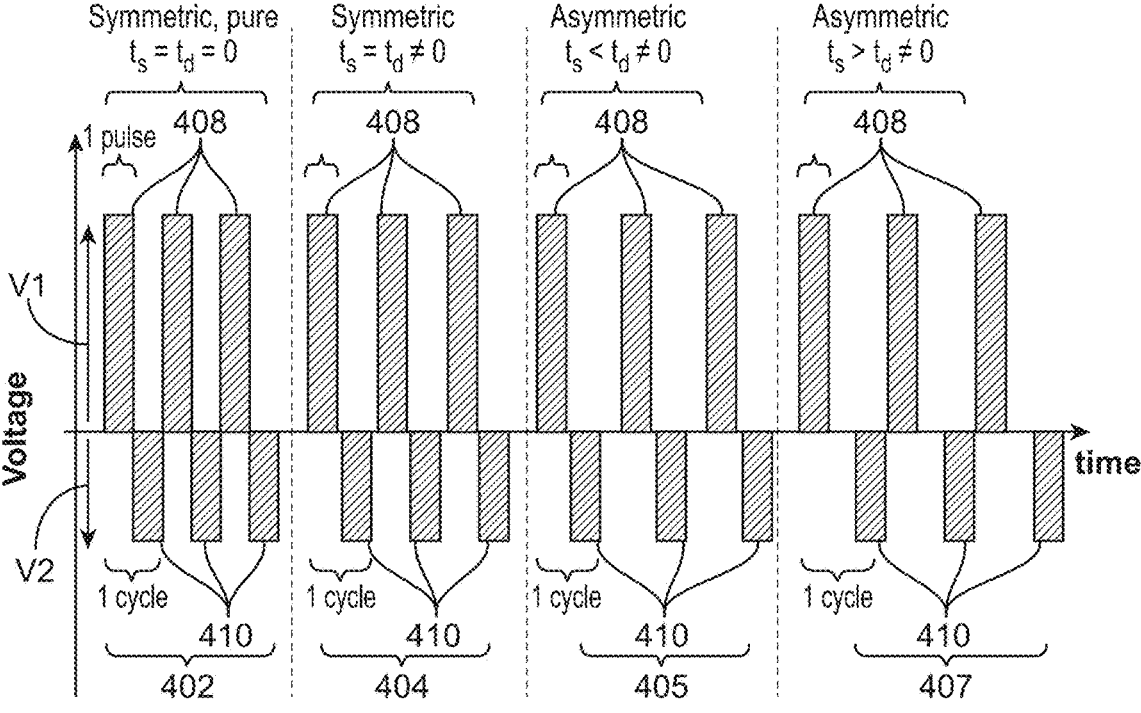
FIG. 21C illustrates further examples of waveforms having unequal voltages.

FIG. 21A illustrates an embodiment of a waveform 400 having symmetric pulses such that the voltage and duration of pulse in one direction (i.e., positive or negative) is equal to the voltage and duration of pulse in the other direction. FIG. 21B illustrates an example waveform 400 prescribed by another energy delivery algorithm 152 wherein the waveform 400 has voltage imbalance. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 having a first voltage V1 and a first negative pulse peak 410 having a second voltage V2) and a second biphasic cycle (comprising a second positive pulse peak 408' having first voltage V1 and a second negative pulse peak 410' having a second voltage V2). Here the first voltage V1 is greater than the second voltage V2. The first and second biphasic cycles are separated by dead time 412 between each pulse. Thus, the voltage in one direction (i.e., positive or negative) is greater than the voltage in the other direction so that the area under the positive portion of the curve does not equal the area under the negative portion of the curve. This unbalanced waveform may result in a more pronounced treatment effect as the dominant positive or negative amplitude leads to a longer duration of same charge cell membrane charge potential. In this embodiment, the first positive peak 408 has a set voltage 416 (V1) that is larger than the set voltage 416' (V2) of the first negative peak 410. FIG. 21C illustrates further examples of waveforms having unequal voltages. Here, four different types of packets are shown in a single diagram for condensed illustration. The first packet 402 is comprised of pulses having unequal voltages but equal pulse widths, along with no inter-phase delays and dead times. Thus, the first packet 402 is comprised of four biphasic pulses, each comprising a positive peak 408 having a first voltage V1 and a negative peak 410 having a second voltage V2). Here the first voltage V1 is greater than the second voltage V2. The second packet 404 is comprised of pulses having unequal voltages but symmetric pulse widths (as in the first pulse 402), with inter-phase delays equal to cycle delays. The third packet 405 is comprised of pulses having unequal voltages but symmetric pulse widths (as in the first pulse 402), with inter-phase delays that are shorter than cycle delays. The fourth packet 407 is comprised of pulses having unequal voltages but symmetric pulse widths (as in the first pulse 402), with inter-phase delays that are greater than cycle delays. It may be appreciated that in some embodiments, the positive and negative phases of biphasic waveform are not identical, but are balanced, where the voltage in one direction (i.e., positive or negative), is greater than the voltage in the other direction but the length of the pulse is calculated such that the area under the curve of the positive phase equals the area under the curve of the negative phase.

In some embodiments, imbalance includes pulses having pulse widths of unequal duration. In some embodiments, the biphasic waveform is unbalanced, such that the voltage in one direction is equal to the voltage in the other direction, but the duration of one direction (i.e., positive or negative) is greater than the duration of the other direction, so that the area under the curve of the positive portion of the waveform does not equal the area under the negative portion of the waveform.

Figure 21D:
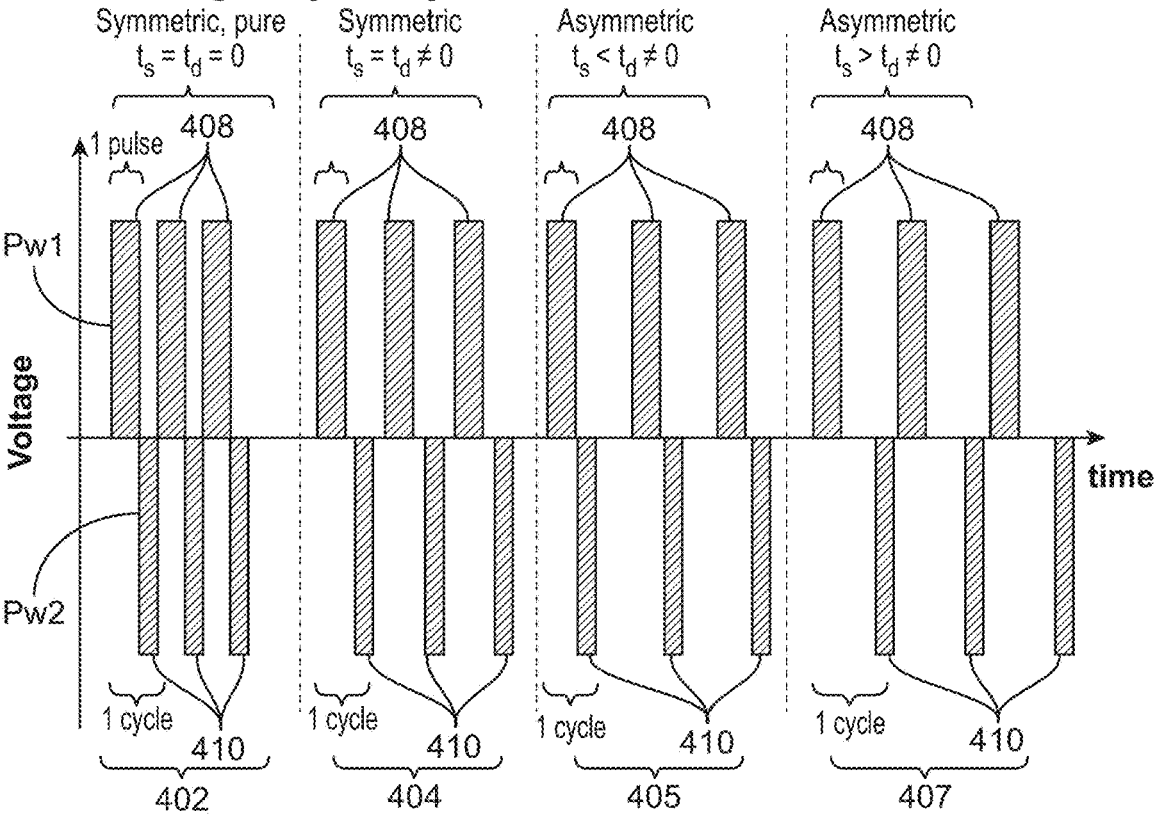
FIG. 21D illustrates further examples of waveforms having unequal pulse widths.

FIG. 21D illustrates further examples of waveforms having unequal pulse widths. Here, four different types of packets are shown in a single diagram for condensed illustration. The first packet 402 is comprised of pulses having equal voltages but unequal pulse widths, along with no inter-phase delays and cycle delays. Thus, the first packet 402 is comprised of four biphasic pulses, each comprising a positive peak 408 having a first pulse width PW1 and a negative peak 410 having a second pulse width PW2). Here the first pulse width PW1 is greater than the second pulse width PW2. The second packet 404 is comprised of pulses having equal voltages but unequal pulse widths (as in the first pulse 402), with inter-phase delays equal to cycle delays. The third packet 405 is comprised of pulses having equal voltages but unequal pulse widths (as in the first pulse 402), with inter-phase delays that are shorter than cycle delays. The fourth packet 407 is comprised of pulses having equal voltages but unequal pulse widths (as in the first pulse 402), with inter-phase delays that are greater than cycle delays.

Figure 21E:
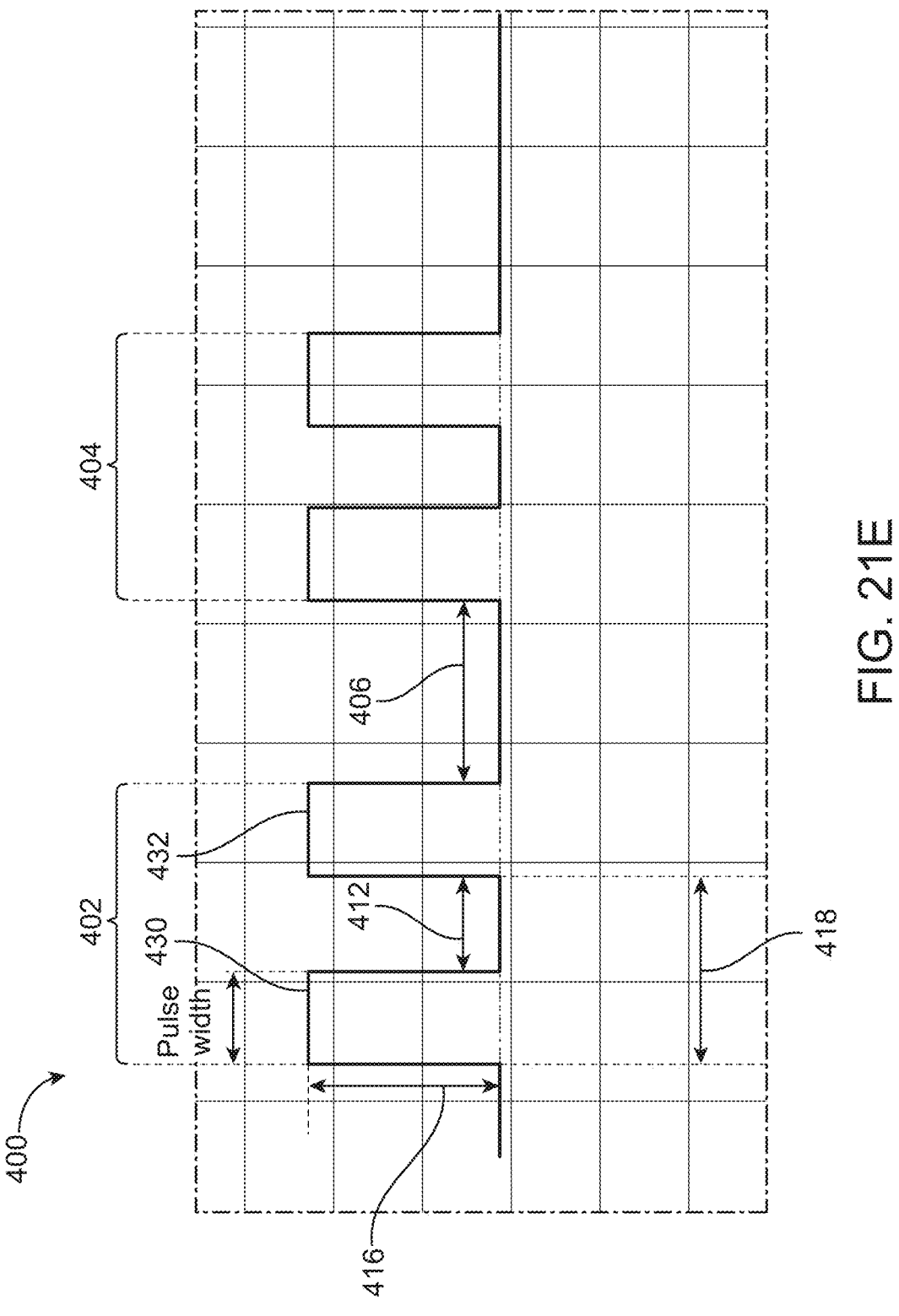
FIG. 21E illustrates an example waveform prescribed by another energy delivery algorithm wherein the waveform is monophasic.

FIG. 21E illustrates an example waveform 400 prescribed by another energy delivery algorithm 152 wherein the waveform is monophasic, a special case of imbalance whereby there is only a positive or only a negative portion of the waveform. Here, two packets are shown, a first packet 402 and a second packet 404, wherein the packets 402, 404 are separated by an inter-packet delay or rest period 406. In this embodiment, each packet 402, 404 is comprised of a first monophasic pulse 430 and a second monophasic pulse 432. The first and second monophasic pulses 430, 432 are separated by a cycle delay or dead time 412 between each cycle. This monophasic waveform could lead to a more desirable treatment effect as the same charge cell membrane potential is maintain for longer durations. However, adjacent muscle groups will be more stimulated by the monophasic waveform, compared to a biphasic waveform.

Figure 21F:
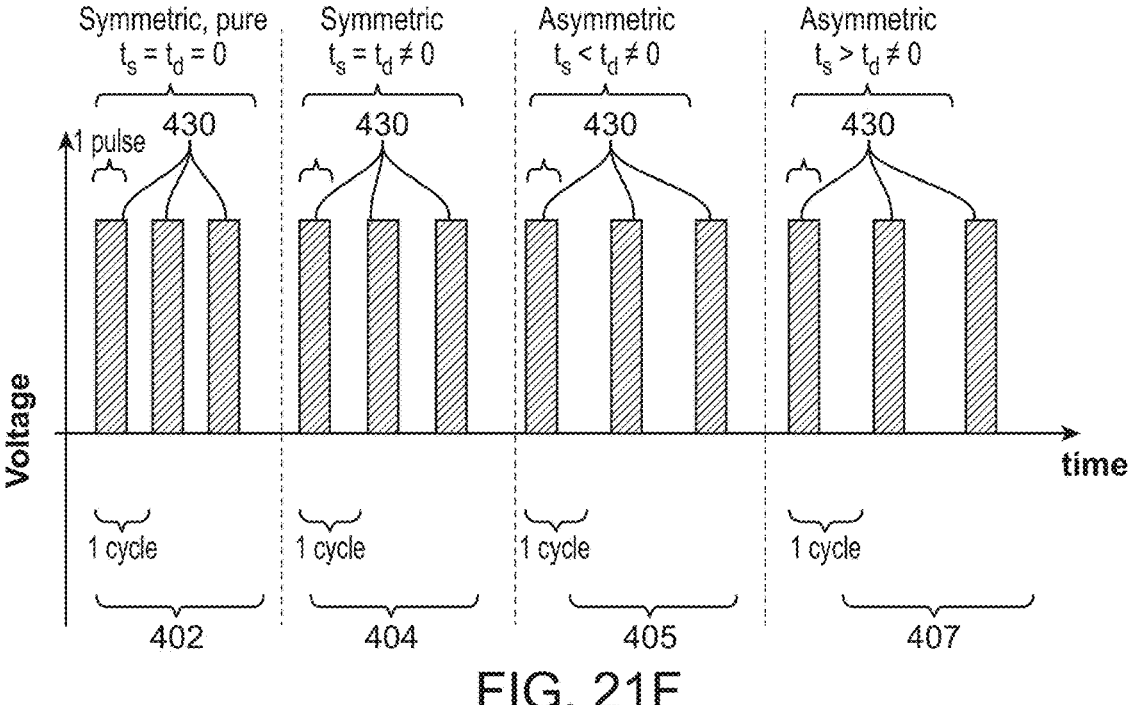
FIG. 21F illustrates further examples of waveforms having monophasic pulses.

FIG. 21F illustrates further examples of waveforms having monophasic pulses. Here, four different types of packets are shown in a single diagram for condensed illustration. The first packet 402 is comprised of pulses having identical voltages and pulse widths, with no switch times or inter-phase delays (because the pulses are monophasic) and a cycle delay equal to the active time. In some cases, there may be cycle delay duration than the active time of a given pulse. Thus, the first packet 402 is comprised of three monophasic pulses 430, each comprising a positive peak. In instances where the dead time is equal to the active time, the waveform may be considered unbalanced with a fundamental frequency representing a cycle period of 2×the active time and no dead time. The second packet 404 is comprised of monophasic pulses 430 having equal voltages and pulse widths (as in the first packet 402), with larger cycle delays. The third packet 405 is comprised of monophasic pulses 430 having equal voltages and pulse widths (as in the first packet 402), and even larger cycle delays. The fourth packet 407 is comprised of monophasic pulses 430 having equal voltages and pulse widths (as in the first packet 402), with yet larger cycle delays.

Figure 21G:
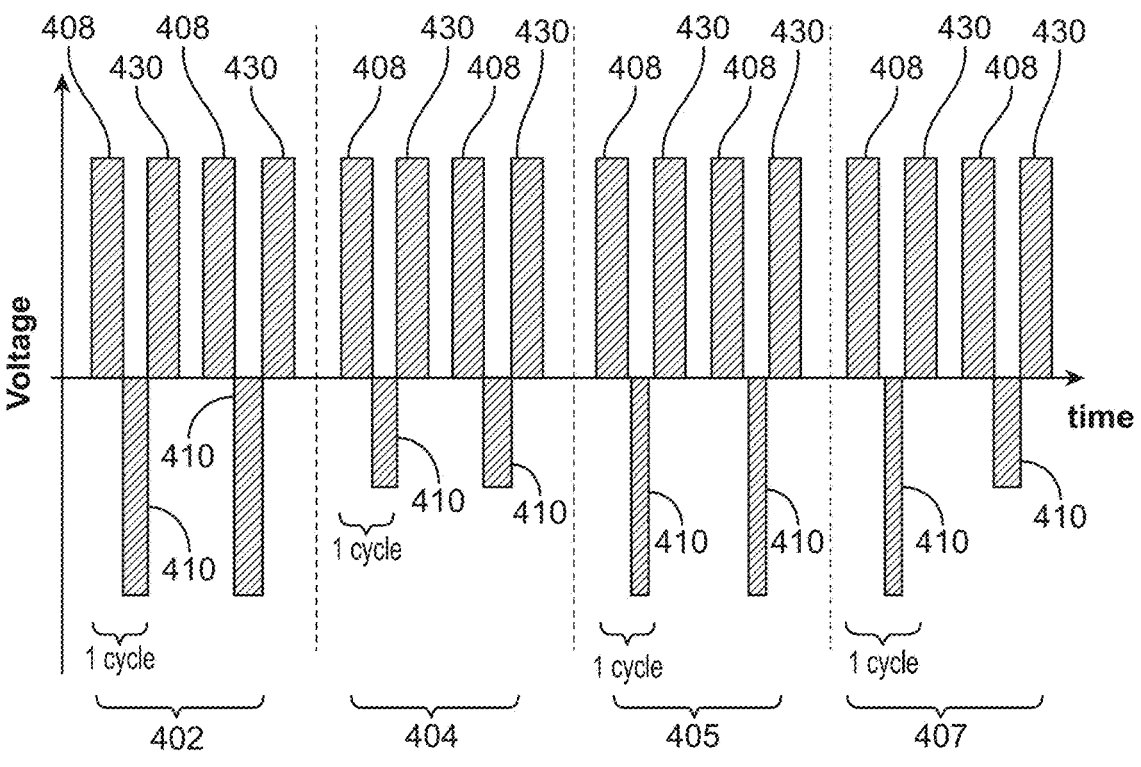
FIG. 21G illustrates further examples of waveforms having such phase imbalances.
Figure 21H:
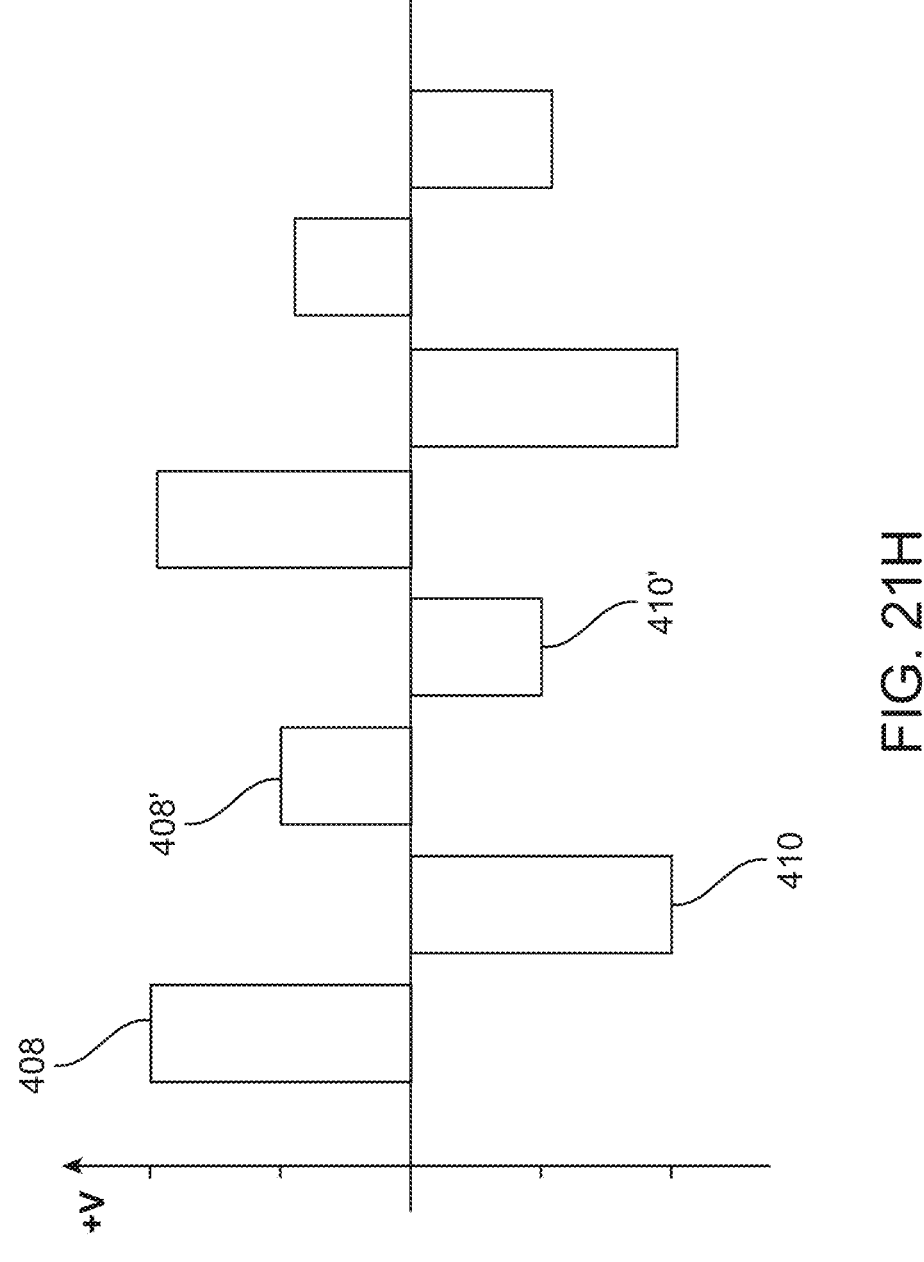
FIG. 21H illustrates an example of a waveform having imbalances in both positive and negative voltages.

In some embodiments, an unbalanced waveform is achieved by delivering more than one pulse in one polarity before reversing to an unequal number of pulses in the opposite polarity. FIG. 21G illustrates further examples of waveforms having such phase imbalances. Here, four different types of packets are shown in a single diagram for condensed illustration. The first packet 402 is comprised of four cycles having equal voltages and pulse widths, however, opposite polarity pulses are intermixed with monophasic pulses. Thus, the first cycle comprises a positive peak 408 and a negative peak 410. The second cycle is monophasic, comprising a single positive pulse with no subsequent negative pulse 430. This then repeats. The second packet 404 is comprised of intermixed biphasic and monophasic cycles (as in the first packet 402), however the pulses have unequal voltages. The third packet 405 is comprised of intermixed biphasic and monophasic cycles (as in the first packet 402), however the pulses have unequal pulse widths. The fourth packet 407 is comprised of intermixed biphasic and monophasic pulses (as in the first packet 402), however the pulses have unequal voltages and unequal pulse widths. Thus, multiple combinations and permutations are possible. FIG. 21H illustrates an example of a waveform having imbalances in both positive and negative voltages. Here a packet is shown having a first positive pulse peak 408 and a first negative pulse peak 410 having a greater voltage than a second positive pulse peak 408' and a second negative pulse peak 410'. These differing cycles repeat throughout the packet.

Regarding the utility of unequal waveforms, the unbalanced TMP manipulation achieved reduces the implications of biphasic cancellation. There is a correlative relationship between the degree of imbalance, approaching a monopolar waveform as fully unbalanced, and the intensity of TMP manipulation. This will result in proportional relationship between the extent of treatment effect as well as the degree of muscle contraction. Thus, approaching more unbalanced waveforms will enable stronger treatment effects at the same voltage and frequency (if applicable) for biphasic waveforms than those produced from purely balanced biphasic waveforms. For example, the treatment effect evoked by a 830 ns-415 ns-830 ns-etc pulse length sequence within a packet will have the pulse constituting the second half of the cycle being half the duration of the original phase. This will restrict the induction of TMP manipulation by the second phase of the cycle, but will also generate less reversed TMP, enabling a stronger effect from the original polarity in the subsequent cycle at the original length. In another example, the "positive" portion of the waveform may be 2500V, with the "negative" portion being 1500V (2500-1250-2500-etc V), which will induce comparable effects on TMP polarization as that which was described for the pulse duration imbalance. In both of these cases, the manipulation of the opposing polarity intensity will result in cumulative stronger TMP manipulation for the positive pulse in the cycle. This will thus reduce the effects of biphasic cancellation and will generate stronger treatment effects than a protocol of 830-830-830 ns or 2500-2500-2500V, despite the deposition of less total energy delivered to the tissue. In this way, it is possible to deliver less total energy to the tissue but evoke the desired treatment effect when TMP manipulations are integral to the treatment mechanism of action.

Extended further, the fully unbalanced waveforms would not include any opposite polarity component but may still include brief portions of pulses delivered in just the positive phase. An example of this is a packet that contains 830 ns of positive polarity, an 830 ns pause with no energy delivered, followed by another 830 ns of positive polarity, and so forth. The same approach is true whether considering the pulse length imbalance or the voltage imbalance, as the absence of a negative pulse is equivalent to setting either of these parameters to zero for the "negative" portion.

However, appropriate treatment delivery considers that the advantages offered by biphasic waveforms, namely the reduction of muscle contraction, resulting from biphasic cancellation will likewise be reduced. Therefore, the appropriate treatment effect extent is balanced against the degree of acceptable muscle contraction. For example, an ideal voltage imbalance may be 2500-1000-2500- . . . V, or 2500-2000-2500- . . . V; or 830-100-830- . . . ns, or 830-500-830- . . . ns.

It may be appreciated that in some embodiments the pulses are sinusoidal in shape rather than square. One benefit of a sinusoidal shape is that it is balanced or symmetrical, whereby each phase is equal in shape. Balancing may assist in reducing undesired muscle stimulation. It may be appreciated that in other embodiments the pulses have decay-shaped waveforms.

Alternative Delivery Approaches

As mentioned previously, in most embodiments, access is minimally invasive and relies on endoluminal approaches. However, it may be appreciated that other approaches, such as percutaneous, laparoscopic or open surgical approaches, may be used in some situations.

In some embodiments, when accessing percutaneously, the shaft 106 of the device 102 is passed through a delivery device that penetrates the skin layer into the underlying tissue. In some embodiments, the delivery device comprises a needle that is inserted through the skin and directed toward the target tissue. The shaft 106 is then advanced through the needle. In some embodiments, the probe tip 502 is shaped to assist in penetrating tissue, such as a pointed shape. Thus, the shaft 106 may be advanced through tissue to the desired location therein. Once desirably positioned, energy is delivered through the probe tip 502 to treat the target tissue. It may be appreciated that the probe tip 502 may also be advanced from the shaft 106 into the tissue and/or a conductive element 560 may be advanced into the tissue wherein the energy is delivered from the conductive element 560.

In other embodiments, when accessing percutaneously, the shaft 106 of the device 102 is rigid so as to be able to penetrate the skin layer without the use of a delivery device. In such embodiments, the probe tip 502 is typically shaped to assist in penetrating tissue, such as a pointed shape. Thus, the shaft 106 itself is advanced into the tissue to the desired location therein. Once desirably, positioned, energy is delivered through the probe tip 502 to treat the target tissue. It may be appreciated that the probe tip 502 may also be advanced from the shaft 106 into the tissue and/or a conductive element 560 may be advanced into the tissue wherein the energy is delivered from the conductive element 560.

In laparoscopic approaches, the shaft 106 of the device 102 is passed through a laparoscope which has been inserted through a small incision. These small incisions provide reduced pain, reduced hemorrhaging and shorter recovery time in comparison to open surgery. In some embodiments, the probe tip 502 is shaped to assist in penetrating tissue, such as a pointed shape. Thus, the shaft 106 may be advanced through tissue to the desired location therein. Once desirably positioned, energy is delivered through the probe tip 502 to treat the target tissue.

In open surgical approaches, the shaft 106 of the device 102 may also be passed through a delivery device or the device 102 may penetrate the tissue directly. In either case, once desirably positioned, energy is delivered through the probe tip 502 to treat the target tissue.

Cardiac Synchronization

Figure 22:
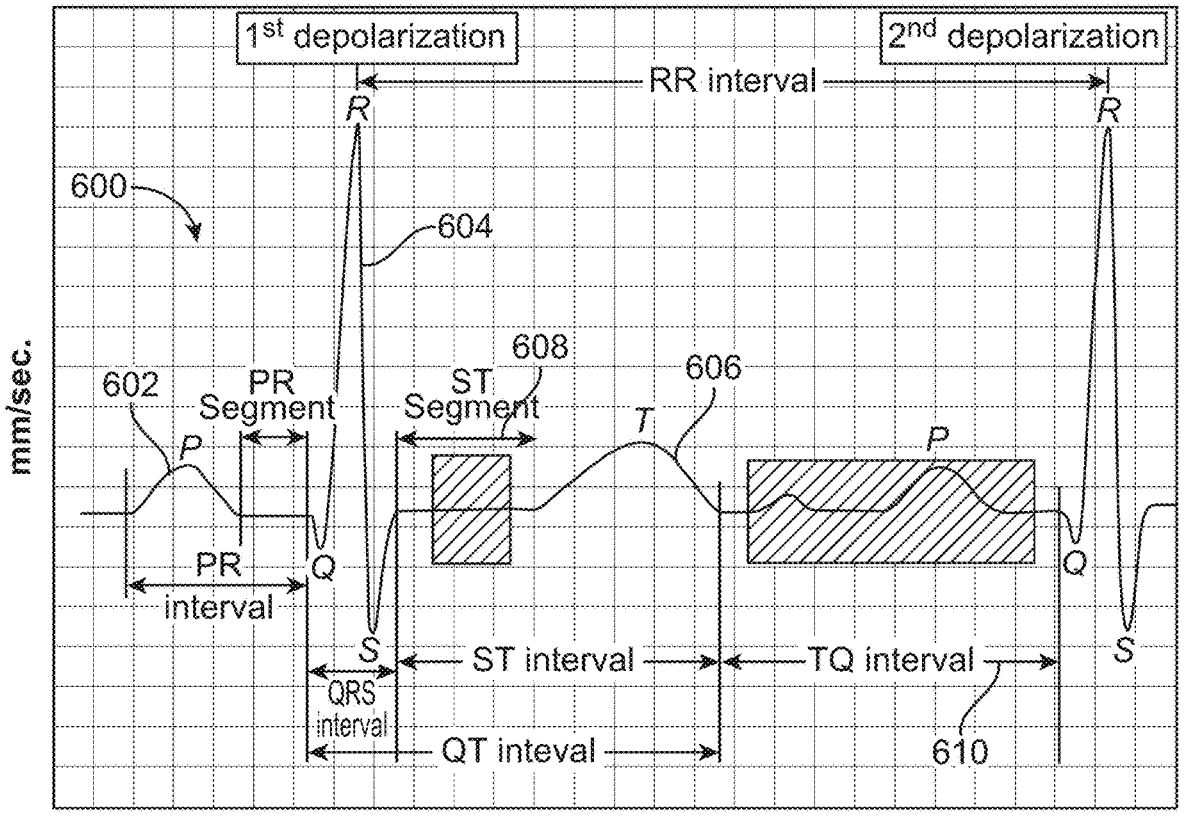
FIG. 22 is a graph illustrating portions of a sample electrocardiogram (ECG) trace of a human heart highlighting periods wherein it is desired to deliver energy pulses to the lung passageway via the energy delivery body.

In some embodiments, the energy signal is synchronized with the patient's cardiac cycle to prevent induction of cardiac arrhythmias. Thus, the patient's cardiac cycle is typically monitored with the use of an electrocardiogram (ECG). Referring to FIG. 22, a typical ECG trace 600 includes a repeating cycle of a P wave 602 representing atrial depolarization, a QRS complex 604 representing ventricular depolarization and atrial repolarization, and a T wave 606 representing ventricular repolarization. To safely deliver energy within the airway in close proximity to the heart, synchronization between energy delivery and the patient's cardiac cycle is employed to reduce the risk of cardiac arrhythmia. High voltage energy can trigger a premature action potential within the cardiac muscle as the delivered energy increases the cardiac muscle cell membrane permeability allowing ion transport, which can induce cardiac arrhythmias, especially ventricular fibrillation. To avoid cardiac arrhythmias, the electrical energy is delivered to the airway in a fashion that is outside the "vulnerable period" of the cardiac muscle. Within one cardiac cycle (heartbeat), the vulnerable period of the ventricular muscle is denoted on an ECG by the entire T wave 606. Typically, for ventricular myocardium, the vulnerable period coincides with the middle and terminal phases of the T wave 606. However, when high energy pulses are delivered in close proximity to the ventricle, the vulnerable period can occur several milliseconds earlier in the heartbeat. Therefore, the entire T wave can be considered to be within the vulnerable period of the ventricles.

The remaining parts of a cardiac cycle are the P wave 602 and the QRS complex 604, which both include periods when atrial or ventricular muscle is refractory to high voltage energy stimuli. If high voltage energy pulses are delivered during the muscle's refractory period, arrhythmogenic potential can be minimized. The ST segment 608 (interval between ventricular depolarization and repolarization) of the first cardiac cycle and the TQ interval 610 (interval including the end of the first cardiac cycle and the mid-point of the second cardiac cycle) are the periods where high voltage energy can be delivered without induction of cardiac arrhythmia due to the cardiac muscle depolarized state (refractory period). FIG. 22 includes shaded boxes that indicate example portions of the cardiac cycle during which energy can be applied safely.

It may be appreciated that in some embodiments, components for acquiring the electrocardiogram 170 are integrally formed as part of the generator 104. If the cardiac monitor is limited to acquiring up to a 5-lead ECG, and it may be beneficial to incorporate additional leads into the system. This would further eliminate the need to use the communications port 167 to receive cardiac sync pulses.

Rather, the processor 154 can be configured to detect the R-waves directly and to assess the integrity of the entire QRS complex.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" can be used interchangeably.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the pulsed electric field energy provides a treatment to the tissue, wherein the pulsed electric field energy is generated from a waveform comprising at least one packet of pulses having one or more delay periods so that each packet has a duty cycle of less than or equal to 2.5 percent, which manipulates or reduces or avoids one or more secondary effects, wherein the pulsed electric field energy causes cell death by non-thermal effects.

2. The system of claim 1, wherein the one or more secondary effects comprises cavity formation in the tissue.

3. The system of claim 1, wherein the pulses are biphasic pulses and wherein the at least one of the one or more delay periods is a cycle delay or phase delay of approximately 1,000 microseconds to 10,000 microseconds.

4. The system of claim 1, wherein the one or more secondary effects comprises an electrical discharge event.

5. The system of claim 4, wherein the electrical discharge event comprises electrical arcing from at least one of the at least one electrode.

6. The system of claim 4, wherein the pulses are biphasic pulses and wherein the at least one of the one or more delay periods is a cycle delay or phase delay of approximately 250 microseconds.

7. The system of claim 4, wherein the electrical discharge event comprises generation of a pressure wave against the tissue.

8. The system of claim 7, wherein the pressure wave is sufficient to generate a cavity within the tissue.

9. The system of claim 8, wherein each of the one or more packets of pulses has an on-time in a range of 0.5 to 20 microseconds.

10. The system of claim 1, wherein the one or more secondary effects comprises bubble formation.

11. The system of claim 10, wherein bubble formation comprises formation of bubbles greater than or equal to 0.1 mm in diameter.

12. The system of claim 1, wherein at least one of the one or more delay periods is in a range of 250 microseconds to 1000 microseconds.

13. The system of claim 1, wherein the one or more packets of pulses comprises 100 packets.

14. The system of claim 1, wherein each of the one or more packets has a cycle count of up to 60 cycles.

15. The system of claim 1, wherein the one or more secondary effects comprises a contraction of a muscle.

16. The system of claim 15, wherein the at least one electrode is configured to create a lesion having a width and wherein reducing or avoiding contraction of the muscle causes the at least one electrode to maintain a position that does not move more than 25% of the width.

17. The system of claim 1, wherein the pulses comprise biphasic pulses and the delay period comprises an inter-phase delay between a positive phase and a negative phase of a biphasic pulse.

18. The system of claim 1, wherein the waveform comprises one or more bundles separated by an inter-bundle delay, wherein each bundle comprises two or more packets.

19. The system of claim 1, further comprising a remote dispersive electrode positionable so that the pulsed electric field energy is delivered in a monopolar manner.

20. A system for treating tissue of a patient comprising:
an energy delivery device having at least one energy delivery body having a form of a probe, wherein the probe is configured to penetrate the tissue; and
a generator in electrical communication with the at least one energy delivery body, wherein the generator includes at least one energy delivery algorithm that provides pulsed electric field energy to the energy delivery body so that the pulsed electric field energy provides a treatment to the tissue, wherein the pulsed electric field energy is generated from a waveform comprising a plurality of packets of pulses to provide the treatment and comprising one or more delay periods positioned within the waveform so that each packet has a duty cycle of less than or equal to 2.5 percent so as to reduce or avoid cavity formation around the probe in the tissue, wherein the pulsed electric field energy causes cell death by non-thermal effects.

21. The system of claim 20, wherein at least one of the one or more delay periods is greater than 100 microseconds.

22. The system of claim 20, wherein the pulses are biphasic pulses and wherein the at least one of the one or more delay periods is a cycle delay or phase delay.

23. A system for treating tissue of a patient comprising:
at least one electrode positionable near the tissue; and
a generator in electrical communication with the at least one electrode, wherein the generator includes at least one energy delivery algorithm that provides pulsed electric field energy to the electrode so that the pulsed electric field energy provides a treatment to the tissue, wherein the pulsed electric field energy is generated from a waveform comprising at least one packet of pulses which causes a temperature rise spike within the tissue, wherein each packet of pulses includes one or more delay periods so that each packet has a duty cycle of less than or equal to 2.5 percent, which affect an amplitude of the temperature rise spike in an amount sufficient to reduce or avoid an electrical discharge event, wherein the pulsed electric field energy causes cell death by non-thermal effects.

24. The system of claim 23, wherein each of the one or more delay periods is 200 microseconds to 20,000 microseconds.

25. The system of claim 23, wherein each of the one or more delay periods is 1,000 microseconds to 10,000 microseconds.

\* \* \* \* \*